(12) United States Patent
Morrison et al.

US011890320B2

(10) Patent No.: US 11,890,320 B2
(45) Date of Patent: *Feb. 6, 2024

(54) CLEC11A IS A BONE GROWTH AGENT

(71) Applicant: The Board of Regents of the University of Texas System, Austin, TX (US)

(72) Inventors: Sean Morrison, Dallas, TX (US); Rui Yue, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 522 days.

This patent is subject to a terminal disclaimer.

(21) Appl. No.: 16/864,872

(22) Filed: May 1, 2020

(65) Prior Publication Data

US 2020/0297816 A1     Sep. 24, 2020

Related U.S. Application Data

(63) Continuation of application No. 15/567,762, filed as application No. PCT/US2016/028066 on Apr. 18, 2016, now Pat. No. 11,285,190.

(60) Provisional application No. 62/293,373, filed on Feb. 10, 2016, provisional application No. 62/275,570, filed on Jan. 6, 2016, provisional application No. 62/150,071, filed on Apr. 20, 2015.

(51) Int. Cl.
*A61K 38/18* (2006.01)
*A61P 19/08* (2006.01)
*A61K 38/29* (2006.01)
*A61K 45/06* (2006.01)
*A61P 35/04* (2006.01)
*A61P 19/10* (2006.01)

(52) U.S. Cl.
CPC .............. *A61K 38/18* (2013.01); *A61K 38/29* (2013.01); *A61K 45/06* (2013.01); *A61P 19/08* (2018.01); *A61P 19/10* (2018.01); *A61P 35/04* (2018.01)

(58) Field of Classification Search
CPC ........... A61K 38/18; A61P 19/08; A61P 19/10
See application file for complete search history.

(56) References Cited

U.S. PATENT DOCUMENTS

| | | |
|---|---|---|
| 4,722,948 A | 2/1988 | Sanderson |
| 4,843,112 A | 6/1989 | Gerhart et al. |
| 4,863,732 A | 9/1989 | Nathan et al. |
| 4,975,526 A | 12/1990 | Kuberasampath et al. |
| 5,085,861 A | 2/1992 | Gerhart et al. |
| 5,162,114 A | 11/1992 | Kuberasampath et al. |
| 5,312,256 A | 5/1994 | Scortecci |
| 5,364,268 A | 11/1994 | Lazzara et al. |
| 5,383,935 A | 1/1995 | Shirkhanzadeh |
| 5,397,358 A | 3/1995 | Wenner et al. |
| 5,399,363 A | 3/1995 | Liversidge et al. |
| 5,405,388 A | 4/1995 | Fox |
| 5,441,538 A | 8/1995 | Bonutti |
| 5,456,723 A | 10/1995 | Steinemann et al. |
| 5,466,468 A | 11/1995 | Schneider et al. |
| 5,531,791 A | 7/1996 | Wolfinbarger, Jr. |
| 5,543,158 A | 8/1996 | Gref et al. |
| 5,571,185 A | 11/1996 | Schug |
| D378,314 S | 3/1997 | Koros et al. |
| 5,607,430 A | 3/1997 | Bailey |
| 5,624,462 A | 4/1997 | Bonutti |
| 5,629,001 A | 5/1997 | Michael et al. |
| 5,639,402 A | 6/1997 | Barlow et al. |
| 5,641,515 A | 6/1997 | Ramtoola |
| D381,080 S | 7/1997 | Ohata |
| 5,658,338 A | 8/1997 | Tullos et al. |
| 5,674,725 A | 10/1997 | Beertsen et al. |
| 5,709,547 A | 1/1998 | Lazzara et al. |
| 5,709,683 A | 1/1998 | Bagby |
| 5,720,750 A | 2/1998 | Koller et al. |
| 5,741,796 A | 4/1998 | Hartman et al. |
| 5,759,035 A | 6/1998 | Ricci |
| 5,810,589 A | 9/1998 | Michnick et al. |
| 5,819,748 A | 10/1998 | Pfirrmann |
| 5,840,290 A | 11/1998 | Hench et al. |
| 5,885,287 A | 3/1999 | Bagby |
| 5,890,902 A | 4/1999 | Sapian |
| 5,895,425 A | 4/1999 | Grafton et al. |
| 5,899,939 A | 5/1999 | Boyce et al. |
| 5,906,488 A | 5/1999 | Kvarnstrom |
| 5,976,147 A | 11/1999 | LaSalle et al. |
| 6,018,094 A | 1/2000 | Fox |
| 6,058,590 A | 5/2000 | Roberts et al. |
| 6,074,674 A | 6/2000 | Jay et al. |

(Continued)

FOREIGN PATENT DOCUMENTS

| | | | |
|---|---|---|---|
| WO | 1998008869 A1 | 3/1998 | |
| WO | WO-9808869 A1 * | 3/1998 | ........... C07K 14/475 |

OTHER PUBLICATIONS

Engelhardt et al., Deutsche Medizinische Wochenschrift (1946), 2012, 137(20):1057-1061 (English Abstract).*
Bannwarth et al., "Cloning, Mapping, and Genomic Organization of the LSLCL Gene, Encoding a New Lymphocytic Secreted Mucin-like Protein with a C-Type Lectin Domain: A New Model of Exon Shuffling," Genomics, 57(2):316-317, 1999.
Bannwarth et al., "Molecular cloning of a new secreted sulfated mucin-like protein with a C-type lectin domain that is expressed in lymphoblastic cells," J. Biol. Chem., 273:1911-1916, 1998.
Ding and Morrison, "Haematopoietic stem cells and early lymphoid progenitors occupy distinct bone marrow niches," Nature, 495(7440):231-235, 2013.
Ding et al., "Endothelial and perivascular cells maintain haematopoietic stem cells," Nature 481(7382):457-462, 2012.

(Continued)

*Primary Examiner* — Xiaozhen Xie
(74) *Attorney, Agent, or Firm* — POLSINELLI PC

(57) ABSTRACT

The present disclosure describes the C-type lectin CLEC11a as a bone growth factor. Clec11a-deficient mice showed reduced bone volume and mineralization, while bone resorption remained unchanged. Administration of recombinant Clec11a systemically promoted bone formation in mice at risk for osteoporosis.

10 Claims, 37 Drawing Sheets

Specification includes a Sequence Listing.

(56) References Cited

U.S. PATENT DOCUMENTS

| | | |
|---|---|---|
| 6,083,264 A | 7/2000 | Wood et al. |
| 6,126,662 A | 10/2000 | Carmichael et al. |
| 6,149,686 A | 11/2000 | Kuslich et al. |
| 6,149,688 A | 11/2000 | Brosnahan et al. |
| 6,149,689 A | 11/2000 | Grundei |
| 6,203,545 B1 | 3/2001 | Stoffella |
| 6,206,923 B1 | 3/2001 | Boyd et al. |
| 6,213,775 B1 | 4/2001 | Reipur |
| 6,214,050 B1 | 4/2001 | Huene |
| 6,217,617 B1 | 4/2001 | Bonutti |
| 6,248,109 B1 | 6/2001 | Stoffella |
| 6,270,346 B1 | 8/2001 | Grabenhofer et al. |
| 6,270,750 B1 | 8/2001 | Dioguardi |
| 6,281,195 B1 | 8/2001 | Rueger et al. |
| 6,287,343 B1 | 9/2001 | Kuslich et al. |
| 6,288,043 B1 | 9/2001 | Spiro et al. |
| 6,350,126 B1 | 2/2002 | Levisman |
| 6,350,283 B1 | 2/2002 | Michelson |
| 6,364,880 B1 | 4/2002 | Michelson |
| 6,370,418 B1 | 4/2002 | Bernoski |
| 6,371,986 B1 | 4/2002 | Bagby |
| 6,436,146 B1 | 8/2002 | Hassler et al. |
| 6,447,545 B1 | 9/2002 | Bagby |
| 6,458,136 B1 | 10/2002 | Allard et al. |
| 6,478,825 B1 | 11/2002 | Winterbottom et al. |
| 6,485,754 B1 | 11/2002 | Wenz et al. |
| 6,506,051 B2 | 1/2003 | Levisman |
| 6,537,277 B2 | 3/2003 | Berg et al. |
| 6,537,514 B1 | 3/2003 | Prasad et al. |
| D473,944 S | 4/2003 | Anderson |
| 6,540,770 B1 | 4/2003 | Tornier et al. |
| 6,541,217 B2 * | 4/2003 | Hiraoka ............... C07K 14/475 435/254.11 |
| 6,562,073 B2 | 5/2003 | Foley |
| 6,562,074 B2 | 5/2003 | Gerbec et al. |
| 6,599,322 B1 | 7/2003 | Amrich et al. |
| 6,607,557 B1 | 8/2003 | Brosnahan et al. |
| 6,613,308 B2 | 9/2003 | Bartus et al. |
| 6,648,917 B2 | 11/2003 | Gerbec et al. |
| 6,652,592 B1 | 11/2003 | Grooms et al. |
| 6,662,805 B2 | 12/2003 | Frondoza et al. |
| 6,666,890 B2 | 12/2003 | Michelson |
| 6,689,136 B2 | 2/2004 | Stoffella |
| 6,689,167 B2 | 2/2004 | Bagby |
| 6,730,129 B1 | 5/2004 | Hall |
| 6,755,832 B2 | 6/2004 | Happonen et al. |
| 6,761,738 B1 | 7/2004 | Boyd |
| 6,767,367 B1 | 7/2004 | Michelson |
| 6,786,908 B2 | 9/2004 | Hover et al. |
| 6,802,845 B2 | 10/2004 | Shirado et al. |
| 6,852,129 B2 | 2/2005 | Gerbec et al. |
| 6,860,884 B2 | 3/2005 | Shirado et al. |
| 6,899,734 B2 | 5/2005 | Castro et al. |
| 6,913,621 B2 | 7/2005 | Boyd et al. |
| 6,918,766 B1 | 7/2005 | Hall et al. |
| 6,921,264 B2 | 7/2005 | Mayer et al. |
| 6,923,830 B2 | 8/2005 | Michelson |
| 6,929,662 B1 | 8/2005 | Messerli et al. |
| 6,936,270 B2 | 8/2005 | Watson et al. |
| 6,981,872 B2 | 1/2006 | Ballan |
| 6,981,975 B2 | 1/2006 | Michelson |
| 6,988,015 B1 | 1/2006 | Schöpf et al. |
| 6,989,031 B2 | 1/2006 | Michelson |
| 6,994,726 B2 | 2/2006 | Lin et al. |
| 7,001,551 B2 | 2/2006 | Meredith |
| 7,008,433 B2 | 3/2006 | Voellmicke et al. |
| 7,022,137 B2 | 4/2006 | Michelson |
| 7,044,972 B2 | 5/2006 | Mathys, Jr. et al. |
| 7,251,568 B2 | 7/2007 | Pittman et al. |
| 11,285,190 B2 | 3/2022 | Morrison et al. |
| 2003/0031695 A1 * | 2/2003 | Kadiyala ............... A61L 27/3895 424/428 |
| 2005/0066266 A9 * | 3/2005 | Hastings ............... C07K 14/475 435/69.1 |
| 2007/0264341 A1 | 11/2007 | Lee et al. |
| 2011/0206645 A1 * | 8/2011 | Zhang ............... C12N 5/0605 435/375 |
| 2014/0127192 A1 * | 5/2014 | San Martin ........ A61K 39/3955 424/139.1 |
| 2018/0110832 A1 | 4/2018 | Morrison et al. |

OTHER PUBLICATIONS

Hiraoka et al., "Cloning, expression, and characterization of a cDNA encoding a novel human growth factor for primitive hematopoietic progenitor cells," Proc. Natl. Acad. Sci. USA, 94(14):7577-7582, 1997.

Hiraoka et al., "Stem cell growth factor: in situ hybridization analysis on the gene expression, molecular characterization and in vitro proliferative activity of a recombinant preparation on primitive hematopoietic progenitor cells," Hematol. J., 2(5):307-315, 2001.

International Preliminary Report on Patentability issued in corresponding PCT Application No. PCT/US2016/028066, dated Nov. 2, 2017.

International Search Report and Written Opinion issued in corresponding PCT Application No. PCT/US2016/028066, dated Aug. 30, 2016.

Ito et al., "Serum stem cell growth factor for monitoring hematopoietic recovery following stem cell transplantation," Bone Marrow Transplant., 32:391-398, 2003.

McComsey et al., Clin. Infect Dis., 2010, vol. 51(8): 937-946.

Mio et al., "Isolation and characterization of a cDNA for human, mouse, and rat full-length stem cell growth factor, a new member of C-type lectin superfamily," Biochem. Biophys. Res. Comm., 249:124-130, 1998.

Wang et al., Cytokine, 2013, vol. 61:728-731.

Zheng et al., "Impact of aging on rat bone marrow-derived stem cell chondrogenesis," J. Gerontol. A Biol. Sci. Med. Sci., 62(2):136-148, 2007.

Klein et al., Nature, 327:70-73, 1987.
Koch et al., Mal. Cell. Biol., 9:303, 1989.
Kondo et al., Cell 91, 661-672, 1997.
Kraenzlin and Meier, Nature Reviews Endocrinology 7, 647-656, 2011.
Kriegler et al., Cell, 38:483, 1984.
Kriegler et al., Cell, 53:45, 1988.
Krishnan et al., J Clin Invest 116, 1202-1209, 2006.
Kuhl et al., Cell, 50: 1057, 1987.
Kunisaki et at., Nature 502, 637-643, 2013.
Kunz et al., Nucl. Acids Res., 17: 1121, 1989.
Larsen et al., Proc. Natl. Acad. Sci. USA., 83:8283, 1986.
Laspia et al., Cell, 59:283, 1989.
Latimer et al.,Mol. Cell. Biol., 10:760, 1990.
Le Gal La Salle et al., Science, 259:988-990, 1993.
Lee et al., Cell 130, 456-469, 2007.
Lee et al., Nature, 294:228, 1981.
Lee et al., Nucleic Acids Res., 12:4191-206, 1984.
Leucht et al., Development 135, 2845-2854, 2008.
Levinson et al., Nature, 295:79, 1982.
Levrero et al., Gene, 101: 195-202, 1991.
Li et al., J Biol Chem 280, 19883-19887, 2005.
Liberman etal., N Engl J Med 333, 1437-1443, 1995.
Lin et al.,Mol. Cell. Biol., 10:850, 1990.
Liu et al., PLoS One 8, e71318, 2013.
Luria et al., RMRO.J., 6:3307, 1987.
Lusky et al.,Mol. Cell. Biol., 3:1108, 1983.
Mabuchi et al., Ann Transl Med 3, S 17, 2015.
Mabuchi et al., Stem Cell Reports 1, 152-165, 2013.
Macejak and Samnow, Nature, 353:90-94, 1991.
Maes et al., Developmental Cell 19, 329-344, 2010.
Mann et al., Cell, 33: 153-159, 1983.
Markowitz et al., J Virol., 62:1120-1124, 1988.
McClung et al., N Engl J Med 370, 412-420, 2014.
McLaughlin et al., Bone 30, 924-930, 2002.
McNeall et al., Gene, 76:81, 1989.
Mendez-Ferrer et al., Nature 466, 829-834, 2010.
Michaelsson et al., BMJ 316, 1858-1863, 1998.

(56) References Cited

OTHER PUBLICATIONS

Miksicek et al., Cell, 46:203, 1986.
Mio et al., Biochemical and Biophysical Research Communications 249, 124-130, 1998.
Mizoguchi et al., Developmental Cell 29, 340-349, 2014.
Moreau et al., Nucl. Acids Res., 9:6047, 1981.
Morikawa et al., J Exp Med 206, 2483-2496, 2009.
Morrison eta!., Cell 101, 499-510, 2000.
Muesing et al., Cell, 48:691, 1987.
Nakamura et al., J Clin Invest 117, 3075-3086, 2007.
Neer et al., N Engl J Med 344, 1434-1441, 2001.
Ng et al., Nuc. Acids Res., 17:601, 1989.
Nicolas and Rubinstein, In: Vectors: A survey of molecular cloning vectors and their uses, Rodriguez and Denhardt (Eds.), Stoneham: Butterworth, 494-513, 1988.
Nicolau and Sene, Bioc him. Biophys. Acta, 721:185-190, 1982.
Nicolau et al., Methods Enzymol., 149: 157-176, 1987.
Akashi et al., Nature 404, 193-197, 2000.
Angel et al., Cell, 49:729, 1987b.
Angel et al.,Mol. Cell. Biol., 7:2256, 1987a.
Baichwal & Sugden, In: Gene Transfer, Kucherlapati (Ed), NY, Plenum Press, 117-148, 1986.
Banerji et al., Cell, 27(2 Pt 1):299-308, 1981.
Banerji et al., Cell, 33(3):729-740, 1983.
Bannwarth etal., Genomics 57, 316-317, 1999.
Bannwarth et al., J Biol Chem 273, 1911-1916, 1998.
Benvenisty and Neshif,Proc. Natl.Acad. Sci. USA, 83:9551-9555, 1986.
Berkhout et al., Cell, 59:273-282, 1989.
Bianco and Robey, Development 142, 1023-1027, 2015.
Black et al., Lancet 348, 1535-1541, 1996.
Blanar et al.,EMBOJ, 8:1139, 1989.
Boshart et al., Cell, 41:521, 1985.
Bosze et al., EMBO J, 5(7):1615-1623, 1986.
Braddock et al., Cell, 58:269, 1989.
Campbell et al., J Mal. Biol., 180:1-19, 1984.
Campo et al., Nature, 303:77, 1983.
Celander et al.,J Virology, 62:1314, 1988.
Chan et al., Cell 160, 285-298, 2015.
Chan et al., Nature 457, 490-494, 2009.
Chandler et al., Cell, 33:489, 1983.
Chang et al., Mol. Cell. Biol., 9:2153, 1989.
Chatterjee et al., Proc. Natl. Ac:ad. Sci . USA, 86:9114, 1989.
Chen and Okayama, Mol. Cell Rio!., 7:2745-2752, 1987.
Choi et al., Cell, 53:519, 1988.
Ghosh-Choudhury et al., EMBO J, 6:1733-1739, 1987.
Cohen et al., J Cell. Physiol., 5:75, 1987.
Costa et al.,Mol. Cell. Biol., 8:81, 1988.
Couch et al.,Am. Rev . Resp. Dis ., 88:394-403, 1963.
Coupar et al., Gene, 68: 1-10, 1988.
Cripe et al., EMBO J, 6:3745, 1987.
Cui et al., Nature Medicine 17, 684-691, 2011.
Dandolo et al., J Virology, 47:55-64, 1983.
De Villiers et al., Nature, 312(5991):242-246, 1984.
Deschamps et al., Science, 230:1174-1177, 1985.
Ding and Morrison, Nature 495, 231-235, 2013.
Ding et al., Nature 481, 457-462, 2012.
Dubensky et al., Proc . Natl. Acad. Sci . USA, 81 :7529-7533, 1984.
Edbrooke etal., Mol. Cell. Biol., 9:1908, 1989.
Edlund et al., Science, 230:912-916, 1985.
Egan et al., Histopathology 61, 1168-1173, 2012.
Fechheimer et al., Proc Natl. Acad. Sci . USA, 84:8463-8467, 1987.
Ferkol et al., FASEB J, 7: 1081-1091, 1993.
Fraley et al., Proc Natl. Acad. Sci . USA, 76:3348-3352, 1979.
Friedenstein et al., Cell Tissue Kinet 3, 393-403, 1970.
Friedmann, Science, 244:1275-1281, 1989.
Fujita et al., Cell, 49:357, 1987.
Stuart et al.,Nature, 317:828, 1985.
Sugiyama et al., Immunity 25, 977-988, 2006.
Suire et al., Blood 119, e86-95, 2012.
Takashima et al., Cell 129, 1377-1388, 2007.
Takebe et al.,Mol. Cell. Biol., 8:466, 1988.
Tavernier et al., Nature, 301:634, 1983.
Taylor et al., J Biol. Chem.,264:15160, 1989.
Temin, In: Gene Transfer, Kucherlapati (Ed.), NY, Plenum Press, 149-188, 1986.
Thiesen et al., J Virology, 62:614, 1988.
Top et al., J Infect. Dis., 124:155-160, 1971.
Tronche et al., Mol. Biol. Med., 7: 173, 1990.
Tur-Kaspa et al.,Mol. Cell Biol., 6:716-718, 1986.
Tyndell et al., Nuc. Acids. Res., 9:6231, 1981.
Varmus et al., Cell, 25:23-36, 1981.
Vasseur et al., Proc Natl. Acad. Sci. USA., 77: 1068, 1980.
Wagner et al.,Proc. Natl. Acad. Sci. USA, 87(9):3410-3414, 1990.
Wang, et al., J Bone Miner Res 14, 893-903, 1999.
Weber et al., Cell, 36:983, 1984.
Weinberger et al. Mol. Cell. Biol., 8:988, 1984.
Weinstein et al., J Clin Invest 102, 274-282, 1998.
Wewer et al., J Cell Biol 127, 1767-1775, 1994.
Wong et al., Gene, 10:87-94, 1980.
Worthley et al., Cell J 60, 269-284, 2015.
Wu and Wu, Adv. Drug Delivery Rev., 12:159-167, 1993.
Wu and Wu, Biochemistry, 27:887-892, 1988.
Wu and Wu, J Biol. Chem., 262:4429-4432, 1987.
Yakar and Rosen, Exp Biol Med 228, 245-252, 2003.
Yang et al., Nat Med, 13(4): p. 486-91, 2007.
Yang et al., Proc. Natl. Acad. Sci. USA, 87:9568-9572, 1990.
Yutzey et al. Mol. Cell. Biol., 9:1397, 1989.
Zelenin et al., FEES Lett., 280:94-96, 1991.
Zhou et al., Cell Stem Cell 15, 154-168, 2014.
Oguro et al., Cell Stem Cell 13, 102-116, 2013.
Omatsu et al., Immunity 33, 387-399, 2010.
Omatsu et al., Nature 508, 536-540, 2014.
Ondek et al., RMRO .1., 6: 1017, 1987.
Ono et al., Developmental Cell 29, 330-339, 2014.
Omitz et al., Mol. Cell. Biol., 7:3466, 1987.
Ouma et al., Infection and Immunity 78, 453-460, 2010.
Palmiter et al., Cell, 29:701, 1982.
Palmiter et al., Nature, 300:611, 1982.
Park et al., Cell Stem Cell 10, 259-272, 2012.
Paskind et al., Virology, 67:242-248, 1975.
Pech et al.,Mol. Cell. Biol., 9:396, 1989.
Pelletier and Sonenberg, Nature, 334:320-325, 1988.
Perales et al., Proc. Natl. Acad. Sci. USA, 91(9):4086-4090, 1994.
Perez-Stable and Constantini, Mol. Cell. Biol., 10: 1116, 1990.
Picard and Schaffner, Nature, 307:83, 1984.
Pinkert et al., Genes and Dev., 1:268, 1987.
Ponta et al., Proc. Natl. Acad. Sci. USA, 82: 1020, 1985.
Porton et al., Mol. Cell. Biol., 10: 1076, 1990.
Potter et al.,Proc:. Natl. Ac:ad. Sci. USA, 81:7161-7165, 1984.
Queen and Baltimore, Cell, 35:741, 1983.
Quinn et al., Mol. Cell. Biol., 9:4713, 1989.
Racher et al., Biotech. Techniques, 9: 169-174, 1995.
Ragot et al., Nature, 361:647-650, 1993.
Rahman et al., Bone Research 3, 15005, 2015.
Redondo et al., Science, 247:1225, 1990.
Reisman and Rotter, Mol. Cell. Biol., 9:3571, 1989.
Stratford-Perricaudet et al., Hum. Gene. Ther., 1:241-256, 1990.
Renan,Radiother. Oneal., 19:197-218, 1990.
Resendez Jr. etal.,Mol. Cell. Biol., 8:4579, 1988.
Rich et al., Hum. Gene Ther., 4:461-476, 1993.
Ridgeway, In: Vectors: A survey of molecular cloning vectors and their uses, Stoneham: Butterworth, 467-492, 1988.
Ripe et al., Mol. Cell. Biol., 9:2224, 1989.
Rippe et al., Mol. Cell Biol., 10:689-695, 1990.
Rittling et al., Nuc. Acids Res., 17: 1619, 1989.
Rodan and Martin, Science 289, 1508-1514, 2000.
Rosen et al., Cell, 41:813, 1988.
Rosenfeld et al., Cell, 68:143-155,1992.
Rosenfeld et al., Science, 252:431-434, 1991.
Roux et al., Proc. Natl. Acad. Sci. USA, 86:9079-9083, 1989.
Sacchetti et al., Cell 131, 324-336, 2007.
Sakai et al., Genes and Dev., 2:1144, 1988.

(56) References Cited

OTHER PUBLICATIONS

Satake et al., J Virology, 62:970, 1988.
Schaffner et al., J Mol. Biol., 201:81, 1988.
Searle et al., Mol. Cell. Biol., 5:1480, 1985.
Sherman et al., Mol. Cell. Biol., 9:50, 1989.
Spalholz et al., Cell, 42:183, 1985.
Stephens and Hentschel, Biochem. J, 248: 1, 1987.
Gilles et al., Cell, 33:717, 1983.
Gloss et al., EMBO J, 6:3735, 1987.
Godbout et al., Mal. Cell. Biol., 8: 1169, 1988.
Gomez-Foix et al., J Biol. Chem., 267:25129-25134, 1992.
Goodbourn and Maniatis, Proc. Natl. Acad. Sci. USA. 85:1447, 1988.
Goodbourn et al., Cell, 45:601, 1986.
Gopal, Mol. Cell Biol., 5:1188-1190, 1985.
Gopal-Srivastava et al., J Mal. Cell. Rial., 15(12):7081-90, 1995.
Graham and Prevec, In: Methods in Molecular Biology: Gene Transfer and Expression Protocol, Murray (Ed.), Humana Press, Clifton, NJ, 7:109-128, 1991.
Graham and van der Eb, Virology, 52:456-467, 1973.
Graham, et al. ,J Gen. Viral., 36:59-72, 1977.
Greenbaum et al., Nature 495, 227-230, 2013.
Greene et al., Immunology Today, I 0:272, 1989.
Klamut et al.,Mol. Cell. Biol., 10:193, 1990.
Harada and Rodan, Nature 423, 349-355, 2003.
Harland and Weintraub, J Cell Biol., 101: 1094-1099, 1985.
Hen et al., Nature, 321:249, 1986.
Hensel et al., Lymp hokine Res., 8:347, 1989. Abstract only.
Hermonat and Muzycska, Proc. Nat'! Ac:ad. Sci. USA, 81:6466-6470, 1984.
Herr and Clarke, Cell, 45:461, 1986.
Hersdorffer et al.,DNA Cell Biol., 9:713-723, 1990.
Herz and Gerard, Proc. Nat'!. Acad. Sci. USA 90:2812-2816, 1993.
Hiraoka et al.,Hematology J. 2, 307-315, 2001.
Hiraoka et al., Proceedings of the National Academy of Sciences USA 94, 7577-7582, 1997.
Hiraoka et al., The Hematology Journal 2, 307-315, 2001.
Hirochika et al.,J Viral., 61:2599, 1987.
Holbrook et al., Virology, 157:211, 1987.
Horwich et al., J Viral., 64:642-650, 1990.
Huang et al., Cell, 27:245, 1981.
Hug et al., Mal. Cell. Biol., 8:3065, 1988.
Hwang et al., Mal. Cell. Biol., IO: 585, 1990.
Iba et al., Molecular Cellular Biology 21, 7817-7825, 2001.
Imagawa et al., Cell, 51:251, 1987.
Imler et al.,Mol. Cell. Biol .. 7:2558, 1987.
Ito et al., Bone Marrow Transplantation 32, 391-398, 2003.
Jakobovits et al., Mal. Cell. Biol., 8:2555, 1988.
Jaynes et al.,Mol. Cell. Biol., 8:62, 1988.
Johnson et al.,Mol. Cell. Biol., 9:3393, 1989.
Jones and Shenk, Cell, 13:181-188, 1978.
Kaneda et al., Science, 243:375-378, 1989.
Karin et al., Mal. Cell. Rial., 7:606, 1987.
Karlsson et al., JiMBO J., 5:2377-2385, 1986.
Katinka et al., Cell, 20:393, 1980.
Kato et al., J Biol Chem., 266(6):3361-3364, 1991.
Kawamoto et al.,Mol. Cell. Biol., 8:267, 1988.
Keller et al., Injection and Immunity 77, 3864-3871, 2009.
Kiel et al., Blood 111, 4413-4414, 2008.
Kiel et al., Cell 121, 1109-1121, 2005.
Kiledjian et al.,Mol. Cell. Biol., 8:145, 1988.

\* cited by examiner

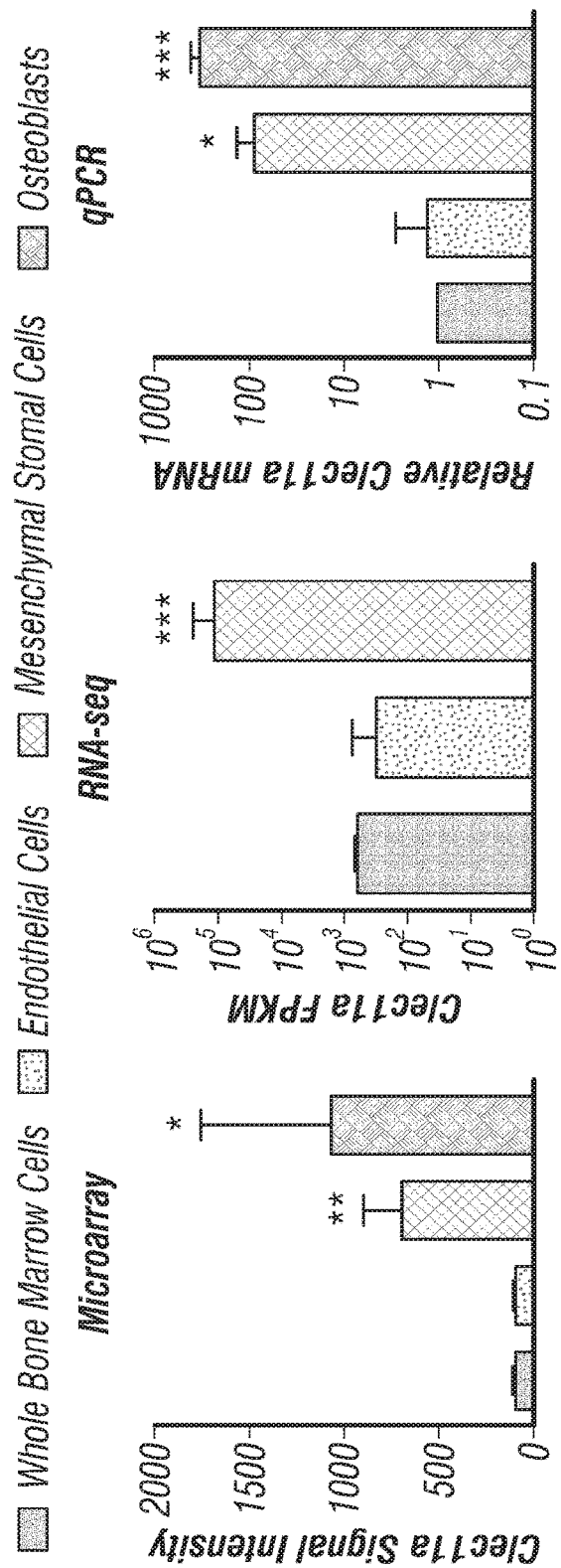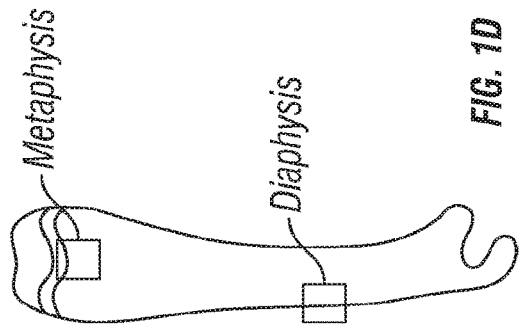

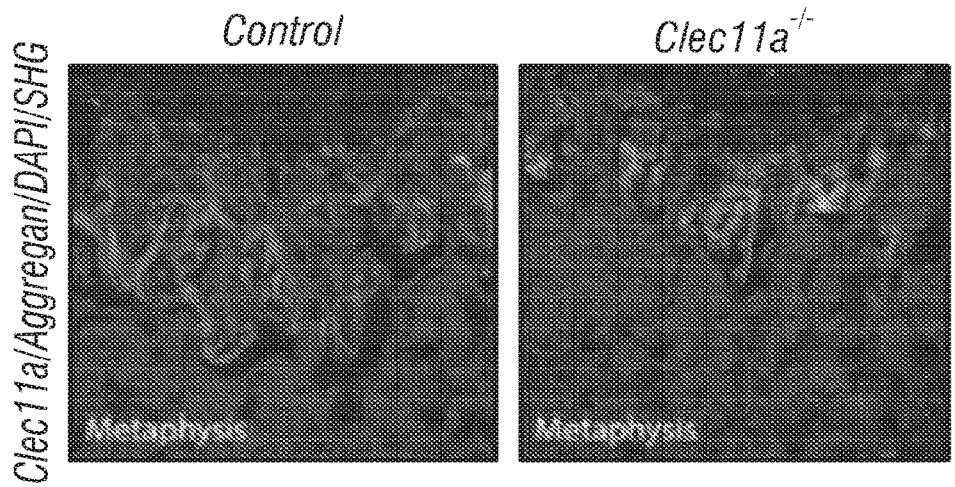
FIG. 1E
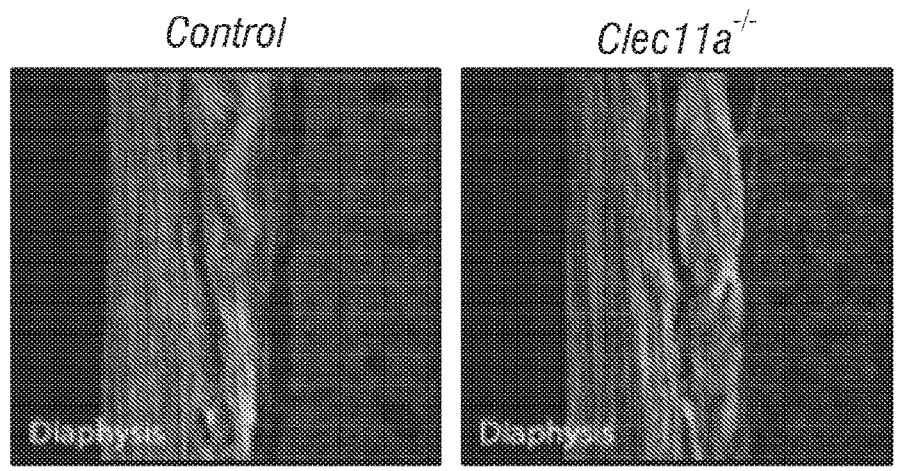
FIG. 1F
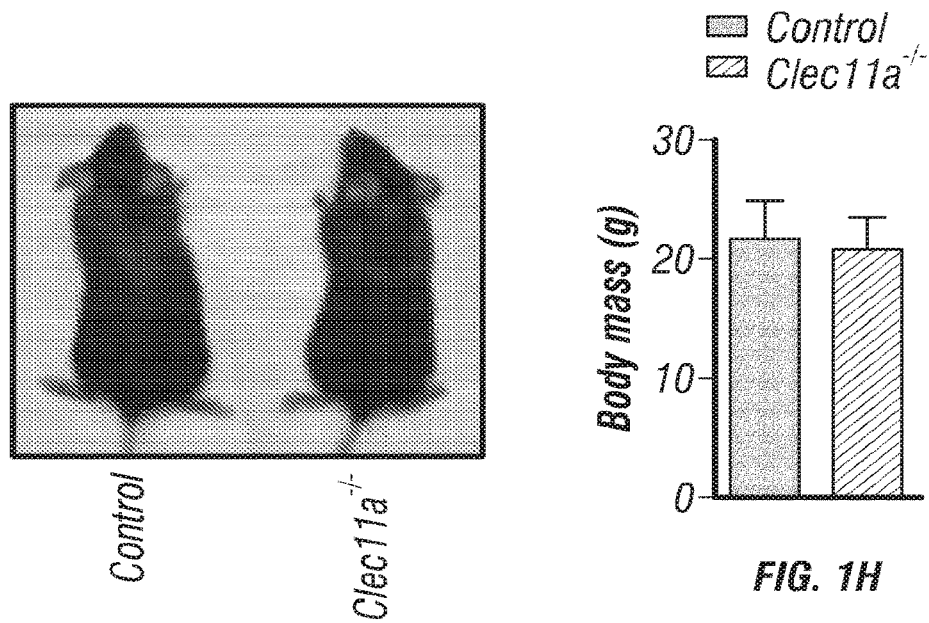
FIG. 1G
FIG. 1H

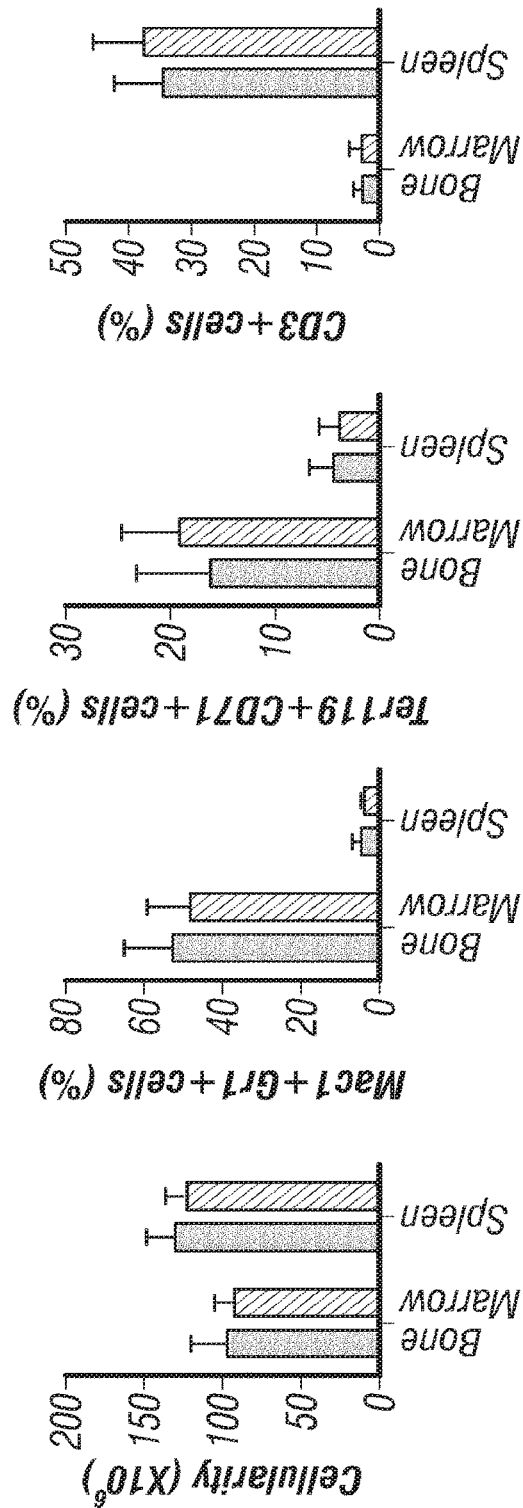
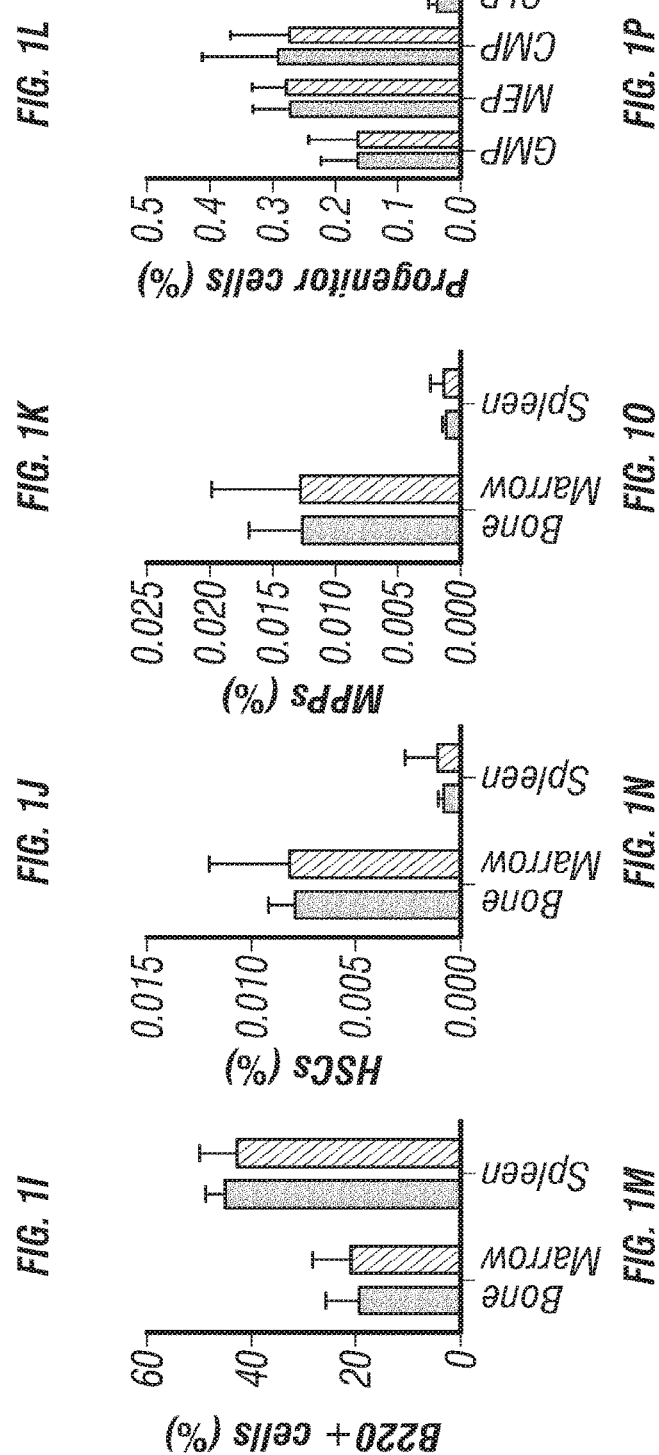

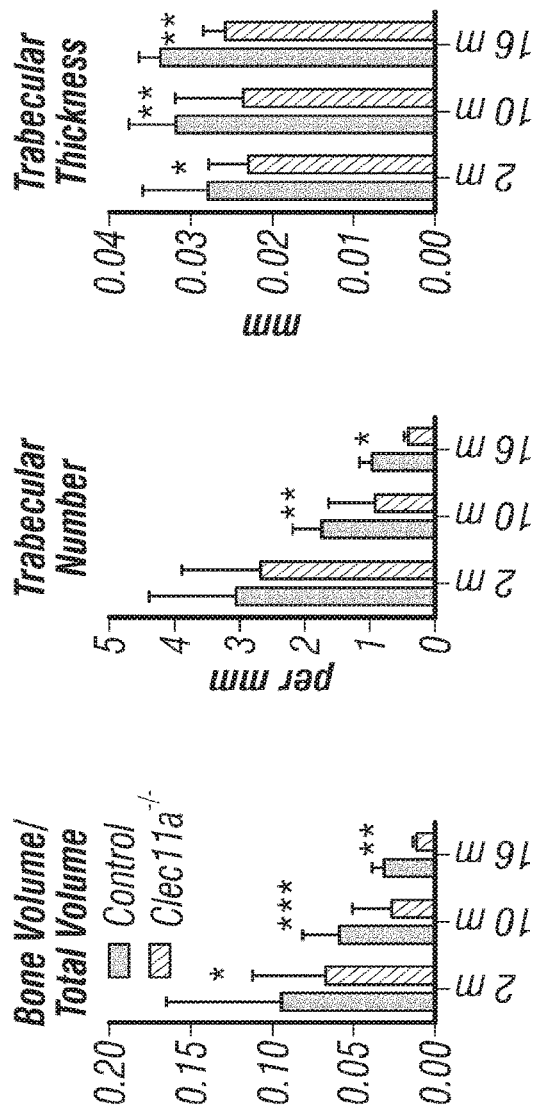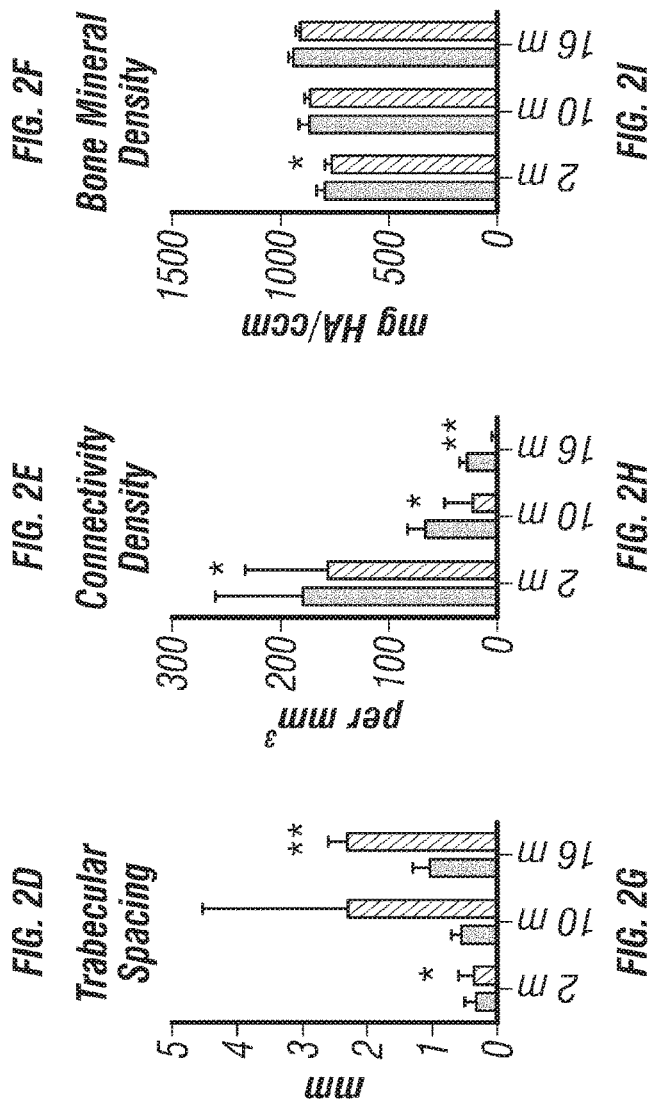

Alkaline Phosphatase Staining

Alizarin Red Staining

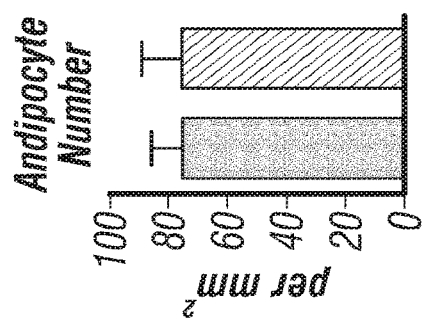
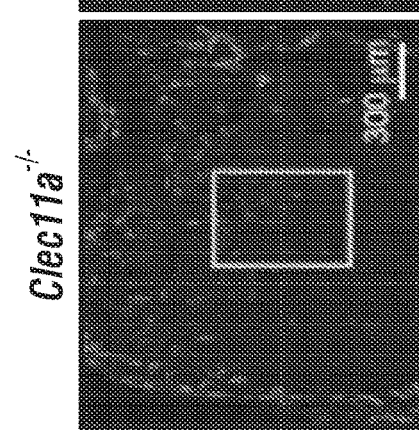
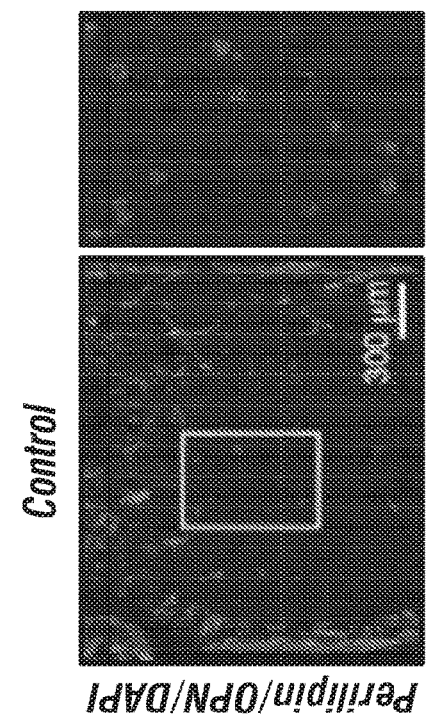
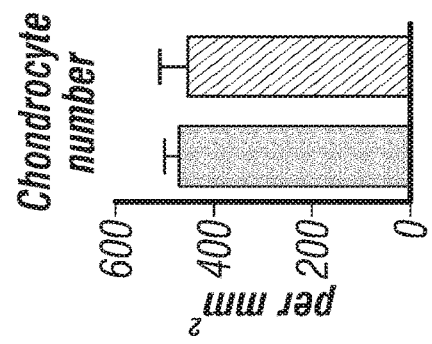
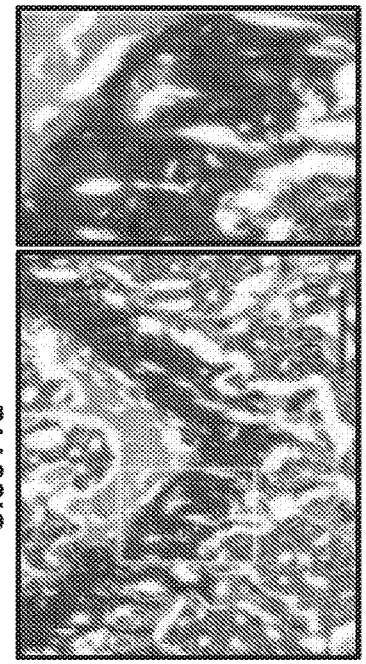
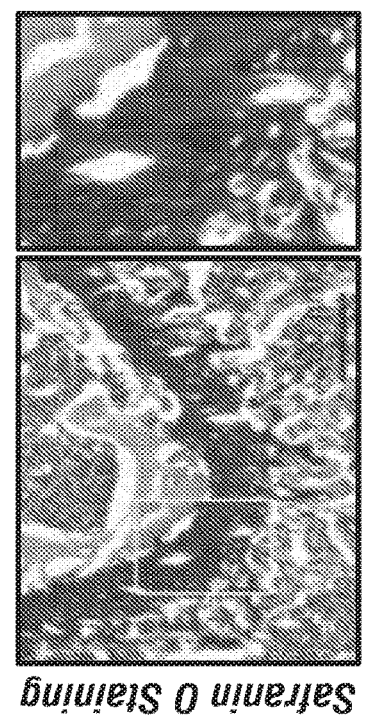
FIG. 3I  FIG. 3J  FIG. 3K
FIG. 3L  FIG. 3M  FIG. 3N

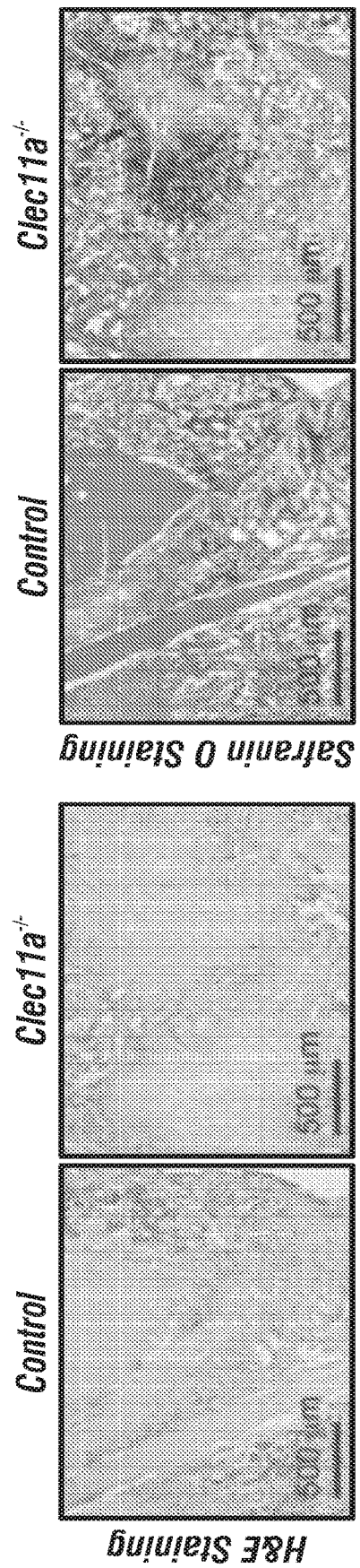
FIG. 4A — H&E Staining (Control, Clec11a−/−)
FIG. 4B — Safranin O Staining (Control, Clec11a−/−)
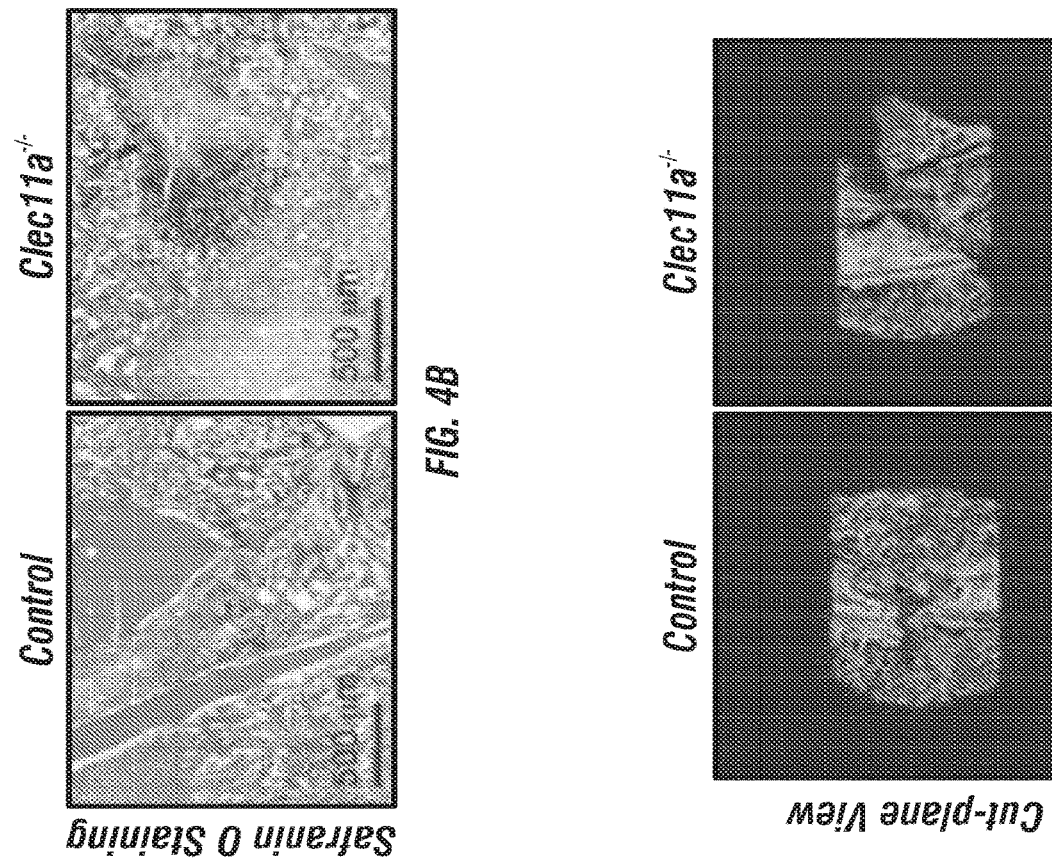
FIG. 4C — 3D Overview (Control, Clec11a−/−)
FIG. 4D — Cut-plane View (Control, Clec11a−/−)

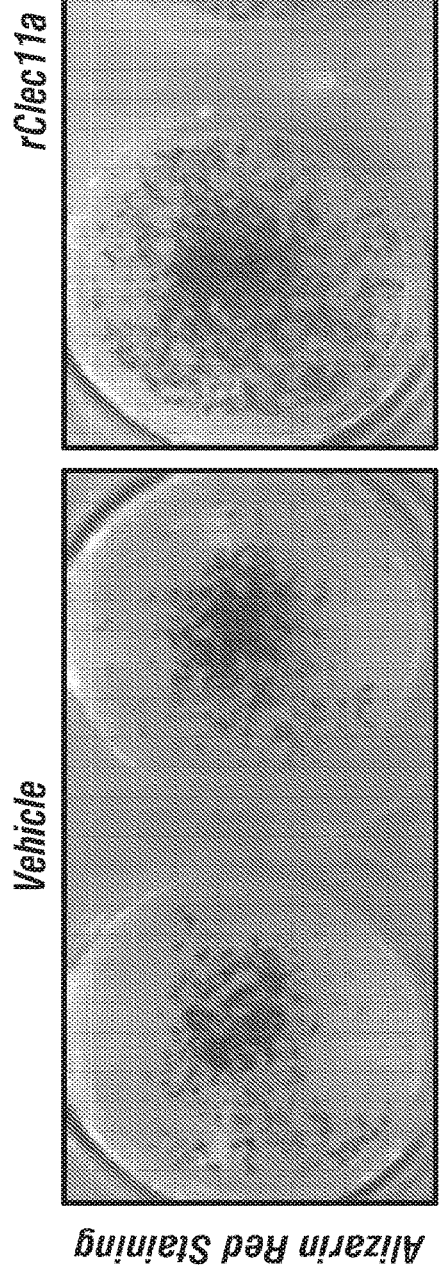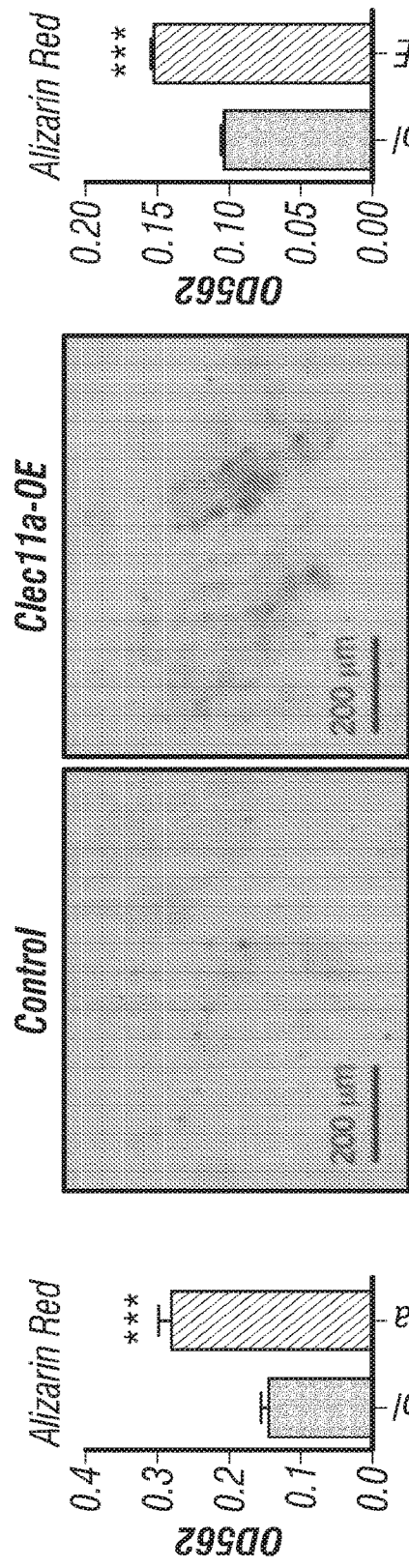
FIG. 5A
FIG. 5B
FIG. 5C
FIG. 5D

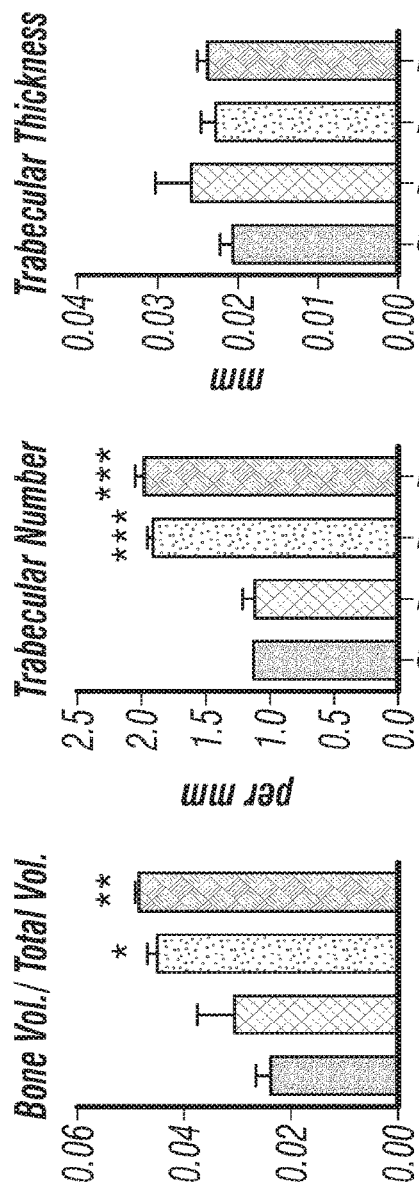
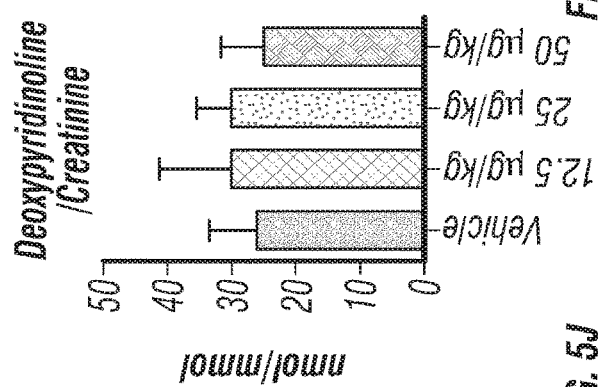
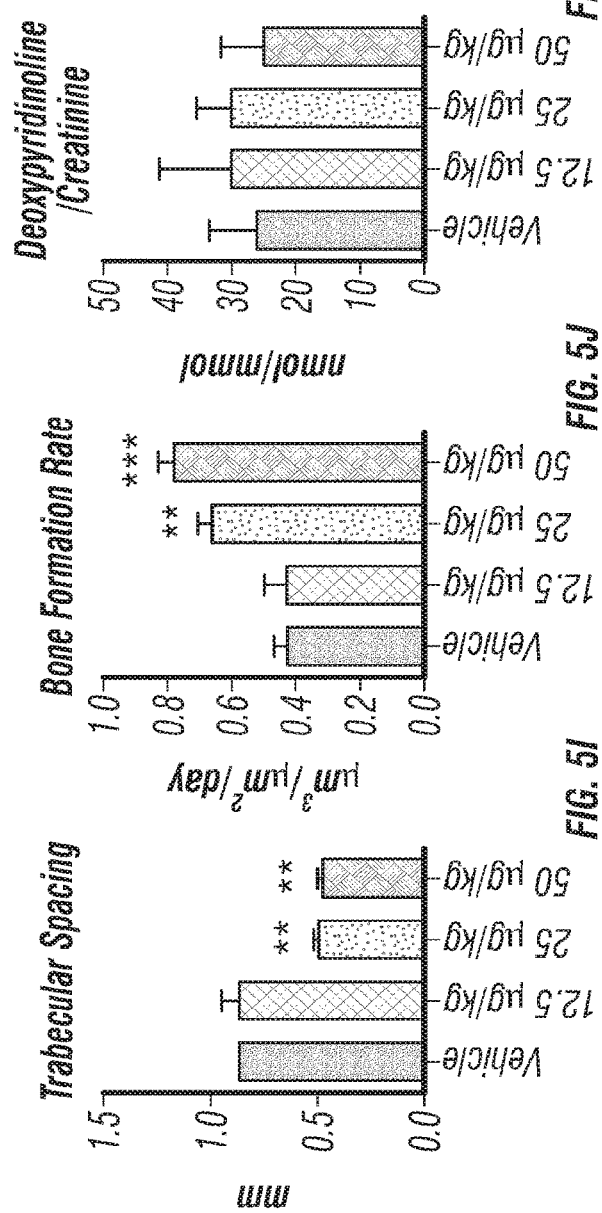

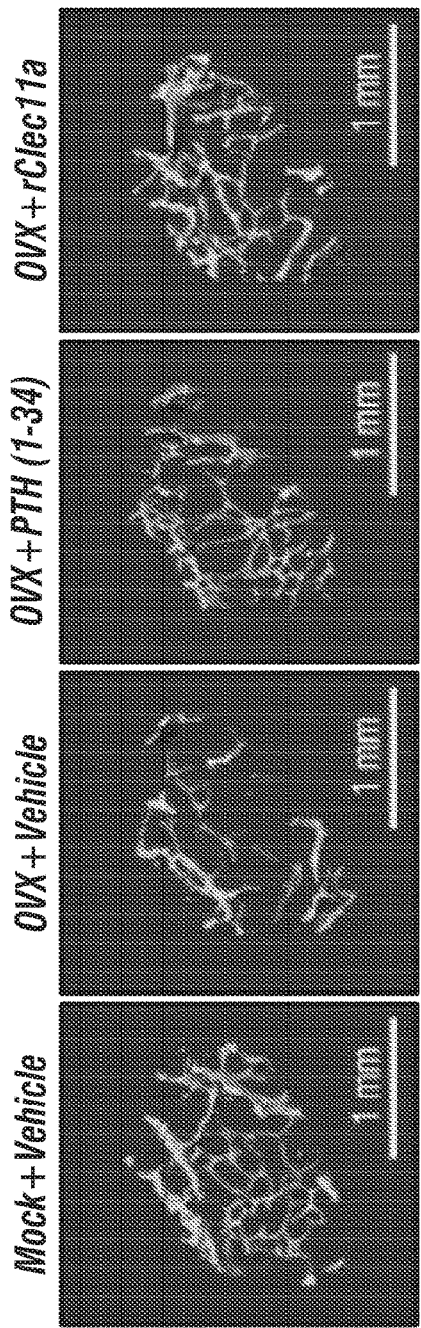
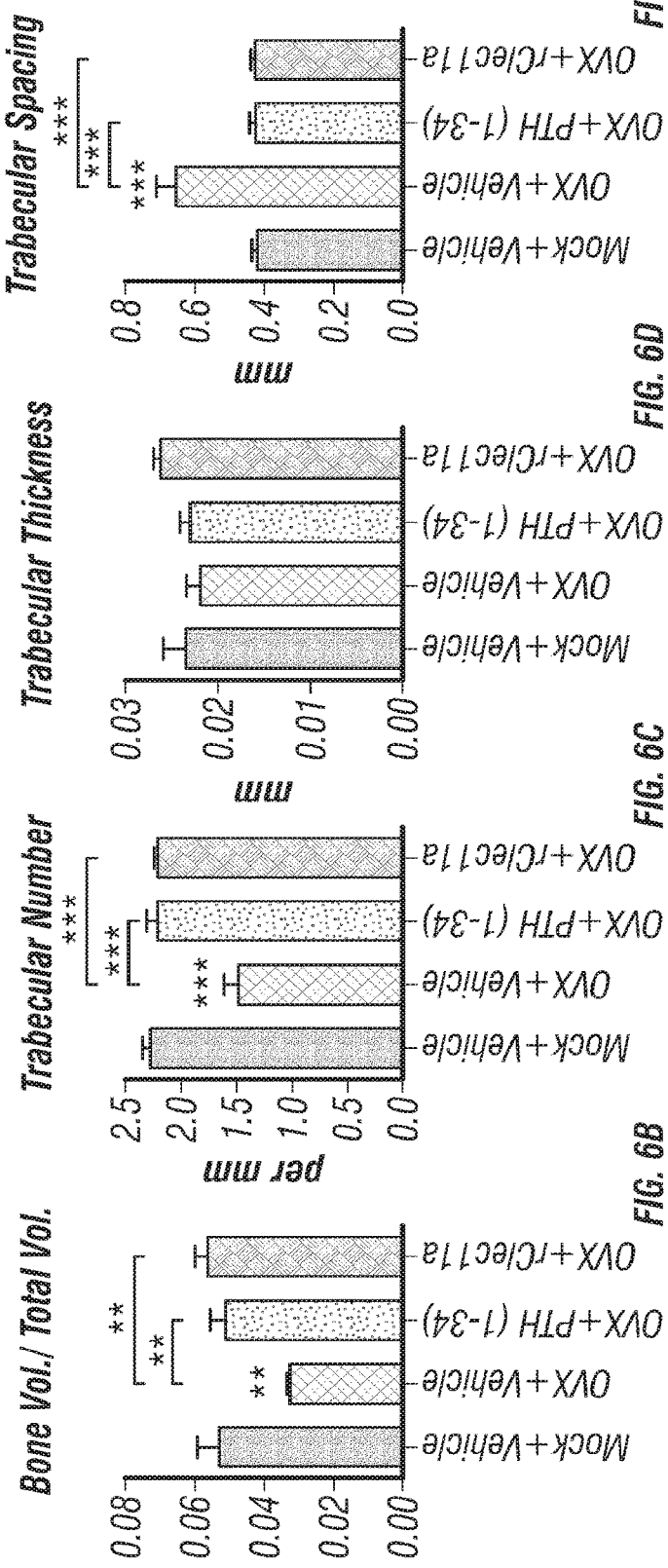

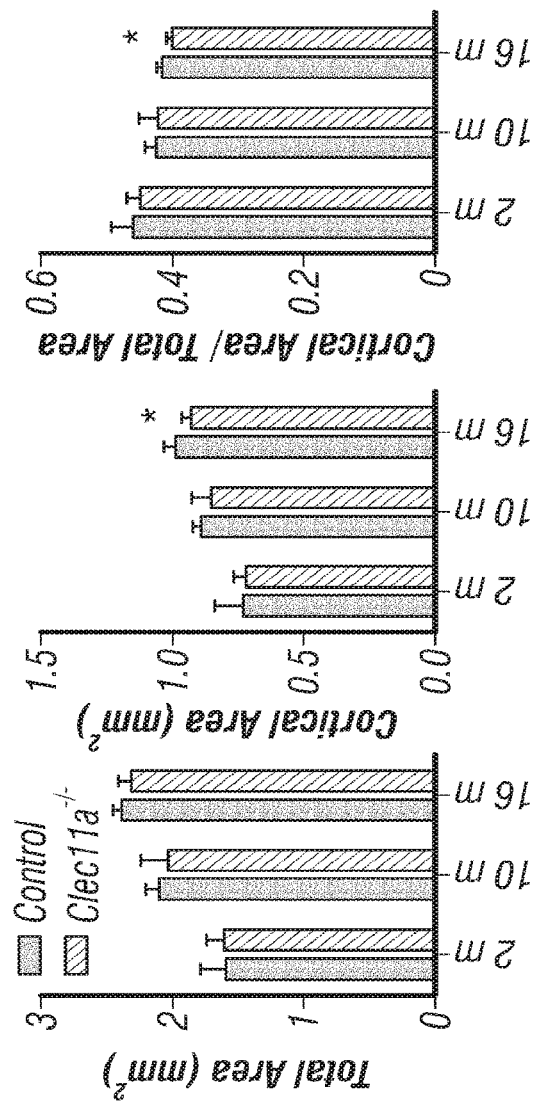
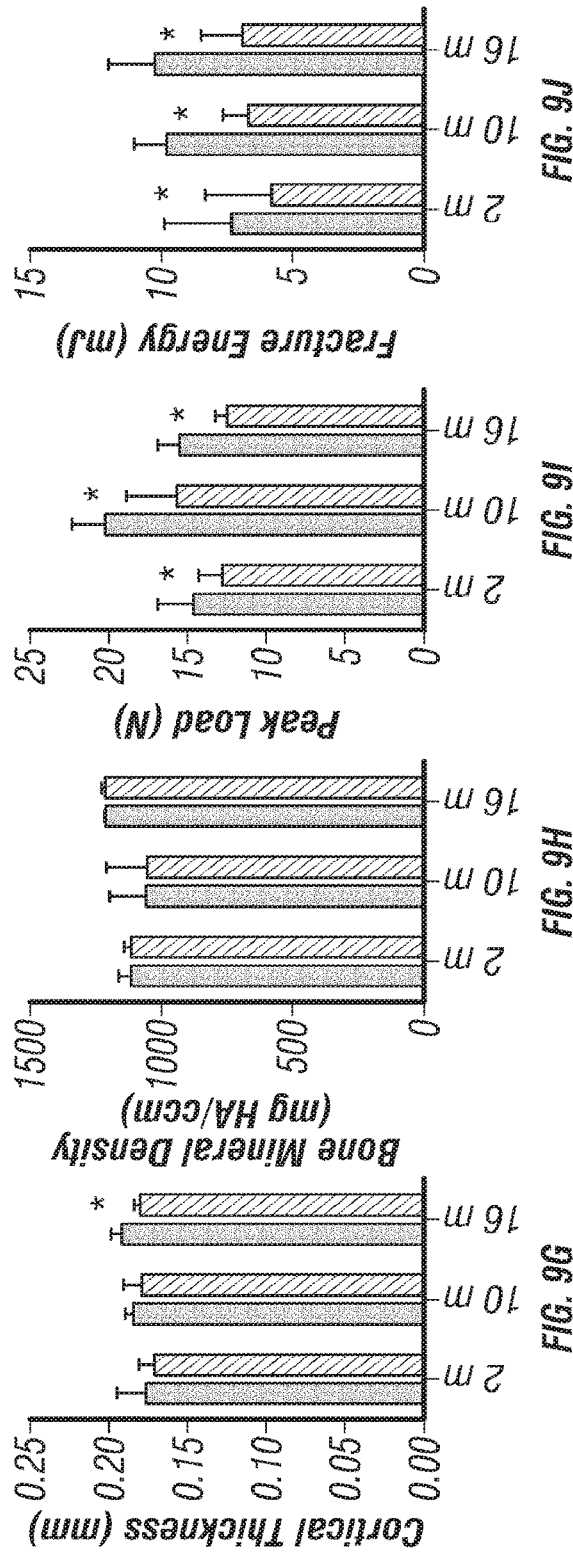

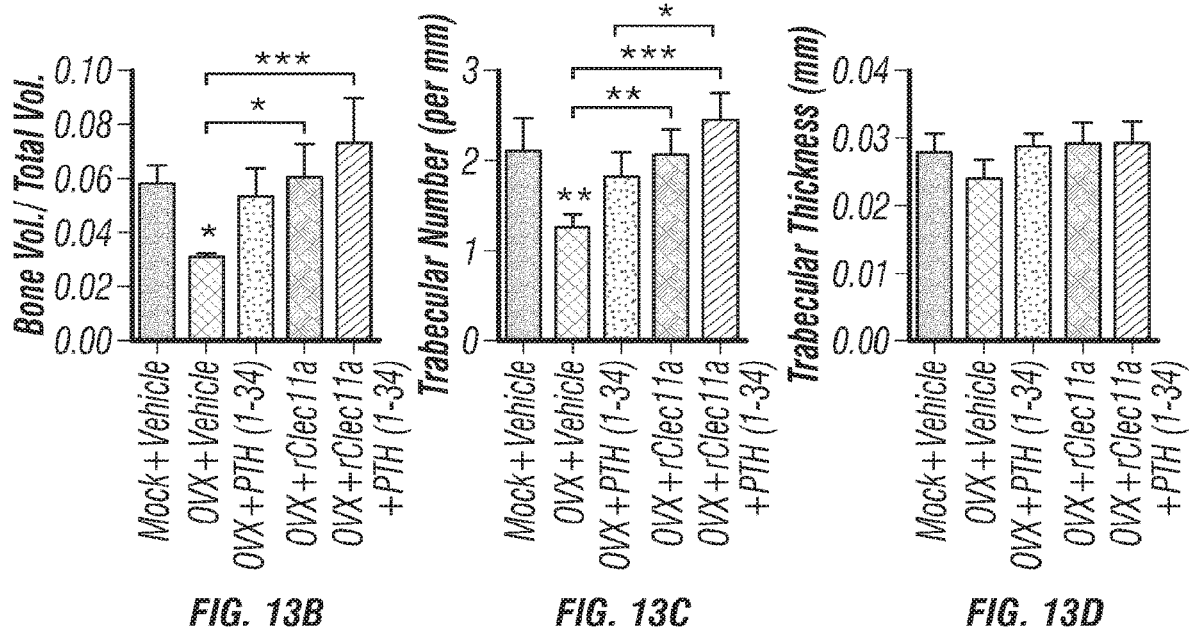
FIG. 13B  FIG. 13C  FIG. 13D
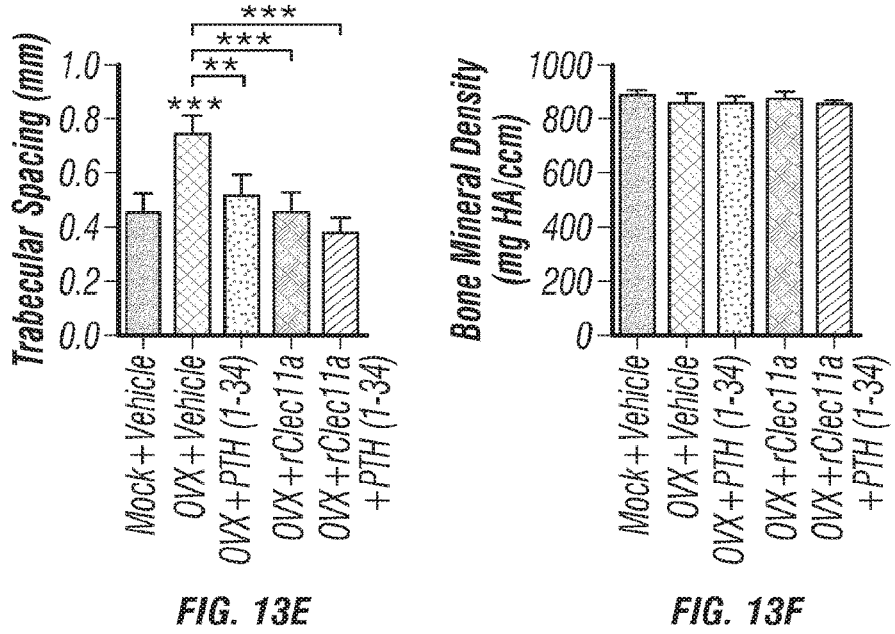
FIG. 13E  FIG. 13F

*Vehicle*

*rhClec11a*

CLEC11A IS A BONE GROWTH AGENT

This application is a continuation of U.S. application Ser. No. 15/567,762, filed Oct. 19, 2017, now U.S. Pat. No. 11,285,190, issued Mar. 29, 2022, which is a National Stage Entry of PCT/US2016/28066, filed Apr. 18, 2016, which claims benefit of priority to U.S. Provisional Application Ser. No. 62/150,071 filed Apr. 20, 2015, U.S. Provisional Application Ser. No. 62/275,570 filed Jan. 6, 2016, and U.S. Provisional Application Ser. No. 62/293,373 filed Feb. 10, 2016, the entire contents of which are hereby incorporated by reference.

BACKGROUND

1. Field

The present disclosure relates generally to the fields of medicine, developmental biology and molecular biology. More particularly, it concerns the role of CLEC11a in the generation of bone, and its use as an agent to treat bone disease.

2. Description of Related Art

Mesenchymal stem cells (MSCs), perhaps better known as skeletal stem cells (SSCs) in adult bone marrow (Bianco and Robey, 2015), are multipotent progenitors that form fibroblast colonies in culture (CFU-F) (Friedenstein et al., 1970). These cells have the potential to give rise to stromal cells, osteoblasts, chondrocytes, and adipocytes. Nonetheless, they are not necessarily fated to form all such derivatives in vivo. Fate mapping studies show there are multiple lineages of temporally, and perhaps spatially, distinct mesenchymal progenitors in skeletal tissues that contribute to different mesenchymal derivatives at different developmental stages (Liu et al., 2013; Maes et al., 2010; Mizoguchi et al., 2014; Park et al., 2012; Takashima et al., 2007; Worthley et al., 2015; Zhou et al., 2014).

During fetal development, Osterix$^+$ cells in the perichondrium give rise to osteoblasts and osteocytes in developing bones (Liu et al., 2013; Maes et al., 2010; Mizoguchi et al., 2014). In early postnatal bone marrow, Osterix$^+$ cells form stromal cells that persist throughout adult life in the bone marrow, including Leptin Receptor (LepR)-expressing stromal cells that are the major source of bone and adipocytes in adult mice (Mizoguchi et al., 2014; Zhou et al., 2014). However, within adult bone marrow, Osterix marks only short-lived osteogenic progenitors (Mizoguchi et al., 2014; Park et al., 2012), suggesting that Osterix expression is extinguished within LepR$^+$ SSCs in adult bone marrow. Osterix$^+$ osteogenic progenitors also persist periosteally, on the outer surface of adult bones, where they contribute to bone repair after bone injuries (Maes et al., 2010).

Neural crest-derived cells transiently give rise to mesenchymal progenitors and stromal cells in postnatal bone marrow, though these cells are replaced by non-neural crest-derived cells in adult bone marrow (Leucht et al., 2008; Mabuchi and Okano, 2015; Takashima et al., 2007; Zhou et al., 2014). This may explain why the contribution of Nestin-CreER-expressing cells to stroma in postnatal bone marrow (Mendez-Ferrer et al., 2010) is short-lived (Ono et al., 2014). In adult bone marrow, Nestin-CreER marks only rare stromal cells, osteoblasts, and CFU-F (Worthley et al., 2015; Zhou et al., 2014). A distinct Gremlin-1-CreER-expressing lineage near the growth plate of long bones generates osteoblasts, chondrocytes, and stromal cells during development, and to a lesser extent during adulthood (Worthley et al., 2015).

Most CFU-F in adult bone marrow arise from LepR-expressing stromal cells (Zhou et al., 2014). Niches that support hematopoiesis arise through endochondral ossification (Chan et al., 2009) and LepR$^+$ bone marrow cells can form ossicles that support hematopoiesis in vivo (Zhou et al., 2014). LepR$^+$ cells arise postnatally in the bone marrow and make little contribution to the skeleton during development, but are the major source of bone and adipocytes during adulthood (Zhou et al., 2014). Bone marrow SSCs can also be identified based on the expression of CD146, CD271, VCAM-1, and Thy-1 in humans or PDGFRα, AlphaV integrin, and/or CD105 in mice, as well as the lack of expression of hematopoietic and endothelial markers (Chan et al., 2009; Chan et al., 2015; Mabuchi et al., 2013; Morikawa et al., 2009; Omatsu et al., 2010; Park et al., 2012; Sacchetti et al., 2007; Zhou et al., 2014). LepR$^+$ cells are a key source of growth factors that maintain hematopoietic stem cells (HSCs) in the bone marrow, including SCF and CXCL12 (Ding and Morrison, 2013; Ding et al., 2012; Oguro et al., 2013). Bone marrow stromal cells that are highly enriched for CFU-F and LepR$^+$ cells have also been identified based on expression of high levels of Scf (Zhou et al., 2014) or Cxcl12 (Ding and Morrison, 2013; Omatsu et al., 2014; Sugiyama et al., 2006) as well as low levels of the Nestin-GFP transgene (Kunisaki et al., 2013; Mendez-Ferrer et al., 2010), PDGFR expression (Morikawa et al., 2009; Zhou et al., 2014), or Prx-1-Cre recombination (Greenbaum et al., 2013; Zhou et al., 2014).

Multiple growth factor families have been shown to promote osteogenesis including Wnts (Cui et al., 2011; Krishnan et al., 2006), BMPs (Nakamura et al., 2007; Rahman et al., 2015), and IGFs (Yakar and Rosen, 2003). However, these factors have broad effects on many tissues, complicating their systemic administration to promote osteogenesis. Sclerostin, a Wnt signaling inhibitor that is locally produced by the osteocytes, negatively regulates osteoblast activity and bone formation (Li et al., 2005). Consistent with this, sclerostin inhibitors promote bone formation and increase bone mineral density (McClung et al., 2014). A recent study demonstrated that factors secreted by bone marrow SSCs strongly promote osteogenesis (Chan et al., 2015), though the full repertoire of such factors remains to be identified.

Osteoporosis is a progressive bone disease characterized by decreased bone mass and increased fracture risk (Harada and Rodan, 2003). Aging, estrogen insufficiency, long-term glucocorticoid use, and mechanical unloading all contribute to the development of osteoporosis (Harada and Rodan, 2003). Most existing osteoporosis therapies are antiresorptive agents, such as bisphosphonates (Black et al., 1996; Liberman et al., 1995) and estrogens (Michaelsson et al., 1998), which reduce the rate of bone loss but do not promote new bone formation. The only FDA-approved anabolic agent that increases bone formation is Teriparatide, a small peptide derived from human parathyroid hormone (PTH amino acids 1-34)) (Neer et al., 2001). Nonetheless, some patients cannot take Teriparatide (Kraenzlin and Meier, 2011) and its use is limited to two years because of a potential risk of osteosarcoma (Neer et al., 2001). Thus, there remains a need for therapies that address bone disease, and in particular for improved methods of stimulating bone formation and increasing bone strength in vivo to treat bone disease and injury, including cancer.

SUMMARY

Thus, in accordance with the present disclosure, there is provided a method of increasing bone density, strength, volume or mineralization in a subject in need thereof comprising providing to the subject CLEC11a or an agonist or mimic thereof. Also provided is a method of treating a bone trauma, disease or disorder in a subject comprising providing to the subject CLEC11a or an agonist or mimic thereof. Also provided is a method of reversing bone loss in a subject comprising providing to the subject CLEC11a or an agonist or mimic thereof. Also provided is a method of promoting bone formation or osteogenesis in a subject in need thereof comprising providing to the subject CLEC11a or an agonist or mimic thereof. The osteogenesis may be promoted by mesenchymal stem cells.

The method above may be applied to a subject suffering from osteopenia, osteoporosis, bone trauma, fracture, or is in need of spinal fusion. Providing may comprise administering CLEC11a, agonist or mimic to the subject, such as CLEC11a administered in a lipid vehicle, hydrogel or nanoparticle. Providing may comprise administering a CLEC11a agonist or mimic, such as a protein agonist or mimic, a nucleic acid agonist or mimic or a small molecule agonist or mimic. Providing may comprise administering a CLEC11a expression cassette to the subject, such as where the expression cassette is comprised in a replicable vector, including a viral vector (e.g., an adenoviral vector or retroviral vector) or a non-viral vector. The viral or non-viral vector may be delivered in or on a lipid delivery vehicle or a nanoparticle. The expression cassette may comprise a constitutive promoter, a global promoter or a bone specific promoter.

The CLEC11a or agonist or mimic thereof may be administered more than once, such as 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times. The CLEC11a or agonist or mimic thereof may be delivered daily, weekly or monthly. The CLEC11a or agonist or mimic thereof is may be administered intravenously, orally, topically, subcutaneously or intra-articularly. The CLEC11a or an agonist or mimic thereof may be administered systemically. The CLEC11a or agonist or mimic thereof is administered local to a site of bone trauma, disease or disorder.

The method may further comprise administering CLEC11a or an agonist or mimic thereof in combination with a second bone therapy, such as an anti-resportive agent (e.g., a bisphosphonate, calcitonin, denosumab, estrogen or an estrogen agonists/antagonist), or an anabolic agent (e.g., a sclerostin inhibitor or a Parathyroid Hormone (PTH) analog). The CLEC11a or CLEC11a agonist or mimic may be embedded in a slow release delivery vehicle, and/or a polymeric delivery vehicle. The CLEC11a or CLEC11a agonist or mimic may be administered locally (such as embedded in a slow release locally deliver vehicle for spinal fusion, or fracture repair) or it may be administered systemically (such as to systemically promote hone formation in the context of osteoporosis).

The bone trauma, disease or disorder may be a fracture, osteoporosis, osteopenia, primary or metastatic cancer, periodontal disease, or transplant/reconstructive surgery, such as spinal fusion. The subject may be a human, a non-human mammal, or an elderly human.

Also provided is a method of inhibiting pathologic bone formation comprising administering to a subject in need thereof a CLEC11a antagonist. The subject may exhibit a specific cite of ectopic bone formation, or exhibit systemic bone formation. The pathologic bone formation may be a result of inflammation, or as a result of trauma or burn. The CLEC11a antagonist may be an siRNA, an antibody, an antisense molecule, a decoy receptor, a small molecule inhibitor, an inhibitory CLEC11a fragment, or a decoy receptor.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-T. Clec11a deficient mice were grossly developmentally normal and had normal hematopoiesis. (FIGS. 1A-C) Clec11a mRNA level analysis by microarray, RNA-seq and qPCR. Whole bone marrow cells, VE-Cadherin$^+$ bone marrow endothelial cells, bone marrow mesenchymal stromal cells (PDGFRα$^+$CD45$^-$Ter119$^-$CD31$^-$ or Scf-GFP$^+$CD45$^-$Ter119$^-$CD31$^-$) and Col2.3-GFP$^+$CD45$^-$Ter119$^-$CD31$^-$ osteoblasts were sorted from enzymatically dissociated femur bone marrow of 2 month-old mice, followed by microarray (FIG. 1A; left to right: whole bone marrow cells; endothelial cells; mesenchymal stromal cells; osteoblasts), RNA-seq (FIG. 1B; left to right: whole bone marrow cells; endothelial cells; mesenchymal stromal cells) and qPCR (FIG. 1C; left to right: whole bone marrow cells; endothelial cells; mesenchymal stromal cells; osteoblasts) analysis. The statistical significance of differences in FIGS. 1A-C was assessed using one-way ANOVAs with Dunnett's multiple comparisons tests (n=3 mice per genotype, total, from three independent experiments). (FIG. 1D) Diagram of the position of images from femur sections. (FIGS. 1E and 1F) Confocal analysis of anti-Clec11a antibody staining (green) in the femur metaphysis (FIG. 1E) and diaphysis (FIG. 1F) of Clec11a$^{-/-}$ and sex-matched littermate control mice. Growth plate chondrocytes were marked by aggrecan staining. Bone was imaged by second harmonic generation (SHG) (n=3 mice per genotype, total, from three independent experiments). (FIG. 1G) Representative images of 2 month-old control and Clec11a$^{-/-}$ mice. (FIG. 1H) Body mass of 2 month-old mice (n=8 mice per genotype, total, from six independent experiments for all data in FIGS.

1H-P). (FIG. 1I) Cellularity of the bone marrow and spleen. (FIGS. 1J-P) Flow cytometric analysis of the frequencies of myeloid cells (FIG. 1J), erythroid progenitors (FIG. 1K), T cells (FIG. 1L), B cells (M), hematopoietic stem cells (FIG. 1N), multipotent progenitors (FIG. 1O) and restricted progenitors (FIG. 1P) in the bone marrow and spleen of Clec11a$^{-/-}$ mice and sex-matched littermate controls. The statistical significance of differences among genotypes in FIGS. 1H-P was assessed using two-tailed Student's t tests. (FIGS. 1Q-T; circle=control; square=Clec11a$^{-/-}$) Competitive reconstitution analysis of irradiated mice transplanted with 300,000 donor bone marrow cells from Clec11a$^{-/-}$ or littermate control mice along with 300,000 recipient bone marrow cells. All mice were long-term multilineage reconstituted by donor cells (FIG. 1Q), including CD3$^+$ T cells (FIG. 1R), B220$^+$ B cells (FIG. 1S) and Mac1$^+$Gr-1$^+$ myeloid cells (FIG. 1T) (n=10 recipients per genotype, total, from two independent experiments). The statistical significance of differences among genotypes was assessed using repeated measures two-way ANOVAs with Sidak's multiple comparisons tests. Data represent mean±SD: *P<0.05, P<0.01, *P<0.001.

(FIGS. 2A-C) MicroCT images of trabecular bone in the distal femur metaphysis of 2 month-old (FIG. 2A), 10 month-old (FIG. 2B) and 16 month-old (FIG. 2C) Clec11a$^{-/-}$ mice and sex-matched littermate controls. (FIGS. 1D-1) MicroCT analysis of trabecular bone parameters (trabecular bone volume/total volume (FIG. 2D), trabecular number (FIG. 2E), trabecular thickness (FIG. 2F), trabecular spacing (FIG. 2G), connectivity density (FIG. 2H) and bone mineral density (FIG. 2I)) in the distal femur metaphysis of 2, 10 and 16 month-old Clec11a$^{-/-}$ mice and sex-matched littermate controls (n=4-9 mice per genotype, total, from at least four independent experiments). (FIG. 2V) Bone resorption analysis by measuring the deoxypyridinoline/creatinine ratio in the urine (n=4 mice per genotype, total, from four independent experiments). The statistical significance of differences among genotypes was assessed using two-tailed Student's paired t tests. Data represent mean±SD: *P<0.05, P<0.01, *P<0.001.

FIGS. 3A-N. Clec11a is necessary for osteogenic differentiation. (FIGS. 3A-D) Osteogenic differentiation in culture of bone marrow stromal cells from femur bone marrow of Clec11$^{-/-}$ mice and sex-matched littermate controls. Alkaline phosphatase staining and alizarin red staining were performed after 7 days (FIG. 3A and FIG. 3B) and 14 days (FIG. 3C and FIG. 3D) to quantify t osteoblast differentiation and mineralization (n=3 independent experiments). (FIGS. 3I-K) Representative perilipin and osteopontin (OPN) staining in femur sections of 2 month-old Clec11$^{-/-}$ mice and sex-matched littermate controls (FIG. 3I and FIG. 3J) with the number of adipocytes per mm$^2$ (FIG. 3K) (n=3 mice per genotype, total, from three independent experiments). (FIGS. 3L-N) Representative safranin O/fast green staining in femur sections of 2 month-old Clec11a$^{-/-}$ mice and sex-matched littermate controls (FIG. 3L and FIG. 3M) with the number of chondrocytes per mm$^2$ (FIG. 3N) (n=3 mice per genotype, total, from three independent experiments). The statistical significance of differences among genotypes was assessed using two-tailed Student's t tests. Data represent mean±SD: ***P<0.001.

FIGS. 4A-J. Clec11a is necessary for bone regeneration and fracture healing. (FIGS. 4A-B) Hematoxylin & eosin (FIG. 4A) and safranin O (FIG. 4B) staining of the callus around the fracture site two weeks after bone fracture. (FIGS. 4C-D) Representative microCT snapshot images of the callus (FIG. 4C) and cut-plane images around the fracture site (FIG. 4D) two weeks after bone fracture. (FIGS. 4E-J) MicroCT analysis of trabecular bone volume/total volume (FIG. 4E), trabecular number (FIG. 4F), trabecular thickness (FIG. 4G), connectivity density (FIG. 4H), trabecular spacing (FIG. 4I) and bone mineral density (FIG. 4J) in the callus two weeks after bone fracture (n=3 mice per genotype, total, from three independent experiments). The statistical significance of differences was assessed using two-tailed Student's t tests. Data represent mean±SD: *P<0.05, **P<0.01.

FIGS. 5A-K. Recombinant Clec11a promotes osteogenesis in vitro and in vivo. (FIGS. 5A-B) Osteogenic differentiation of stromal cells from femur bone marrow of wild-type mice. Vehicle or 10 ng/ml rClec11a were added to osteogenic culture conditions and alizarin red staining was assessed 14 days later to test whether Clec11a would promote osteogenesis (n=3 independent experiments with duplicate cultures per treatment per experiment). (FIGS. 5C-D) MC3T3-E1 cells expressing empty vector or mouse Clec11a cDNA were subjected to osteogenic differentiation for 14 days (n=3 independent experiments with duplicate cultures per treatment per experiment). (FIG. 5E) Representative microCT images of trabecular bone in the distal femur metaphysis of wild-type mice treated with daily subcutaneous doses of rClec11a for 28 days (FIGS. 5E-K reflect n=4 mice per treatment, total, from four independent experiments). (FIGS. 5F-I) MicroCT analysis of trabecular bone parameters from the distal femur metaphysis of mice treated with daily subcutaneous doses of rClec11a for 28 days. (FIG. 5J) Trabecular bone formation rate in the femur metaphysis of mice treated with rClec11a for 28 days by calcein double labeling. (FIG. 5K) Bone resorption analysis based on the deoxypyridinoline/creatinine ratio in the urine. The statistical significance of differences among treatments was assessed using one-way ANOVAs with Tukey's multiple comparisons tests. Data represent mean±SD: *P<0.05, P<0.01, *P<0.001.

FIGS. 6A-I. Recombinant Clec11a prevents ovariectomy-induced bone loss (FIG. 6A) Representative microCT images of trabecular bone in the distal femur metaphysis. Two month-old sham operated mice (Mock) or ovariectomized mice (OVX) received daily subcutaneous injections with vehicle, 40 μg/kg human PTH, or 50 μg/kg rClec11a for 28 days. (FIGS. 6B-E) MicroCT analysis of trabecular bone parameters in the distal femur metaphysis of the mice from the experiment in FIG. 6A (FIGS. 6B-I reflect n=4 mice per treatment, total, from the same four independent experiments). (FIG. 6F) Bone resorption analysis based on the deoxypyridinoline/creatinine ratio in the urine. (FIG. 6G) Histomorphometry analysis of osteoclast number/bone surface in trabecular bone from the distal femur metaphysis. (FIG. 6H) Trabecular bone formation rate based on calcium double labeling in the distal femur metaphysis. (FIG. 6I) Histomorphometry analysis of osteoblast number/bone surface in trabecular bones from the distal femur metaphysis. The statistical significance of differences was assessed using one-way ANOVAs with Tukey's multiple comparisons tests. Data represent mean±SD: *$P<0.05$, $P<0.01$, *$P<0.001$.

FIGS. 7A-I. Recombinant Clec11a prevents dexamethasone-induced bone loss (FIG. 7A) Representative microCT images of trabecular bone in the distal femur metaphysis. Two month-old wild-type mice were treated with daily intraperitoneal injections of PBS or 20 mg/kg dexamethasone (DEX) for 28 days, with or without daily subcutaneous injections of vehicle, 40 µg/kg human PTH, or 50 µg/kg rClec11a. (FIGS. 7B-E) MicroCT analysis of trabecular bone parameters of mice from the same experiments (FIGS. 7B-I reflect n=4 mice per treatment, total, from four independent experiments). (FIG. 7F) Trabecular bone formation rate based on calcium double labeling in the distal femur metaphysis. (FIG. 7G) Histomorphometry analysis of osteoblast number/bone surface in trabecular bone from the distal femur metaphysis. (FIG. 7H) Bone resorption analysis based on the deoxypyridinoline/creatinine ratio in the urine. (FIG. 7I) Histomorphometry analysis of osteoclast number/bone surface in trabecular bone from the distal femur metaphysis. The statistical significance of differences was assessed using one-way ANOVAs with Tukey's multiple comparisons tests. Data represent mean±SD: *$P<0.05$, $P<0.01$, *$P<0.001$.

(FIGS. 8A-B) Targeting strategy to generate a loss-of-function Clec11a allele using Crispr-Cas9 gene targeting. Two sgRNAs were designed against sequences in intron 1 and intron 2 to engineer the deletion of exon 2 (FIG. 8A), which caused a frame shift that created a premature stop codon in exon 3 (FIG. 8B; note that region above number 2 is glutamic acid rich sequence, region above and to left of number 3 is leucine zipper region, region above 4 is C-type 1ctin domain). The resulting mutant protein has 76 amino acids, lacking all of the domains that are thought to be functionally important in Clec11a (FIG. 8B). Genotyping primer locations are marked in FIG. 8A (F: Forward primer; R: Reverse primer). (FIG. 8C) Genomic DNA PCR. Tail genomic DNA was extracted from Clec11a$^{+/+}$ and Clec11a$^{-/-}$ mice, followed by PCR amplification using the primers indicated in FIG. 8A. The amplicons were sequenced to confirm correct targeting. (FIG. 8D) Heterozygous Clec11a$^{+/-}$ mice were intercrossed and generated expected progeny in Mendelian ratios (p=0.37 by Chi-square test). (FIG. 8E) Anti-Clec11a antibody staining showed Clec11a concentrated in trabecular and cortical bone in vertebrae. Growth plate chondrocytes were marked by aggrecan staining. Bone was imaged by second harmonic generation (SHG) (n=3 independent experiments). (FIGS. 8F-H) Red blood cell (FIG. 8F), white blood cell (FIG. 8G) and platelet (FIG. 8H) counts in 2, 10 and 16 month-old Clec11a$^{-/-}$ and sex-matched littermate control mice (n=4-6 mice per genotype, total, from at least four independent experiments). The statistical significance of differences among genotypes was assessed using two-tailed Student's t tests. (FIGS. 8I-J) Hematopoietic colony formation by mouse bone marrow cells in cultures supplemented with rClec11a along with 1 U/ml EPO to promote erythroid progenitor colony formation (BRU-E; FIG. 8I) or 10 ng/ml GM-CSF to promote myeloid progenitor colony formation (CFU-G/M/GM; FIG. 8J) (n=3 independent experiments). The statistical significance of differences among treatments was assessed using one-way ANOVAs with Tukey's multiple comparisons tests. Data represent mean±SD: *$P<0.05$.

FIGS. 9A-J. Cortical bone analysis in Clec11a$^{-/-}$ mice, related to FIGS. 2A-V. (FIGS. 9A-C) Representative microCT images of cortical bone in the femur diaphysis of 2 month-old (FIG. 9A), 10 month-old (FIG. 9B) and 16 month-old (FIG. 9C) Clec11a$^{-/-}$ mice and sex-matched littermate controls. (FIGS. 9D-H) MicroCT analysis of the total area (FIG. 9D), cortical area (FIG. 9E), cortical area/total area (FIG. 9F), cortical thickness (FIG. 9G) and cortical bone mineral density (FIG. 9H) in the femur diaphysis (n=4-9 mice per genotype, total, from at least four independent experiments). (FIGS. 9I-J) Biomechanical tests of the peak load (FIG. 9I) and fracture energy (FIG. 9J) in the femur diaphysis (n=4-9 mice per genotype, total, from at least four independent experiments). The statistical significance of differences was assessed using two-tailed Student's paired t tests. Data represent mean±SD: *$P<0.05$.

(FIG. 10A) Representative microCT images of cortical bone in the femur diaphysis of 2 month-old wild-type mice injected with vehicle or various doses of rClec11a. (FIGS. 10B-F) MicroCT analysis of the total area (FIG. 10B), cortical area (FIG. 10C), cortical area/total area (FIG. 10D), cortical thickness (FIG. 10E) and cortical bone mineral density (FIG. 10F) in the femur diaphysis (n=4 mice per genotype, total, from four independent experiments). The statistical significance of differences was assessed using one-way ANOVAs with Tukey's multiple comparisons tests.

(FIG. 11A) Representative microCT images of cortical bone in the femur diaphysis. Two month-old sham operation mice (Mock) or ovariectomized mice (OVX) were injected with vehicle, 40 µg/kg human PTH (1-34) or 50 µg/kg rClec11a for 28 days. (FIGS. 11B-F) MicroCT analysis of the total area (FIG. 11B), cortical area (FIG. 11C), cortical area/total area (FIG. 11D), cortical thickness (FIG. 11E) and cortical bone mineral density (FIG. 11F) in the femur diaphysis (n=4 mice per genotype, total, from four independent experiments). The statistical significance of differences was assessed using one-way ANOVAs with Tukey's multiple comparisons tests. Data represent mean±SD: *$P<0.05$, **$P<0.01$.

(FIGS. 12A-D) White blood cell (FIG. 12A), neutrophil (FIG. 12B), lymphocyte (FIG. 12C) and monocyte (FIG. 12D) counts in two month-old wild-type mice treated with daily intraperitoneal injections of PBS or 20 mg/kg dexamethasone (DEX) for 28 days, with or without daily subcutaneous injections of vehicle, 40 µg/kg human PTH, or 50 µg/kg rClec11a. (FIG. 12E) Representative microCT images of cortical bone in the femur diaphysis of the same mice. (FIGS. 12F-J) MicroCT analysis of the total area (FIG. 12F), cortical area (FIG. 12G), cortical area/total area (FIG. 12H), cortical thickness (FIG. 12I) and cortical bone mineral density (FIG. 12J) in the femur diaphysis of the mice in this experiment (n=4 mice per genotype, total, from four independent experiments).

The statistical significance of differences among treatments was assessed using one-way ANOVAs with Tukey's multiple comparisons tests. Data represent mean±SD: P<0.01, *P<0.001.

FIGS. 13A-F. Administration of recombinant Clec11a after the onset of ovariectomy-induced osteoporosis reverses bone loss. (FIG. 13A) Representative microCT images of trabecular bone in the distal femur metaphysis. Two month-old sham operated mice (Mock) or ovariectomized mice (OVX) were left untreated for 28 days, then received daily subcutaneous injections with vehicle, 40 µg/kg human PTH, 50 µg/kg recombinant Clec11a (rClec11a) or 40 µg/kg human PTH plus 50 µg/kg rClec11a for 28 days. (FIGS. 13B-E) MicroCT analysis of trabecular bone volume/total volume (FIG. 13B), trabecular number (FIG. 13C), trabecular thickness (FIG. 13D), trabecular spacing (FIG. 13E) and trabecular bone mineral density (FIG. 13F) in the distal femur metaphysis of the mice from the experiment in FIG. 13A (FIGS. 13B-I reflect n=4 mice per treatment, total, from four independent experiments).

FIGS. 14A-D. Recombinant human Clec11a promotes bone formation by human bone marrow stromal cells in culture (hMSCs). (FIGS. 14A-D) Osteogenic differentiation of hMSCs in culture. Vehicle or 10 ng/ml recombinant human Clec11a were added to cultures. Alkaline phosphatase staining and alizarin red staining were performed after 8 days (FIGS. 14A-B) and 21 days (FIGS. 14C-D) to quantify osteogenic differentiation and mineralization (n=3 independent experiments).

Figure 15A:
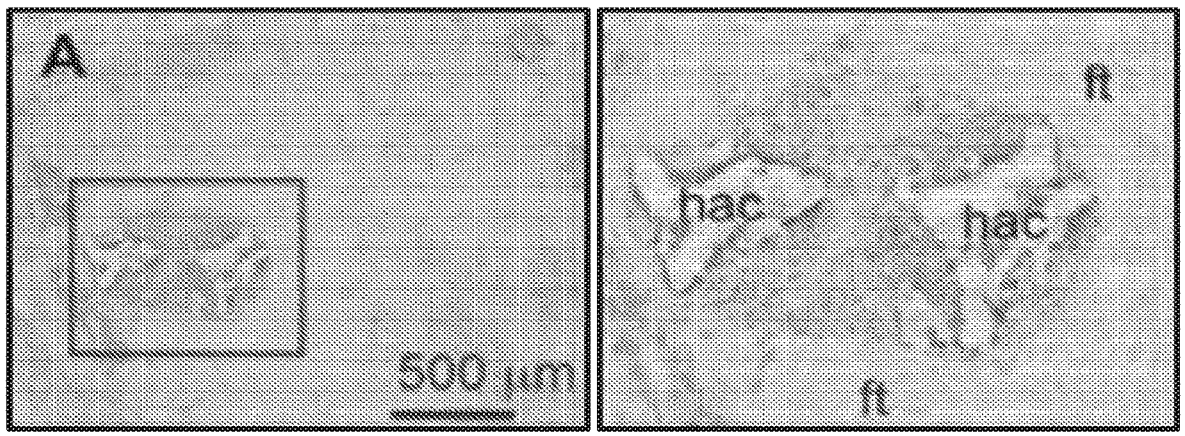
Figure 15B:
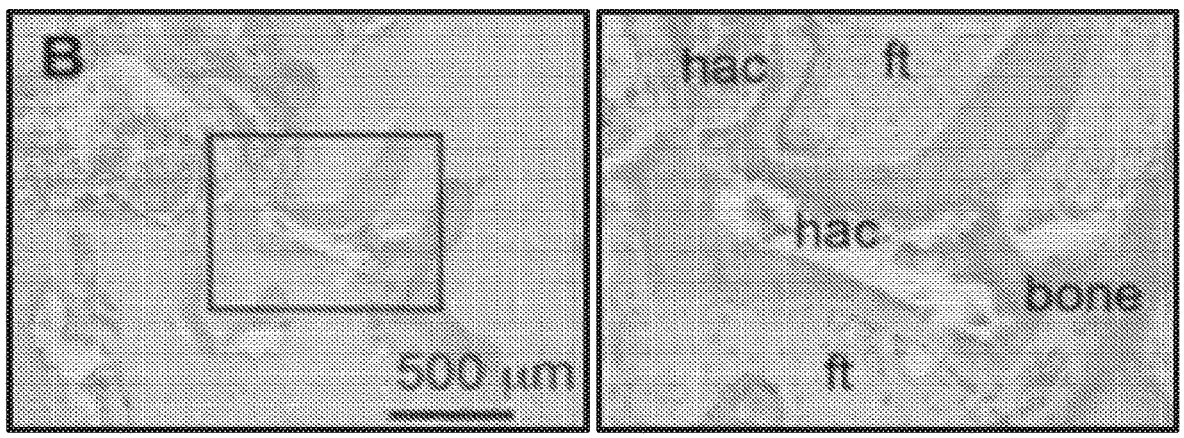

FIGS. 15A-B. rhClec11a promotes bone formation by hMSCs in vivo. (FIGS. 15A and 15B) In vivo transplantation of hMSCs in NSG mice. hMSCs were mixed with 40 mg of HA/TCP particles with vehicle or 10 ng/ml rhClec11a for 2 hours at 37° C., and then embedded in fibrin gels and transplanted subcutaneously into NSG mice. Vehicle or 50 µg/kg rhClec11a were subcutaneously injected daily for 4 weeks before the ossicles were dissected and sectioned for H&E staining (n=4 independent experiments). ft, fibrous tissue. hac, HA/TCP carrier. At this time point, little bone (pink) was observed in mice injected with vehicle, but extensive bone was observed in mice injected with rhClec11a.

DETAILED DESCRIPTION OF ILLUSTRATIVE EMBODIMENTS

As discussed above, bone trauma and bone diseases/disorders are a major health issue, and in particular for the aging population. Here, the inventors have identified CLEC11a, a poorly understood C-type lectin previously implicated in hematopoiesis, as an important regulator of bone growth and mineralization. In contrast to earlier reports, the inventors observed little hematopoietic effect in vitro from the addition of CLEC11a. Moreover, Clec11α-deficient mice showed reduced bone formation, but no changes in bone resorption and no changes in hematopoiesis within normal mice. Therefore, CLEC11a is proposed as a bone growth factor that promotes osteogenesis in vivo. These and other aspects of the disclosure are described in detail below

I. CLEC11A

C-type lectin domain family 11 member A, also known as Stem Cell Growth Factor (SCGF), is a protein that in humans is encoded by the CLEC11A gene. This gene encodes a member of the C-type lectin superfamily. It is a secreted sulfated glycoprotein that can promote colony formation by human hematopoietic progenitors in culture (Bannwarth et al., 1999; Bannwarth et al., 1998; Hiraoka et al., 1997; Mio et al., 1998). The plasma level of human Clec11a correlates with hemoglobin level (Keller et al., 2009; Ouma et al., 2010) and increases in patients after bone marrow transplantation (Ito et al., 2003). As a result, Clec11a has been considered a hematopoietic growth factor. However, Clec11 is also expressed in skeletal tissues (Hiraoka et al., 2001) and the physiological function of Clec11a in vivo has not yet been tested.

The encoded protein is a secreted sulfated glycoprotein. An alternative splice variant has been described but its biological nature has not been determined. The mRNA sequence can be found at accession no. NM_002975 (SEQ ID NO: 9), and the protein sequence can be found at accession no. NP_002966 (SEQ ID NO: 10). SCGF has been disclosed in the context of wound healing, tissue regeneration, stimulating implant fixation and angiogenesis (see, e.g., U.S. Patent Publication 2005/0066266). Antagonists of SCGF were proposed for treating atherosclerosis, tumors and scarring are also disclosed.

In certain embodiments, expression cassettes are employed to express CLEC11a. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide. Thus, reference to provision or administration of CLEC11a, as set forth herein, should be interpreted as including provision of both CLEC11a protein and nucleic acid sequences coding therefor.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |

TABLE 1-continued

Promoter and/or Enhancer

| Promoter/Enhancer | References |
|---|---|
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are bone specific or selective promoters.

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Multigene Constructs and IRES

In certain embodiments of the disclosure, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

C. Delivery of Expression Vectors

There are a number of ways in which expression vectors may be introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present disclosure. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

D. Antagonists

In another embodiment, use of antagonist to treat pathologic bone formation is also contemplated. The following discussion of CLEC11a antagonists is provided.

1. Antibodies

Antibodies to CLEC11a may be produced by standard methods as are well known in the art (see, e.g., Antibodies: A Laboratory Manual, Cold Spring Harbor Laboratory, 1988; U.S. Pat. No. 4,196,265). The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxy succinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). In particular, IgM antibodies may be converted to IgG antibodies. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies can be generated by subcloning heavy and light chain Fv DNAs from the cloning vector into a Lonza pConIgG1 or pConK2 plasmid vector, transfected into 293 Freestyle cells or Lonza CHO cells, and collected and purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

Modified antibodies may be made by any technique known to those of skill in the art, including expression through standard molecular biological techniques, or the chemical synthesis of polypeptides. Methods for recombinant expression are addressed elsewhere in this document.

A Single Chain Variable Fragment (scFv) is a fusion of the variable regions of the heavy and light chains of immunoglobulins, linked together with a short (usually serine, glycine) linker. This chimeric molecule, also known as a single domain antibody, retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single domain or single chain variable fragments lack the constant Fc region found in complete antibody molecules, and thus, the common binding sites (e.g., protein A/G) used to purify antibodies (single chain antibodies include the Fc region). These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. 5×10$^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the V$_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of cancer-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signalling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

2. Inhibitory Nucleic Acids

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Another general class of nucleic acid based inhibitors is ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). It has also been shown that ribozymes can elicit genetic changes in some cells lines to which they were applied; the altered genes included the oncogenes H-ras, c-fos and genes of HIV. Most of this work involved the modification of a target mRNA, based on a specific mutant codon that was cleaved by a specific ribozyme.

RNA interference (also referred to as "RNA-mediated interference" or RNAi) is another mechanism by which protein expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin et al., 1999; Montgomery et al., 1998; Sharp et al., 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin et al., 1999; Montgomery et al., 1998; Sharp, 1999; Sharp et al., 2000; Tabara et al., 1999). Moreover, dsRNA has been shown to silence genes in a wide range of systems, including plants, protozoans, fungi, C. elegans, Trypanasoma, Drosophila, and mammals (Grishok et al., 2000; Sharp, 1999; Sharp et al., 2000; Elbashir et al., 2001). It is generally accepted that RNAi acts post-transcriptionally, targeting RNA transcripts for degradation, and possibly by inhibiting translation. It appears that both nuclear and cytoplasmic RNA can be targeted (Bosher et al., 2000).

siRNAs must be designed so that they are specific and effective in suppressing the expression of the genes of interest. Methods of selecting the target sequences, i.e. those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). Of particular interest are those siRNAs that span an exon-intron junction.

The making of siRNAs has been mainly through direct chemical synthesis; through processing of longer, double stranded RNAs through exposure to Drosophila embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double stranded RNA. Methods of chemical synthesis are diverse. Non-limiting examples are provided in U.S. Pat. Nos. 5,889,136, 4,415,732, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM. This had been demonstrated by Elbashir et al. (2001) wherein concentrations of about 100 nM achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. See U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single stranded RNA is enzymatically synthesized from the PCR™ products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates can be attached to a solid surface. After transcription with RNA polymerase, the resulting dsRNA fragments may be used for detecting and/or assaying nucleic acid target sequences.

In a specific embodiment, the inventors propose to inhibit CLEC11a expression in adult tissues in vitro using siRNA or shRNA in a lentiviral vector. A GFP marker can be utilized to determine that cells took up the vector, and thus permit checking for appropriate inhibition of CLEC11a production. The use of an inducible promoter (discussed below) that allow induction of the siRNA or shRNA only under specific growth conditions permit reversible inhibition of CLEC11a. Self-deleting vectors may also be used.

II. BONE STRUCTURE AND PHYSIOLOGY

Bone is a living, growing tissue. It is porous and mineralized, and made up of cells, vessels, organic matrix and inorganic hydroxyapatite crystals. The human skeleton is actually made up of 2 types of bones: the cortical bone and the trabecular bone. Cortical bone represents nearly 80% of the skeletal mass. Cortical bone has a slow turnover rate and a high resistance to bending and torsion. It provides strength where bending would be undesirable as in the middle of long bones. Trabecular bone only represents 20% of the skeletal mass, but 80% of the bone surface. It is less dense, more elastic and has a higher turnover rate than cortical bone.

A. Bone Forming Cells

Osteoprogenitors.

Human bone precursor cells are characterized as small-sized cells that express low amounts of bone proteins (osteocalcin, osteonectin, and alkaline phosphatase) and have a low degree of internal complexity (Long et al., 1995). When stimulated to differentiate, these preosteoblast cells become osteoblast in their appearance, size, antigenic expression, and internal structure. Although these cells are normally present at very low frequencies in bone marrow, a process for isolating these cells has been described (U.S. Pat. No. 5,972,703).

A number of studies indicate that bone marrow derived cells have osteogenic potential. The majority of these investigations point to mesenchymal stem cells (MSC) as undergoing differentiation into osteoblasts when cultured in the presence of bone-active cytokines. Mesenchymal stem cells are a pluripotent population capable of generating multiple stromal cell lineages. MSC, as currently used, are a heterogeneous population of cells isolated by plastic adherence, and propagated by low-density passage. Nonetheless, a recent publication indicates the clonal nature of cell fate outcomes in MSC indicating that a single MSC cell can give rise to two or three mesenchymal lineages one of which is usually bone cells. These studies are consistent with earlier reports that demonstrated the osteogenic potential of bone marrow stromal cells, in particular the so-called CFU-f from both mice and human.

Single-cell isolation of human MSC generated clones that express the same surface phenotype as unfractionated MSC. Interestingly, of the 6 MSC clones evaluated, 2 retained osteogenic, chrondrogenic and adipogenic potential; others were bipotent (either osteo-plus chondrogenic potential, or osteo-adipocytic potential) or were uni-lineage (chondrocyte). This suggests that MSC themselves are heterogeneous in nature (although culture conditions also may have led to loss of lineage potential). To date, the self-renewal capacity of MSC remains in question. Nonetheless, these in vitro studies and other in vivo studies show that MSC can commit to the bone cell lineage and develop to the state of matrix mineralization in vitro, or bone formation in vivo.

Preosteoblasts.

Preosteoblasts are intermediate between osteoprogenitor cells and osteoblasts. They show increasing expression of bone phenotypic markers such as alkaline phosphatase. They have a more limited proliferative capacity, but nonetheless continue to divide and produce more preosteoblasts or osteoblasts.

Osteoblasts.

An osteoblast is a mononucleate cell that is responsible for bone formation. Osteoblasts produce osteoid, which is composed mainly of Type I collagen. Osteoblasts are also responsible for mineralization of the osteoid matrix. Bone is a dynamic tissue that is constantly being reshaped by osteoblasts, which build bone, and osteoclasts, which resorb bone. Osteoblast cells tend to decrease in number and activity as individuals become elderly, thus decreasing the natural renovation of the bone tissue.

Osteoblasts arise from osteoprogenitor cells located in the periosteum and the bone marrow. Osteoprogenitors are immature progenitor cells that express the master regulatory transcription factor Cbfa1/Runx2. Osteoprogenitors are induced to differentiate under the influence of growth factors, in particular the bone morphogenetic proteins (BMPs). Aside from BMPs, other growth factors including fibroblast growth factor (FGF), platelet-derived growth factor (PDGF), transforming growth factor beta (TGF-beta) may promote the division of osteoprogenitors and potentially increase osteogenesis. Once osteoprogenitors start to differentiate into osteoblasts, they begin to express a range of genetic markers including Osterix, Col1, ALP, osteocalcin, osteopontin, and osteonectin. Although the term osteoblast implies an immature cell type, osteoblasts are in fact the mature bone cells entirely responsible for generating bone tissue in animals and humans.

Osteoclasts.

An osteoclast is a type of bone cell that removes bone tissue by removing its mineralized matrix. This process is known as bone resorption. Osteoclasts and osteoblasts are instrumental in controlling the amount of bone tissue: osteoblasts form bone, osteoclasts resorb bone. Osteoclasts are formed by the fusion of cells of the monocyte-macrophage cell lineage. Osteoclasts are characterized by high expression of tartrate resistant acid phosphatase (TRAP) and cathepsin K.

Osteoclast formation requires the presence of RANK ligand (receptor activator of nuclear factor κβ) and M-CSF (Macrophage colony-stimulating factor). These membrane bound proteins are produced by neighbouring stromal cells and osteoblasts; thus requiring direct contact between these cells and osteoclast precursors. M-CSF acts through its receptor on the osteoclast, c-fms (colony stimulating factor 1 receptor), a transmembrane tyrosine kinase-receptor, leading to secondary messenger activation of tyrosine kinase Src. Both of these molecules are necessary for osteoclastogenesis and are widely involved in the differentiation of monocyte/macrophage derived cells. RANKL is a member of the tumor necrosis family (TNF), and is essential in osteoclastogenesis. RANKL knockout mice exhibit a phenotype of osteopetrosis and defects of tooth eruption, along with an absence or deficiency of osteoclasts. RANKL activates NF-κβ and NFATc1 (nuclear factor of activated t cells, cytoplasmic, calcineurin-dependent 1) through RANK. NF-κβ activation is stimulated almost immediately after RANKL-RANK interaction occurs, and is not upregulated. NFATc1 stimulation, however, begins about 24-48 hours after binding occurs and its expression has been shown to be RANKL dependent. Osteoclast differentiation is inhibited by osteoprotegerin (OPG), which binds to RANKL thereby preventing interaction with RANK.

B. Bone Formation

The formation of bone during the fetal stage of development occurs by two processes: intramembranous ossification and endochondral ossification. Intramembranous ossification mainly occurs during formation of the flat bones of the skull; the bone is formed from mesenchyme tissue. The steps in intramembranous ossification are development of ossification center, calcification, formation of trabeculae and development of periosteum. Endochondral ossification, on the other hand, occurs in long bones, such as limbs; the bone is formed around a cartilage template. The steps in endochondral ossification are development of cartilage model, growth of cartilage model, development of the primary ossification center and development of the secondary ossification center.

Endochondral ossification begins with points in the cartilage called "primary ossification centers." They mostly appear during fetal development, though a few short bones begin their primary ossification after birth. They are responsible for the formation of the diaphyses of long bones, short bones and certain parts of irregular bones. Secondary ossification occurs after birth, and forms the epiphyses of long bones and the extremities of irregular and flat bones. The diaphysis and both epiphyses of a long bone are separated by a growing zone of cartilage (the epiphyseal plate). When the child reaches skeletal maturity (18 to 25 years of age), all of the cartilage is replaced by bone, fusing the diaphysis and both epiphyses together (epiphyseal closure).

Remodeling or bone turnover is the process of resorption followed by replacement of bone with little change in shape and occurs throughout a person's life. Osteoblasts and osteoclasts, coupled together via paracrine cell signalling, are referred to as bone remodeling units. The purpose of remodeling is to regulate calcium homeostasis, repair microdamaged bones (from everyday stress) but also to shape and sculpture the skeleton during growth.

The process of bone resorption by the osteoclasts releases stored calcium into the systemic circulation and is an important process in regulating calcium balance. As bone formation actively fixes circulating calcium in its mineral form, removing it from the bloodstream, resorption actively unfixes it thereby increasing circulating calcium levels. These processes occur in tandem at site-specific locations.

Repeated stress, such as weight-bearing exercise or bone healing, results in the bone thickening at the points of maximum stress (Wolff's law). It has been hypothesized that this is a result of bone's piezoelectric properties, which cause bone to generate small electrical potentials under stress.

III. TREATMENTS

A. Bone Deficit Diseases and Conditions

There are a plethora of conditions which are characterized by the need to enhance bone formation or to inhibit bone resorption and thus would benefit from the use of CLEC11a and agonists thereof in promoting bone formation and/or bone repair. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. Several other conditions, such as, for example, vitamin D deficiency, exists.

Spinal Fusion.

Spinal fusion, also called spondylodesis or spondylosyndesis, is a neurosurgical or orthopedic surgical technique that joins two or more vertebrae. Surgeons use supplementary bone tissue—either from the patient (autograft) or a donor (allograft)—or artificial bone substitutes in conjunction with the body's natural bone growth (osteoblastic) processes to fuse two or more adjoining vertebrae. Spinal fusion treats a variety of pathological conditions to eliminate abnormal motion of the vertebrae that causes pain, neurological deficit, or spinal deformity. Common conditions incorporating spinal fusion in their surgical treatment are spinal stenosis, spondylolisthesis, cervical discopathy, spinal fractures, scoliosis, and kyphosis.

Fracture.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would represent a great advance.

Periodontal Disease.

Progressive periodontal disease leads to tooth loss through destruction of the tooth's attachment to the surrounding bone. Approximately 5-20% of the U.S. population (15-60 million individuals) suffers from severe generalized periodontal disease, and there are 2 million related surgical procedures. Moreover, if the disease is defined as the identification of at least one site of clinical attachment loss, then approximately 80% of all adults are affected, and 90% of those aged 55 to 64 years. If untreated, approximately 88% of affected individuals show moderate to rapid progression of the disease' which shows a strong correlation with age. The major current treatment for periodontal disease is regenerative therapy consisting of replacement of lost periodontal tissues. The lost bone is usually treated with an individual's own bone and bone marrow, due to their high osteogenic potential. Bone allografts (between individuals) can also be performed using stored human bone. Although current periodontal cost analyses are hard to obtain, the size of the affected population and the current use of bone grafts as a first-order therapy strongly suggest that this area represents an attractive target for bone-building therapies.

Osteopenia/Osteoporosis.

The terms osteopenia and osteoporosis refers to a heterogeneous group of disorders characterized by decreased bone mass and fractures. Osteopenia is a bone mass that is one or more standard deviations below the mean bone mass for a population; osteoporosis is defined as 2.5 SD or lower. An estimated 20-25 million people are at increased risk for fracture because of site-specific bone loss. Risk factors for osteoporosis include increasing age, gender (more females), low bone mass, early menopause, race (Caucasians in general; asian and hispanic females), low calcium intake, reduced physical activity, genetic factors, environmental factors (including cigarette smoking and abuse of alcohol or caffeine), and deficiencies in neuromuscular control that create a propensity to fall.

More than a million fractures in the U.S. each year can be attributed to osteoporosis. In economic terms, the costs (exclusive of lost wages) for osteoporosis therapies are $35 billion worldwide. Demographic trends (i.e., the gradually increasing age of the U.S. population) suggest that these costs may increase to $62 billion by the year 2020. Clearly, osteoporosis is a significant health care problem.

Osteoporosis, once thought to be a natural part of aging among women, is no longer considered age or gender-dependent. Osteoporosis is defined as a skeletal disorder characterized by compromised bone strength predisposing to an increased risk of fracture. Bone strength reflects the integration of two main features: bone density and bone quality. Bone density is expressed as grams of mineral per area or volume and in any given individual is determined by peak bone mass and amount of bone loss. Bone quality refers to architecture, turnover, damage accumulation (e.g., microfractures) and mineralization. A fracture occurs when a failure-inducing force (e.g., trauma) is applied to osteoporotic bone.

Current therapies for osteoporosis patients focus on fracture prevention. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but this is hardly the best approach to therapy. Thus, the osteoporotic patient population would benefit from new therapies designed to increase bone volume, strengthen bone and speed up the fracture repair process, thus getting these people on their feet before the complications arise.

Bone Reconstruction/Grafting.

A fourth example is related to bone reconstruction and, specifically, the ability to reconstruct defects in bone tissue that result from traumatic injury; as a consequence of cancer or cancer surgery; as a result of a birth defect; or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects and are an excellent material for bone implants or artificial joints such as hip, knee and joint replacements. However, experience has shown that a lack of viable bone binding to implants the defect can result in exposure of the appliance to infection, structural instability and, ultimately, failure to repair the defect. Thus, a therapeutic agent that stimulates bone formation on or around the implant will facilitate more rapid recovery.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed, but suffer from their devitalized nature in that they only function as scaffolds for endogenous bone cell growth.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate.

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

Primary Bone Cancer and Metastatic Bone Disease.

Bone cancer occurs infrequently while bone metastases are present in a wide range of cancers, including thyroid, kidney, and lung. Metastatic bone cancer is a chronic condition; survival from the time of diagnosis is variable depending on tumor type. In prostate and breast cancer and in multiple myeloma, survival time is measurable in years. For advanced lung cancer, it is measured in months. Cancer symptoms include pain, hypercalcemia, pathologic fracture, and spinal cord or nerve compression. Prognosis of metastatic bone cancer is influenced by primary tumor site, presence of extra-osseous disease, and the extent and tempo of the bone disease. Bone cancer/metastasis progression is determined by imaging tests and measurement of bone specific markers. Recent investigations show a strong correlation between the rate of bone resorption and clinical outcome, both in terms of disease progression or death.

Multiple Myeloma.

Multiple myeloma (MM) is a B-lymphocyte malignancy characterized by the accumulation of malignant clonal plasma cells in the bone marrow. The clinical manifestations of the disease are due to the replacement of normal bone marrow components by abnormal plasma cells, with subsequent overproduction of a monoclonal immunoglobulin (M protein or M component), bone destruction, bone pain, anemia, hypercalcemia and renal dysfunction.

As distinct from other cancers that spread to the bone (e.g., breast, lung, thyroid, kidney, prostate), myeloma bone disease (MBD) is not a metastatic disease. Rather, myeloma cells are derived from the B-cells of the immune system that normally reside in the bone marrow and are therefore intimately associated with bone. Indeed, the bone marrow microenvironment plays an important role in the growth, survival and resistance to chemotherapy of the myeloma cells, which, in turn, regulate the increased bone loss associated with this disorder (world-wide-web at multiplemyeloma.org). Over 90% of myeloma patients have bone involvement, versus 40-60% of cancer patients who have bone metastasis, and over 80% have intractable bone pain. Additionally, approximately 30% of myeloma patients have hypercalcemia that is a result of the increased osteolytic activity associated with this disease.

Common problems in myeloma are weakness, confusion and fatigue due to hypercalcemia. Headache, visual changes and retinopathy may be the result of hyperviscosity of the blood depending on the properties of the paraprotein. Finally, there may be radicular pain, loss of bowel or bladder control (due to involvement of spinal cord leading to cord compression) or carpal tunnel syndrome and other neuropathies (due to infiltration of peripheral nerves by amyloid). It may give rise to paraplegia in late presenting cases.

Myeloma Bone Disease.

As discussed above, unlike the osteolysis associated with other bone tumors, the MBD lesions are unique in that they do not heal or repair, despite the patients' having many years of complete remission. Mechanistically, this seems to be related to the inhibition and/or loss of the bone-forming osteoblast during disease progression. Indeed, bone marker studies and histomorphometry indicate that both the bone-resorbing osteoclast and osteoblast activity are increased, but balanced early in the disease, whereas overt MBD shows high osteoclast activity and low osteoblast activity. Thus, MBD is a disorder in which bone formation and bone loss are uncoupled and would benefit from therapies that both stimulate bone formation and retard its loss.

A number of therapeutic approaches have been used in MBD, with the endpoints of treating pain, hypercalcemia, or the reduction of skeletal related events (SRE). Many of these may present serious complications. Surgery, such as vertebroplasty or kyphoplasty, that is performed for stability and pain relief has the attendant surgical risks (e.g., infection) made worse by a compromised immune system and does not reverse existing skeletal defects. Radiation therapy and radioisotope therapy are both used to prevent/control disease progression and have the typical risks of irradiation therapies. More recently, drugs such as the bisphosphonates that inhibit osteoclast activity have become a standard of therapy for MBD, despite the fact that they work poorly in this disorder. In 9 major double-blind, placebo-controlled trials on bisphosphonates, only 66% of patients showed an effective reduction in pain; 56% showed a reduction in SRE and only 1 of the 9 demonstrated a survival benefit.

B. Pathologic Bone Formation

Pathologic bone formation is generally categorized into three groups based on the initiating stimulus: trauma, tumors, and idiopathic causes. In the trauma category, formation of ectopic bone occurs with major and minor traumatic incidents, surgery, burns, and other causes. For tumors, direct and reactive pathologic bone formation depends on the different neoplasms capable of ectopic bone formation. Idiopathic causes involve the formation of pathologic bone following neurologic injury and in systemic ossification disorders. The origin of the bone-forming cells in pathologic bone remains unclear. There is some evidence suggesting that these cells may arise from osteogenic stromal elements. Potent bone formation growth-regulating factors likely also participate in the formation of pathologic bone.

C. Combination Treatments

As discussed, the present disclosure provides for the treatment of bones disease and bone trauma by stimulating the production of new bone tissue, either locally or systemically. Other agents may be used in combination with CLEC11a or agonists thereof of the present disclosure. More generally, these agents would be provided in a combined amount (along with the CLEC11a or agonists thereof) to produce any of the effects discussed above. This process may involve contacting the cell or subject with both agents at the same time. This may be achieved by contacting the cell with a single composition or pharmacological formulation that includes both agents, or by contacting the cell or subject with two distinct compositions or formulations, at the same time, wherein one composition includes the intracellular inhibitor and the other includes the second agent.

Alternatively, one agent may precede or follow the other by intervals ranging from minutes to weeks. In embodiments where the agents are applied separately to the cell or subject, one would generally ensure that a significant period of time did not expire between the time of each delivery, such that the agents would still be able to exert an advantageously combined effect on the cell or subject. In such instances, it is contemplated that one may contact the cell or subject with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the CLEC11a or agonist thereof is "A" and the other agent is "B":

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Administration protocols and formulation of such agents will generally follow those of standard pharmaceutical drugs, as discussed further below. Combination agents include bisphosphonates (Didronel®, Fosamax® and Actonel®), SERMs (Evista) or other hormone derivatives, sclerostin inhibitors, and Parathyroid Hormone (PTH) or parathyroid related hormone analogs.

IV. PHARMACEUTICAL FORMULATIONS AND DELIVERY

A. Compositions and Routes

Pharmaceutical compositions of the present disclosure comprise an effective amount of CLEC11a or agonists thereof dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one anti-TGF-beta antibody, and optionally an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, 1289-1329, incorporated herein by reference). Except insofar as any conventional carrier is incompatible with the active ingredient, its use in the pharmaceutical compositions is contemplated.

The CLEC11a or agonist thereof may be admixed with different types of carriers depending on whether it is to be administered orally or by injection. The present disclosure can be administered buccally, intravenously, intradermally, trans dermally, intrathecally, intraarterially, intraperitoneally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., nanoparticles, liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular, the CLEC11a or agonist thereof is formulated into a syringeable composition for use in intravenous administration.

The CLEC11a or agonist thereof may be formulated into a composition in a free base, neutral or salt form or ester. It may also be synthesized/formulated in a prodrug form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric, fumaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

Further in accordance with the present disclosure, the composition of the present disclosure suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present disclosure is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In certain embodiments, the use of lipid delivery vehicles (e.g., liposomes) is contemplated for the formulation and administration of agents disclosed herein, or expression cassettes coding therefor. The formation and use of liposomes is generally known to those of skill in the art, and is also described below. Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200-500 Å, containing an aqueous solution in the core.

The following information can also be utilized in generating liposomal formulations. Phospholipids can form a variety of structures other than liposomes when dispersed in water, depending on the molar ratio of lipid to water. At low ratios the liposome is the recommended structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs. Liposomes may also be characterized by the type of lipid they comprise—positively charged, negatively charged or neutral lipids.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one can operate at the same time.

Examples of lipids include compounds that contain long-chain aliphatic hydrocarbons and their derivatives. A lipid may be naturally-occurring or synthetic (i.e., designed or produced by man). Lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

One of ordinary skill in the art would be familiar with the range of techniques that can be employed for dispersing a composition in a lipid vehicle. For example, the CLEC11a or agonist thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of CLEC11a or agonist thereof, about 0.5% of CLEC11a or agonist thereof, or about 1.0% of CLEC11a or agonist thereof. In other embodiments, the CLEC11a or agonist thereof may comprise between about 2% to about 75% of the weight of the unit, or between about 25% to about 60%, for example, and any range derivable therein. Naturally, the amount of the CLEC11a or agonist thereof in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose of CLEC11a or agonist thereof may also comprise from about 0.1 microgram/kg/body weight, about 0.2 microgram/kg/body weight, about 0.5 microgram/kg/body weight, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments of the present disclosure, the CLEC11a or agonist thereof are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tablets, troches, capsules, elixirs, suspensions, syrups, wafers, and the like. The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, such as in the treatment of periodontal disease, the compositions of the present disclosure may alternatively be incorporated with one or more excipients in the form of a mouthwash, dentifrice, buccal tablet, oral spray, gel or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet, gel or solution form that may be placed under the tongue, along the gum line, brushed on to teeth surfaces, or otherwise dissolved in the mouth. U.S. Pat. Nos. 6,074,674 and 6,270,750, both incorporated by reference, describe topical, sustained release compositions for periodontal procedures.

In further embodiments, CLEC11a or agonist thereof may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,537,514, 6,613,308, 5,466,468, 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be desirable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 nil of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sustained release formulations for treating of bone conditions include U.S. Pat. Nos. 4,722,948, 4,843,112, 4,975,526, 5,085,861, 5,162,114, 5,741,796 and 6,936,270, all of which are incorporated by reference. Methods and injectable compositions for bone repair are described in U.S. Pat. Nos. 4,863,732, 5,531,791, 5,840,290, 6,281,195, 6,288,043, 6,485,754, 6,662,805 and 7,008,433, all of which are incorporated by reference.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In particular, it is contemplated that delivery of CLEC11a or agonists or mimics thereof will be achieved through a slow release delivery system, which are well known in the art. These formulations are of particular relevance in treating bone fractures, in spinal fusion, or in the systemic treatment of osteoporosis (i.e., bone repair). A hydrogel is a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Common uses for hydrogels include scaffolds in tissue engineering and sustained-release drug delivery systems.

B. Devices

In addition to providing CLEC11a or agonist thereof for administration by routes discussed above, such agents, alone or in combination, may be used in the context of devices, such as implants. A variety of bone related implants are contemplated, including dental implants, joint implants such as hips, knees, and elbows, vertebral/spinal implants, and others. The CLEC11a or agonist thereof may be impregnated in a surface of the implant, including in a bioactive matrix or coating. The inhibitor may be further formulated to sustained, delayed, prolonged or time release. The coating may comprise polymers, for example, such as those listed below. The following is a list of U.S. patents relating to bone implants and devices which may be utilized in accordance with this embodiment of the disclosure:

TABLE 3

| U.S. Pat. No.* | Patent Title |
| --- | --- |
| 7,044,972 | Bone implant, in particular, an inter-vertebral implant |
| 7,022,137 | Bone hemi-lumbar interbody spinal fusion implant having an asymmetrical leading end and method of installation thereof |
| 7,001,551 | Method of forming a composite bone material implant |
| 6,994,726 | Dual function prosthetic bone implant and method for preparing the same |
| 6,989,031 | Hemi-interbody spinal implant manufactured from a major long bone ring or a bone composite |

TABLE 3-continued

| U.S. Pat. No.* | Patent Title |
| --- | --- |
| 6,988,015 | Bone implant |
| 6,981,975 | Method for inserting a spinal fusion implant having deployable bone engaging projections |
| 6,981,872 | Bone implant method of implanting, and kit for use in making implants, particularly useful with respect to dental implants |
| 6,929,662 | End member for a bone fusion implant |
| 6,923,830 | Spinal fusion implant having deployable bone engaging projections |
| 6,921,264 | Implant to be implanted in bone tissue or in bone tissue supplemented with bone substitute material |
| 6,918,766 | Method, arrangement and use of an implant for ensuring delivery of bioactive substance to the bone and/or tissue surrounding the implant |
| 6,913,621 | Flexible implant using partially demineralized bone |
| 6,899,734 | Modular implant for fusing adjacent bone structure |
| 6,860,884 | Implant for bone connector |
| 6,852,129 | Adjustable bone fusion implant and method |
| 6,802,845 | Implant for bone connector |
| 6,786,908 | Bone fracture support implant with non-metal spacers |
| 6,767,367 | Spinal fusion implant having deployable bone engaging projections 6,761,738 Reinforced molded implant formed of cortical bone |
| 6,755,832 | Bone plate implant |
| 6,730,129 | Implant for application in bone, method for producing such an implant, and use of such an implant |
| 6,689,167 | Method of using spinal fusion device, bone joining implant, and vertebral fusion implant |
| 6,689,136 | Implant for fixing two bone fragments to each other |
| 6,666,890 | Bone hemi-lumbar interbody spinal implant having an asymmetrical leading end and method of installation thereof |
| 6,652,592 | Segmentally demineralized bone implant |
| 6,648,917 | Adjustable bone fusion implant and method |
| 6,607,557 | Artificial bone graft implant |
| 6,599,322 | Method for producing undercut micro recesses in a surface, a surgical implant made thereby, and method for fixing an implant to bone |
| 6,562,074 | Adjustable bone fusion implant and method |
| 6,562,073 | Spinal bone implant |
| D473,944 | Bone implant |
| 6,540,770 | Reversible fixation device for securing an implant in bone |
| 6,537,277 | Implant for fixing a bone plate |
| 6,506,051 | Bone implant with intermediate member and expanding assembly |
| 6,478,825 | Implant, method of making same and use of the implant for the treatment of bone defects |
| 6,458,136 | Orthopaedic instrument for sizing implant sites and for pressurizing bone cement and a method for using the same |
| 6,447,545 | Self-aligning bone implant |
| 6,436,146 | Implant for treating ailments of a joint or a bone |
| 6,371,986 | Spinal fusion device, bone joining implant, and vertebral fusion implant 6,370,418 Device and method for measuring the position of a bone implant 6,364,880 Spinal implant with bone screws |
| 6,350,283 | Bone hemi-lumbar interbody spinal implant having an asymmetrical leading end and method of installation thereof |
| 6,350,126 | Bone implant |
| 6,287,343 | Threaded spinal implant with bone ingrowth openings |
| 6,270,346 | Dental implant for bone regrowth |
| 6,248,109 | Implant for interconnecting two bone fragments |
| 6,217,617 | Bone implant and method of securing |
| 6,214,050 | Expandable implant for inter-bone stabilization and adapted to extrude osteogenic material, and a method of stabilizing bones while extruding osteogenic material |
| 6,213,775 | Method of fastening an implant to a bone and an implant therefor |
| 6,206,923 | Flexible implant using partially demineralized bone |
| 6,203,545 | Implant for fixing bone fragments after an osteotomy |
| 6,149,689 | Implant as bone replacement |
| 6,149,688 | Artificial bone graft implant |
| 6,149,686 | Threaded spinal implant with bone ingrowth openings |
| 6,126,662 | Bone implant |
| 6,083,264 | Implant material for replacing or augmenting living bone tissue involving thermoplastic syntactic foam |
| 6,058,590 | Apparatus and methods for embedding a biocompatible material in a polymer bone implant |
| 6,018,094 | Implant and insert assembly for bone and uses thereof |
| 5,976,147 | Modular instrumentation for bone preparation and implant trial reduction of orthopedic implants |
| 5,906,488 | Releasable holding device preventing undesirable rotation during tightening of a screw connection in a bone anchored implant |
| 5,899,939 | Bone-derived implant for load-supporting applications |
| 5,895,425 | Bone implant |
| 5,890,902 | Implant bone locking mechanism and artificial periodontal ligament system |
| 5,885,287 | Self-tapping interbody bone implant |
| 5,819,748 | Implant for use in bone surgery |

TABLE 3-continued

| U.S. Pat. No.* | Patent Title |
|---|---|
| 5,810,589 | Dental implant abutment combination that reduces crestal bone stress 5,759,035 Bone fusion dental implant with hybrid anchor |
| 5,720,750 | Device for the preparation of a tubular bone for the insertion of an implant shaft |
| 5,709,683 | Interbody bone implant having conjoining stabilization features for bony fusion |
| 5,709,547 | Dental implant for anchorage in cortical bone |
| 5,674,725 | Implant materials having a phosphatase and an organophosphorus compound for in vivo mineralization of bone |
| 5,658,338 | Prosthetic modular bone fixation mantle and implant system |
| D381,080 | Combined metallic skull base surgical implant and bone flap fixation plate 5,639,402 Method for fabricating artificial bone implant green parts |
| 5,624,462 | Bone implant and method of securing |
| D378,314 | Bone spinal implant |
| 5,607,430 | Bone stabilization implant having a bone plate portion with integral cable clamping means |
| 5,571,185 | Process for the production of a bone implant and a bone implant produced thereby |
| 5,456,723 | Metallic implant anchorable to bone tissue for replacing a broken or diseased bone |
| 5,441,538 | Bone implant and method of securing |
| 5,405,388 | Bone biopsy implant |
| 5,397,358 | Bone implant |
| 5,383,935 | Prosthetic implant with self-generated current for early fixation in skeletal bone |
| 5,364,268 | Method for installing a dental implant fixture in cortical bone |
| 5,312,256 | Dental implant for vertical penetration, adapted to different degrees of hardness of the bone |

*The preceding patents are all hereby incorporated by reference in their entirety.

V. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Mice.

To generate Clec11a$^{-/-}$ mice, Cas9 mRNA and sgRNAs were transcribed using mMESSAGE mMACHINE T7 Ultra Kit and MEGAshortscript Kit (Ambion), purified by MEGAclear Kit (Ambion), and microinjected into C57BL/6 zygotes by the Transgenic Core Facility of the University of Texas Southwestern Medical Center (UTSW). Chimeric mice were genotyped by restriction fragment length polymorphism (RFLP) analysis and backcrossed onto a C57BL/Ka background to obtain germline transmission. Mutant mice were backcrossed onto a C57BL/Ka background for 3 to 6 generations prior to analysis. Wild-type C57BL/Ka mice were used for rClec11a injection, ovariectomy, and dexamethasone injection experiments. All procedures were approved by the UTSW Institutional Animal Care and Use Committee.

Flow Cytometry.

Antibodies used to analyze hematopoietic stem cells (HSCs) and multipotent hematopoietic progenitors (MPPs) included anti-CD150-PE-Cy5 (BioLegend, clone TC15-12F12.2, 1:200), anti-CD48-FITC (eBioscience, clone HM48-1, 1:200), anti-Sca-1-PEcy7 (eBioscience, E13-161.7, 1:200), anti-c-Kit-APC-eFluor780 (eBioscience, clone 2B8, 1:200) and the following antibodies against lineage markers: anti-Ter119-PE (eBioscience, clone TER-119, 1:200), anti-B220-PE (BioLegend, clone 6B2, 1:400), anti-Gr-1-PE (BioLegend, clone 8C5, 1:800), anti-CD2-PE (eBioscience, clone RM2-5, 1:200), anti-CD3-PE (BioLegend, clone 17A2, 1:200), anti-CD5-PE (BioLegend, clone 53-7.3, 1:400) and anti-CD8-PE (eBioscience, clone 53-6.7, 1:400). The following antibodies were used to identify restricted hematopoietic progenitors: anti-CD34-FITC (eBioscience, clone RAM34, 1:100); anti-CD16/32-Alexa Fluor 700 (eBioscience, clone 93, 1:200); anti-CD135-PEcy5 (eBioscience, clone A2F10, 1:100); anti-CD127-Biotin (BioLegend, clone A7R34, 1:200)+Streptavidin-PE-CF592 (BD Biosciences, 1:500); anti-cKit-APC-eFluor780 (eBioscience, clone 2B8, 1:200); anti-ScaI-PEcy7 (eBioscience, clone E13-161.7, 1:200) and lineage markers listed above. The following antibodies were used to identify differentiated cells: anti-CD71-FITC (BD Biosciences, clone C2, 1:200); anti-Ter119-APC (eBioscience, clone TER-119, 1:200); anti-CD3-PE (BioLegend, clone 17A2, 1:200); anti-B220-PEcy5 (BioLegend, clone RA3-6B2, 1:400); anti-Mac-1-APC-eFluor780 (eBioscience, M1/70, 1:200) and anti-Gr-1-PEcy7 (BioLegend, clone RB6-8C5, 1:400). Anti-CD45.2-FITC (BioLegend, clone 104, 1:200) and anti-CD45.1-APC-eFluor-78 (eBioscience, clone A20, 1:100) were used to distinguish donor from recipient cells in competitive reconstitution assays. The following antibodies were used to identify SSCs: anti-CD45-FITC (eBioscience, clone 30-F11, 1:200), anti-Ter119-FITC (eBioscience, clone TER-119, 1:200), anti-CD31-FITC (Biolegend, clone MEC13.3, 1:200) and anti-PDGFRα-biotin (eBioscience, clone APA5, 1:200). Cells were stained with antibodies in 200 μl of staining medium (HBSS+2% fetal bovine serum) on ice for 1 hour, and then washed by adding 2 ml of staining buffer followed by centrifugation. Biotin-conjugated antibodies were incubated with streptavidin-PE for another 20 minutes (Biolegend, 1:500). Cells were resuspended in staining medium with 1 µg/ml DAPI (Invitrogen) and analyzed with a FACSCanto flow cytometer (BD Biosciences) or sorted using a FACS Aria flow cytometer (BD Biosciences) with a 130 µm nozzle.

Long-Term Competitive Reconstitution Assays in Irradiated Mice.

Two month-old adult recipient mice were irradiated with an XRAD 320 irradiator (Precision X-Ray Inc.), giving two doses of 550 rad, delivered at least 2 hours apart. C57BL/Ka-Thy-1.1 (CD45.2) donor mice and C57BL/Ka-Thy-1.2 (CD45.1) recipient mice were used in transplant experiments. 300,000 donor whole bone marrow cells from Clec11a$^{-/-}$ or littermate control mice (CD45.2) were transplanted along with 300,000 recipient whole bone marrow cells (CD45.1) into lethally irradiated recipient mice (C57BL/Ka-Thy-1.1×C57BL/Ka-Thy-1.2 (CD45.1/CD45.2) heterozygotes). Peripheral blood was obtained from the tail veins of recipient mice at 4 to 16 weeks after transplantation. Blood was subjected to ammonium-chloride lysis of the red blood cells and leukocytes were stained with antibodies against CD45.1, CD45.2, B220, Mac-1, CD3 and Gr-1 to assess hematopoietic chimerism by donor and recipient cells by flow cytometry.

Bone Sectioning and Immunostaining.

Dissected bones were fixed in 4% paraformaldehyde overnight, decalcified in 10% EDTA for 4 days, and dehydrated in 30% sucrose for 2 days. Bones were sectioned (10 µm) using the CryoJane tape-transfer system (Leica). Sections were blocked in PBS with 10% horse serum for 30 minutes and then stained overnight at 4° C. with goat anti-Clec11a antibody (R&D systems, 1:500), rabbit anti-Aggrecan antibody (Chemicon, 1:500), rabbit anti-Perilipin antibody (Sigma, 1:2000) or goat anti-Osteopontin antibody (R&D, 1:500). Donkey anti-goat Alexa Fluor 488 and donkey anti-rabbit Alexia Fluor 555 were used as secondary antibodies (Invitrogen, 1:500). Slides were mounted with anti-fade prolong gold with DAPI (Invitrogen). Images were acquired using a Zeiss LSM780 confocal microscope or Olympus IX81 microscope.

Bone Marrow Digestion and Stromal Cell Differentiation.

Enzymatic digestion of bone marrow cells and CFU-F culture were performed as described previously (Suire et al., 2012). Briefly, intact marrow plugs were flushed from the long bones and subjected to two rounds of enzymatic digestion at 37° C. for 15 minutes each. The digestion buffer contained 3 mg/ml type I collagenase (Worthington), 4 mg/ml dispase (Roche Diagnostics) and 1 U/ml DNAse I (Sigma) in HBSS with calcium and magnesium. The digested marrow cells were pooled into staining medium (HBSS+2% fetal bovine serum) with 2 mM EDTA to stop the enzymatic reaction. Freshly digested single-cell suspensions were plated at a density of 5×10$^6$ cells in 10 cm plates with DMEM (Gibco) plus 20% fetal bovine serum (Sigma F2442, lot number 14M255; specific lots were selected for the ability to support CFU-F growth), 10 µM ROCK inhibitor (Y-27632, TOCRIS), and 1% penicillin/streptomycin (Invitrogen). Cell cultures were maintained at 37° C. in gas-tight chambers (Billups-Rothenberg, Del Mar, CA) that were flushed daily for 30 seconds with 5% $O_2$ and 5% $CO_2$ (balance Nitrogen) to enhance progenitor survival and proliferation (Morrison et al., 2000). Differentiation was assessed by replating primary CFU-F cells into 48-well plates (25,000 cells/cm$^2$). On the second day of culture, the medium was replaced with adipogenic (4 days), osteogenic (7 days or 14 days), or chondrogenic differentiation (14 days) medium (StemPro MSC differentiation kits; Life Technologies). Adipogenic differentiation was quantified by Oil Red O staining (Sigma). Osteogenic differentiation was quantified by StemTAG Alkaline Phosphatase Staining and Activity Assay Kit (Cell Biolabs) and alizarin red staining (Sigma). Chondrogenic differentiation was quantified by toluidine blue staining (Sigma). Osteogenic differentiation of MC3T3-E1 cells was performed using the StemPro osteogenesis differentiation kit (Life Technologies). Images were acquired using an Olympus IX81 microscope.

Microct Analysis.

Femurs and lumbar vertebrae were dissected, fixed overnight in 4% paraformaldehyde and stored in 70% ethanol at 4° C. The bones were scanned at an isotropic voxel size of 3.5 µm and 7 µm, respectively, at the Texas A&M University Baylor College of Dentistry (µCT 35; Scanco Medical AG, Bassersdorf, Switzerland). Trabecular bone parameters were measured by analyzing 100 slices in the distal metaphysis of femurs near the growth plate. Cortical bone parameters were measured by analyzing 100 slices in mid-diaphysis femurs. Vertebral bone parameters were measured by analyzing 200 slices in ventral L3 lumbar vertebrae.

Calcein Double Labeling and Histomorphometry Analysis.

On day 0 and day 7, mice were injected intraperitoneally with 10 mg/kg body mass calcein dissolved in calcein buffer (0.15 M NaCl plus 2% NaHCO$_3$ in water) and sacrificed on day 9. The tibias were fixed overnight in 4% paraformaldehyde at 4° C., dehydrated in 30% sucrose for 2 days and sectioned without decalcification (7 µm sections). Mineral apposition and bone formation rates were determined as previously described (Egan et al., 2012). For the quantification of osteoblast number/bone surface and osteoclast number/bone surface, decalcified 10 µm femur sections were stained histochemically for alkaline phosphatase (Roche) or tartrate-resistant acid phosphatase (Sigma) activity. Growth plate chondrocytes were identified based on staining with safranin O/fast green and quantified using Image J.

Bone Fractures.

A stainless steel wire was inserted into the intramedullary canal of the femur through the knee after anesthesia, and a bone fracture was introduced in the femur mid-diaphysis by 3-point bending. Buprenorphine was injected every 12 hours up to 72 hours after the surgery.

Bone Resorption Analysis.

Bone resorption rate was determined by measuring urinary levels of deoxypyridinoline (DPD) using a MicroVue DPD ELISA Kit (Quidel) according to the manufacturer's instructions. The DPD values were normalized to urinary creatinine levels using the MicroVue Creatinine Assay Kit (Quidel).

Recombinant Protein Purification.

Mouse Clec11a cDNA was cloned into pcDNA3 vector (Invitrogen) containing a C-terminal 1×Flag-tag, which was then transfected into HEK293 cells with Lipofectamine 2000 (Invitrogen) and subjected to stable cell line selection using 1 mg/ml G418 (Sigma). Stable clones with high Clec11a expression were cultured in DMEM plus 10% FBS (Sigma), and 1% penicillin/streptomycin (Invitrogen). Culture medium was collected every two days, centrifuged to eliminate cellular debris, and stored with 1 mM phenylmethylsulfonyl fluoride at 4° C. to inhibit protease activity. rClec11a was purified using ANTI-FLAG M2 Affinity Gel (Sigma), and eluted using 100 µg/ml 3×FLAG peptide in elution buffer (50 mM HEPES, 150 mM NaCl and 10% glycerol, pH=7.5). Eluted protein was concentrated by Amicon Ultra-15 Centrifugal Filter Units (Millipore), quantified by SDS-PAGE, and stored at −80° C.

Osteoporosis Model.

For ovariectomy-induced osteoporosis, 8 week-old virgin female mice were anesthetized using Isoflurane, shaved, and disinfected with Betadine. A dorsal midline incision was made and the periovarian fat pad was gently grasped to exteriorize the ovary. The fallopian tube was then clamped off and the ovary was removed by cutting above the clamped area. The uterine horn was returned into the abdomen and the same process was repeated on the other side. After surgery, buprenorphine was given for analgesia, and mice were closely monitored until they resumed full activity. Vehicle, 40 µg/kg PTH (1-34) or 50 µg/kg rClec11a were subcutaneously injected daily starting one day after the surgery and continuing for 28 days then the mice were analyzed. For dexamethasone-induced osteoporosis, PBS or 20 mg/kg dexamethasone was injected peritoneally into 8 week-old virgin female mice daily for 28 days. Vehicle, 40 µg/kg PTH (1-34) or 50 µg/kg rClec11a were subcutaneously injected at the same time.

qPCR and RNA-Seq.

For quantitative reverse transcription PCR (qPCR), 6000 PDGFRα$^+$CD45$^-$Ter119$^-$CD31$^-$ cells were flow cytometrically sorted from enzymatically dissociated bone marrow into Trizol (Invitrogen). RNA was extracted and reverse transcribed into cDNA using SuperScript III (Invitrogen). qPCR was performed using a Roche LightCycler 480. The primers for Clec11a mRNA were: 5'-AGG TCC TGG GAG GGA GTG-3' (Forward; SEQ ID NO: 1) and 5'-GGG CCT CCT GGA GAT TCT T-3' (Reverse; SEQ ID NO: 2). The primers for Actb mRNA were: 5'-GCT CTT TTC CAG CCT TCC TT-3' (Forward; SEQ ID NO: 3) and 5'-CTT CTG CAT CCT GTC AGC AA-3' (Reverse; SEQ ID NO: 4). For RNA-seq experiments, extracted RNAs were digested with DNAse I (Ambion) and purified with RNeasy MinElute Spin Columns (Qiagen). RNAs were then linearly amplified into double stranded cDNA using the Ovation RNA-seq V2 system (NuGEN). RNA-seq libraries were constructed using Ovation Ultralow System V2 1-16 (NuGEN) and sequenced using an Illumina HiSeq 2500 sequencer (100 bp paired-end) at the Next Generation Sequencing Core in the UTSW McDermott Center.

Statistical Analysis.

The statistical significance of differences between two treatments was assessed using two-tailed Student's t tests. The statistical significance of differences among more than two groups was assessed using one-way ANOVAs with Tukey's multiple comparison tests. The statistical significance of differences in long-term competitive reconstitution assays was assessed using two-way ANOVAs with Sidak's multiple comparison tests. All data represent mean±SD. *P<0.05, P<0.01, *P<0.001.

Blood Cell Counts.

Peripheral blood was collected from the tail vein using Microvette CB 300 K2E tubes (Sarstedt) and counted using a HEMAVET HV950 cell counter (Drew Scientific).

Hematopoietic Colony Formation.

Hematopoietic colony formation was assessed by seeding 20,000 unfractionated mouse femur bone marrow cells into MethoCult M3334 or MethoCult M3234 supplemented with 10 ng/ml GM-CSF (STEMCELL Technologeis). The cultures were incubated at 37° C. for 10 days and then colonies were counted under the microscope.

Biomechanical Analysis.

To assess biomechanical properties, femurs were rehydrated in PBS for at least 3 hours before testing. The femurs were preconditioned with 20 cycles of bending displacement (0.1 mm) and then loaded to failure with 3-point bending (each holding point was 4 mm from the middle break point) under displacement control (0.05 mm/sec) using a material testing system (Instron model #5565, Norwood, MA).

Genotyping.

To genotype Clec11a$^{+/+}$, Clec11$^{+/-}$, and Clec11a$^{-/-}$ mice the following primers were used: 5'-TTT GGG TGC TGG GAA GCC C-3' (SEQ ID NO: 5) and 5'-TTG CAC TGA GTC GCG GGT G-3' (SEQ ID NO: 6) (Clec11a$^{+/+}$: 910 bp; Clec11$^{+/-}$ or Clec11a$^{-/-}$: 538 bp). To distinguish between Clec11a$^{+/-}$ and Clec11a$^{-/-}$ mice, the following primers were used: 5'-GAG GAA GAG GAA ATC ACC ACA GC-3' (SEQ ID NO: 7) and 5'-TTG CAC TGA GTC GCG GGT G-3' (SEQ ID NO: 8) (Clec11a$^{+/-}$: 482 bp; Clec11a$^{-/-}$: no amplification product).

Example 2—Results

Clec11a is Highly Expressed by SSCs.

Figure 1Q:
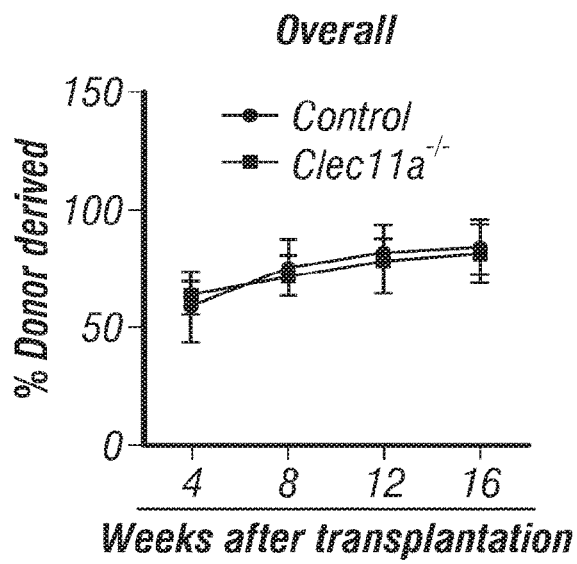
Figure 1R:
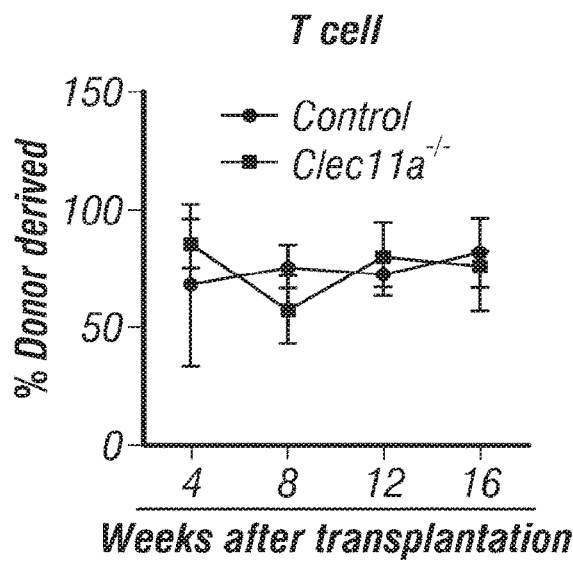
Figure 1S:
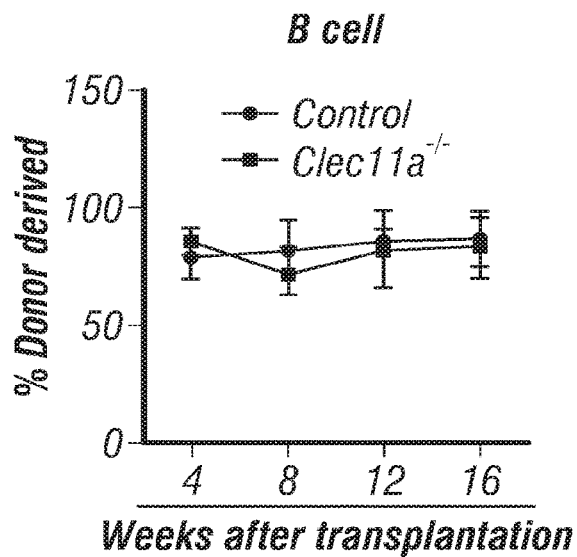
Figure 1T:
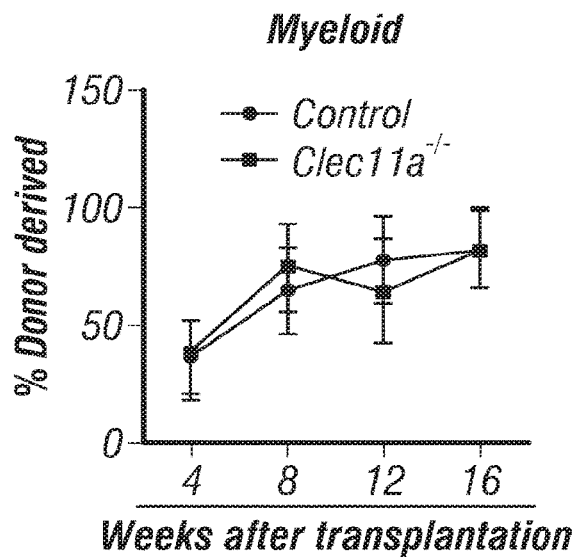

Reanalysis of our previously published microarray data (Ding et al., 2012) revealed that among enzymatically dissociated bone marrow cells, Clec11a is significantly more highly expressed by Scf-GFP$^+$CD45$^-$Ter119$^-$CD31$^-$ stromal cells (which are highly enriched for LepR$^+$ SSCs (Zhou et al., 2014)) and Col2.3-GFP$^+$CD45$^-$Ter119$^-$CD31$^-$ osteoblasts as compared to VE-cadherin$^+$ endothelial cells and unfractionated cells (FIG. 1A). The inventors confirmed this by RNA sequencing (FIG. 1B) and quantitative real-time PCR (qPCR) (FIG. 1C), each of which showed that Clec11a transcripts were at least 100-fold more abundant in PDGFRα$^+$CD45$^-$Ter119$^-$CD31$^-$ cells and Col2.3-GFP$^+$CD45$^-$Ter119$^-$CD31$^-$ osteoblasts as compared to unfractionated bone marrow cells (FIG. 1B and FIG. 1C).

To assess Clec11a protein expression, the inventors stained femur sections from 8 week-old mice with a commercially-available polyclonal antibody against Clec11a. Clec11a protein was concentrated near the growth plate at the boundary between the growth plate and the bone marrow, as well as around trabecular bones in the metaphysis (FIG. 1D and FIG. 1E). Clec11a was also in the cortical bone matrix of the femur diaphysis, with higher levels of staining near the periosteal surface (FIG. 1D and FIG. 1F). The level of Clec11a in cortical bone varied regionally within bones, with higher expression toward the femur neck as compared to the distal femur. The inventors observed a similar expression pattern in vertebrae, with anti-Clec11a antibody staining around trabecular bone and in cortical bone (FIG. 8E).

Clec11a is not Required for Hematopoiesis in Normal Mice.

Figure 8A:
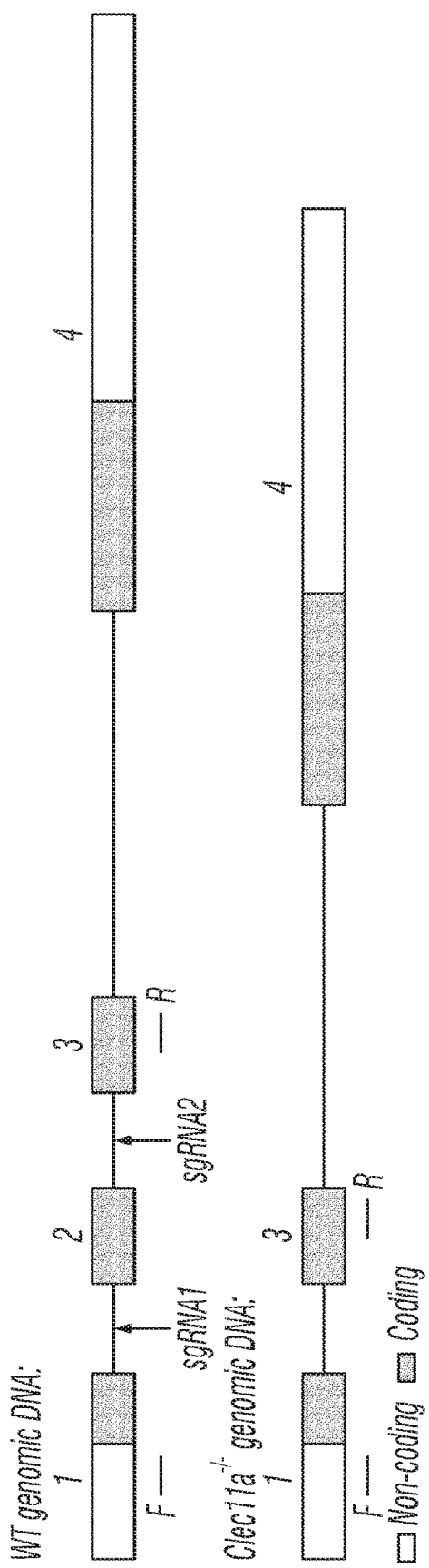
FIGS. 8A-J. Generation of Clec11a$^{-/-}$ mice and hematopoietic analysis, related to FIGS. 1A-T.
Figure 8B:
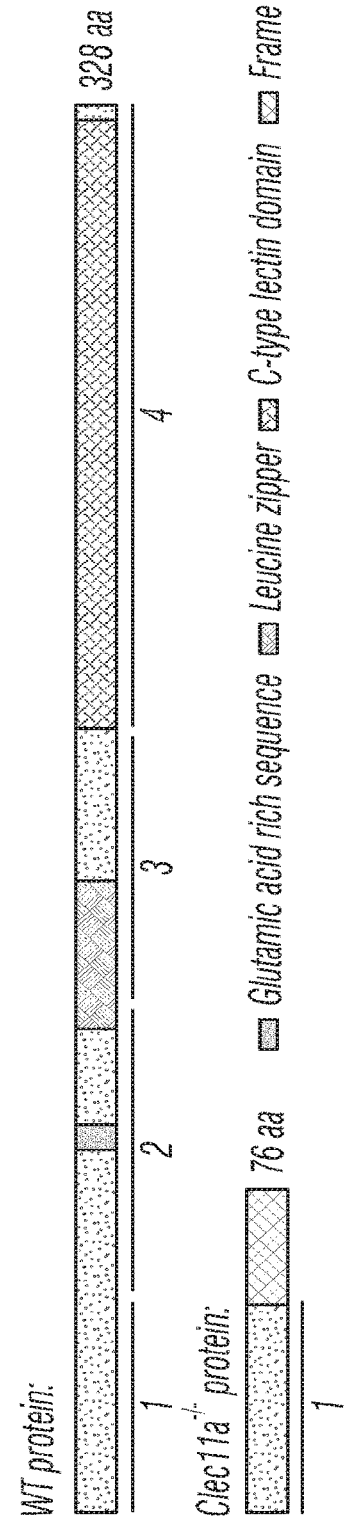
Figure 8C:
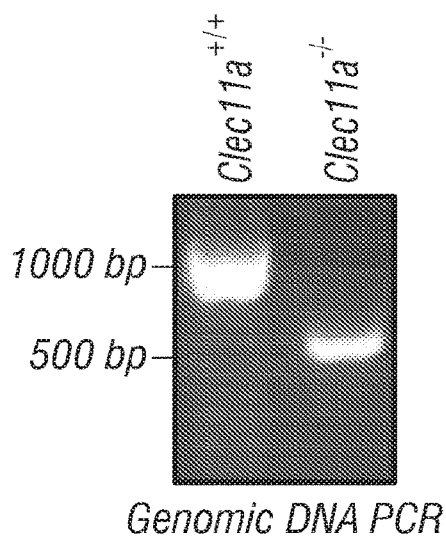

To test the physiological function of Clec11a, the inventors used CRISPR-Cas9 to generate a Clec11a mutant allele (Clec11a$^{-/-}$) by deleting the second exon of Clec11a (FIG. 8A). They did this by designing guide RNAs against intron sequences flanking exon 2, leading to the generation of a germline mutant allele lacking the second exon (FIG. 8A). This was predicted to be a strong loss of function allele as exon 2 deletion introduced a frame shift that created a premature stop codon in exon 3 (FIG. 8B). The predicted mutant protein did not contain any of the domains that are thought to be functionally important in Clec11a, including the polyglutamic acid sequence, the alpha-helical leucine zipper, or the C-type lectin domain (FIG. 8B). Deletion of Clec11a exon 2 in founder mice and germline transmission of the mutant allele were confirmed by PCR and sequencing of genomic DNA (FIG. 8C). Immunofluorescence analysis of femur sections with an anti-Clec11a polyclonal antibody suggested a complete loss of Clec11a protein from Clec11a$^{-/-}$ mice (FIG. 1E and FIG. 1F).

Figure 8D:
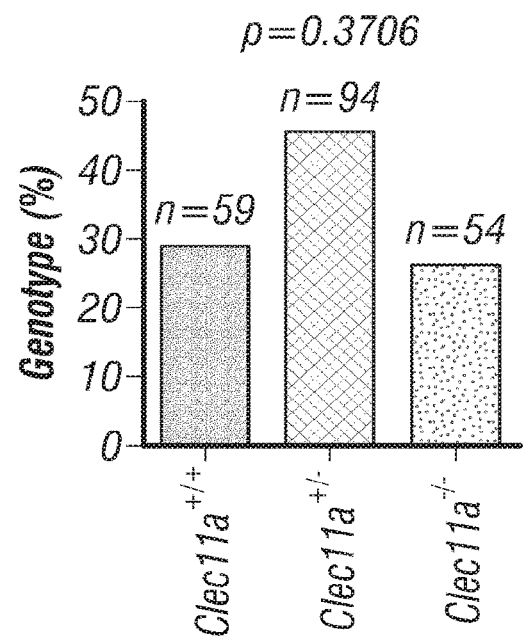
Figure 8E:
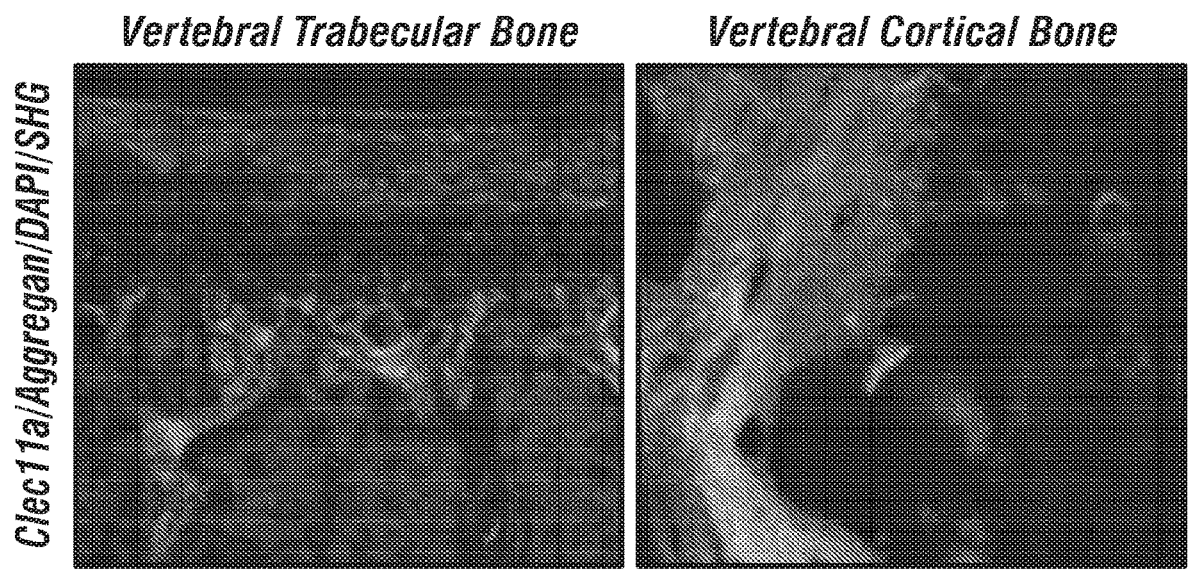
Figure 8F:
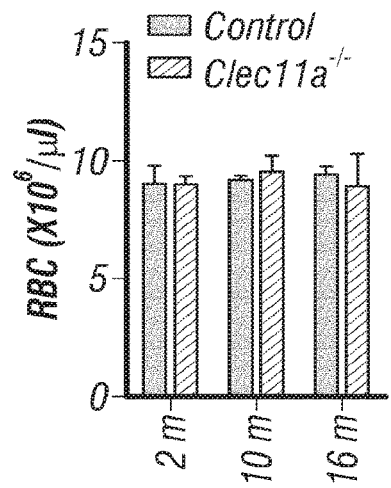
Figure 8G:
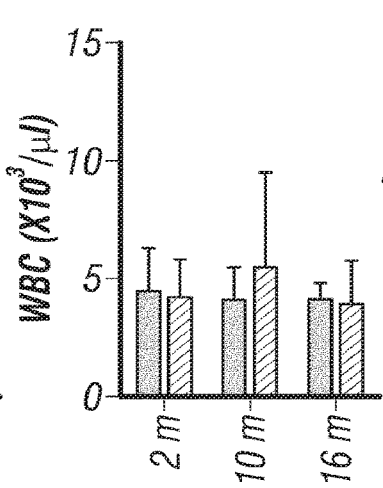
Figure 8H:
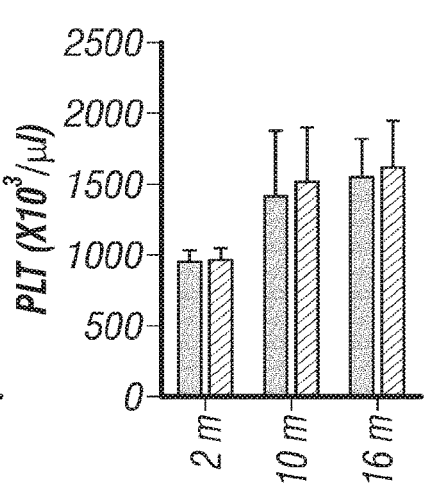

Clec11a$^{-/-}$ mice were born with the expected Mendelian frequency (FIG. 8D) and appeared grossly normal (FIG. 1G), with normal body mass (FIG. 1H) at 2 months of age. White blood cell, red blood cell, and platelet counts were normal in 2 month-old, 10 month-old, and 16 month-old Clec11a$^{-/-}$ mice (FIGS. 8F-8H).

Young adult Clec11a$^{-/-}$ mice had normal bone marrow and spleen cellularity (FIG. 1I), as well as normal frequencies of Mac1$^+$Gr1$^+$ myeloid cells, Ter119$^+$CD71$^+$ erythroid progenitors, CD3' T cells, and B220' B cells in the bone marrow and spleen (FIGS. 1J-1M). Clec11a$^{-/-}$ mice also had normal frequencies of CD150$^+$CD48$^-$Lineage$^-$Sca-1$^+$c-kit$^+$ HSCs (Kiel et al., 2005), CD150$^-$CD48$^-$Lineage$^-$Sca-1$^+$c-kit$^+$ multipotent progenitors (MPPs) (Kiel et al., 2008; Oguro et al., 2013), CD34$^+$FcγR$^+$Lineage$^-$Sca-1$^-$c-kit$^+$ granulocyte-macrophage progenitors (GMPs), CD34$^-$FcγR$^-$Lineage$^-$Sca-1$^-$c-kit' megakaryocyte-erythrocyte progenitors (MEPs), CD34$^+$FcγR$^-$Lineage$^-$Sca-1$^-$c-kit$^+$ common myeloid progenitors (CMPs) (Akashi et al., 2000) and Flt3$^+$IL7Rα$^+$Lineage$^-$Sca-1$^{low}$c-kit$^{low}$ common lymphoid progenitors (CLPs) (Kondo et al., 1997) in the bone marrow and spleen (FIGS. 1N-1P). Bone marrow from Clec11a$^{-/-}$ mice gave normal levels of long-term multilineage reconstitution upon transplantation into irradiated mice (FIGS. 1Q-1T). Clec11a is therefore not required for normal hematopoiesis in young adult mice.

Figure 8I:
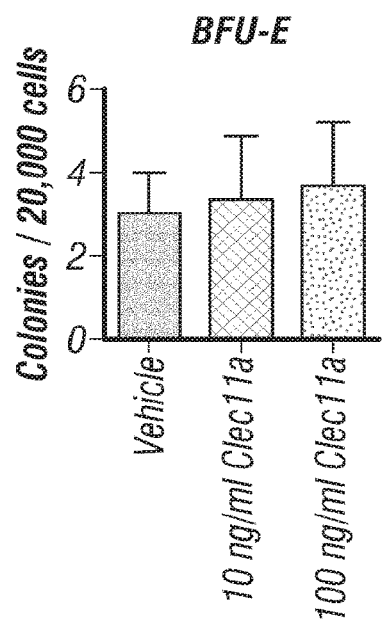
Figure 8J:
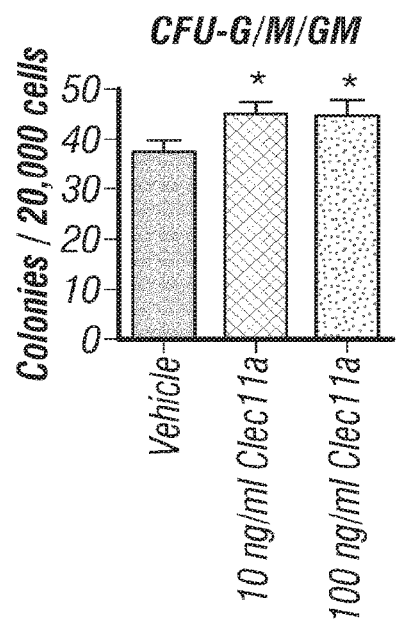

Human recombinant Clec11a increases erythroid (BFU-E) and myeloid (CFU-G/M/GM) colony formation by human bone marrow cells when added to culture along with EPO or GM-CSF, respectively (Hiraoka et al., 1997; Hiraoka et al., 2001). In cultures of mouse bone marrow cells, recombinant mouse Clec11a did not significantly increase BFU-E colony formation when added along with EPO and only slightly increased CFU-G/M/GM colony formation when added along with GM-CSF (FIGS. 8I and 8J).

Clec11a is Necessary for Osteogenesis.

To test whether Clec11a regulates osteogenesis, the inventors performed micro-computed tomography (micro-CT) analysis of the distal femur from sex-matched littermates. Trabecular bone volume was significantly reduced (by 24±18%) in 2 month-old Clec11a$^{-/-}$ mice as compared to littermate controls (FIG. 2A and FIG. 2D; in no case did the inventors observe any significant difference between Clec11a$^{+/+}$ and Clec11a$^{+/-}$ mice so samples from these mice were combined in the controls in all experiments). Clec11a$^{-/-}$ mice had significantly reduced trabecular bone thickness, increased trabecular spacing, and decreased connectively density and bone mineral density (FIGS. 2D-2I). With the exception of the reduction in bone mineral density, these defects seemed to worsen with age as 10 and 16 month-old Clec11a$^{-/-}$ mice exhibited a more profound reduction in trabecular bone volume (62±27% and 64±11%, respectively), trabecular number, trabecular thickness and connectivity density, as well as increased trabecular spacing (FIGS. 2B-2H).

Figure 9A:
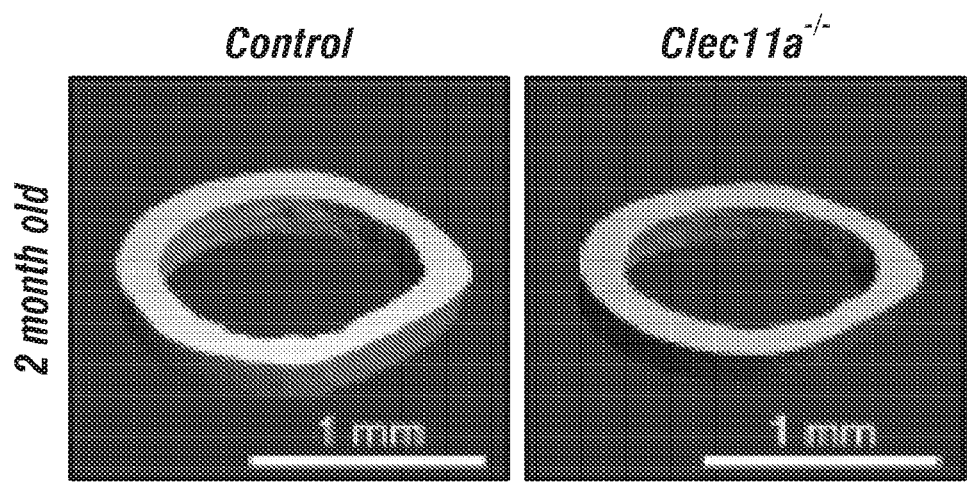
Figure 9B:
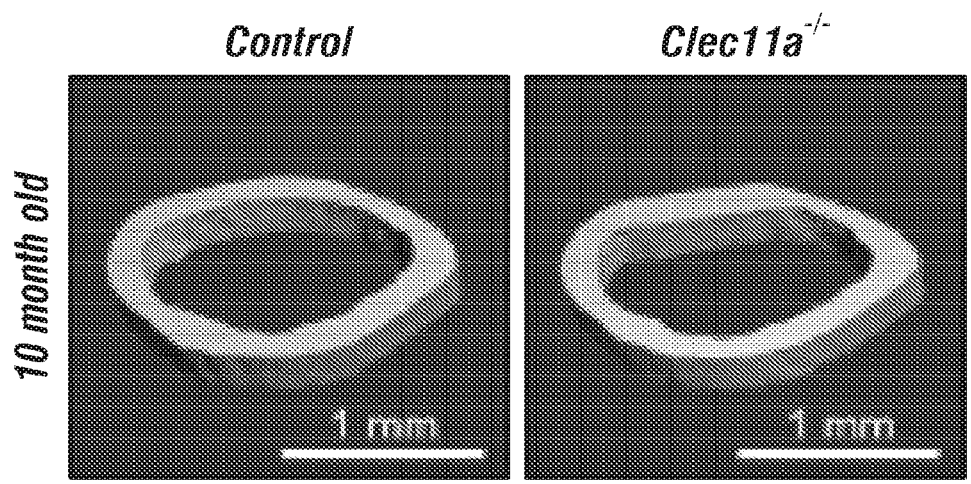
Figure 9C:
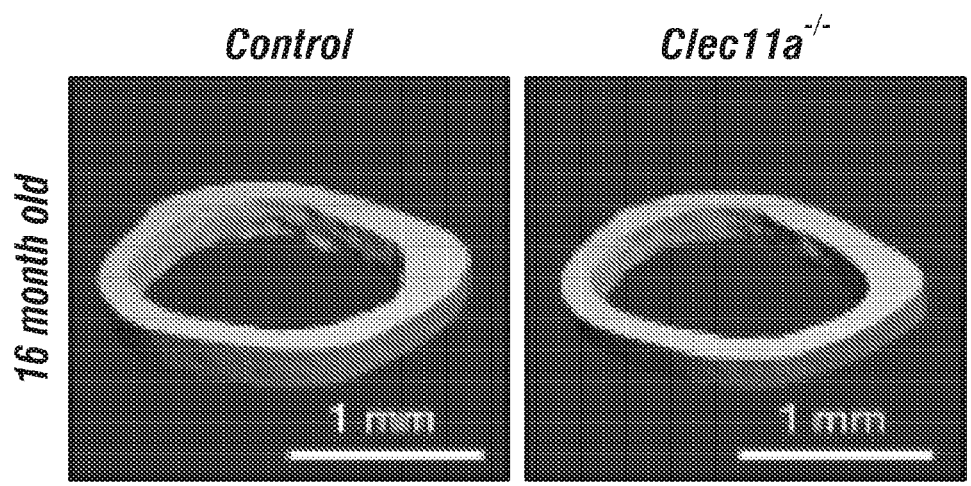
Figure 10A:
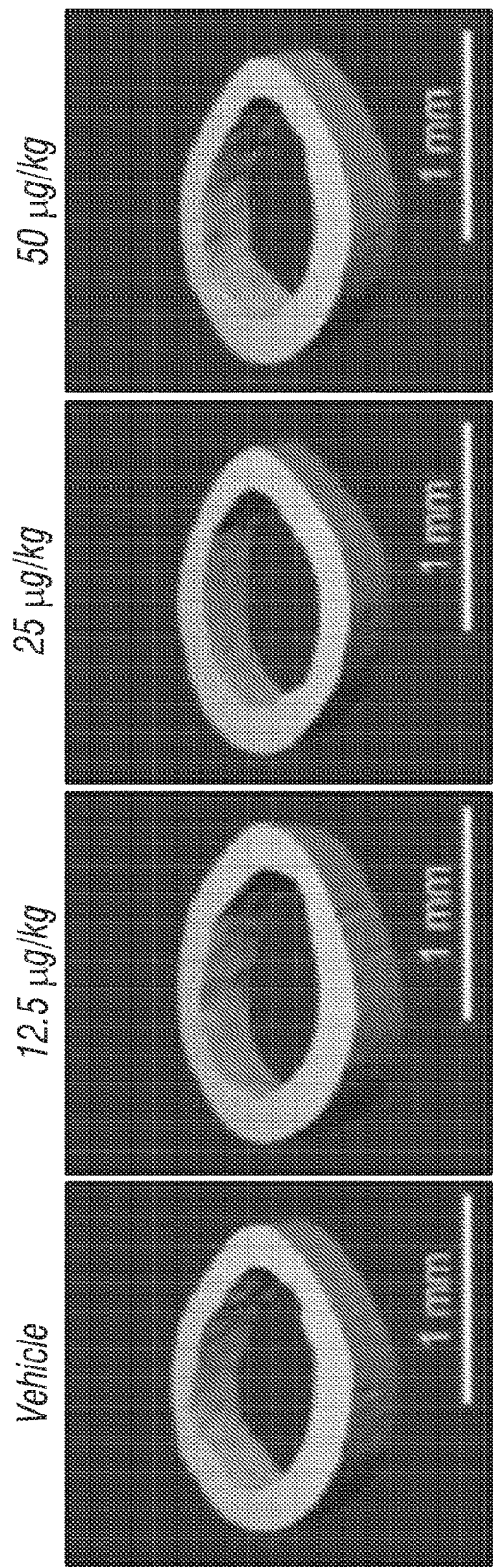
FIGS. 10A-F. Cortical bone analysis in mice wild-type mice treated with rClec11a, related to FIGS. 5A-K.
Figure 10B:
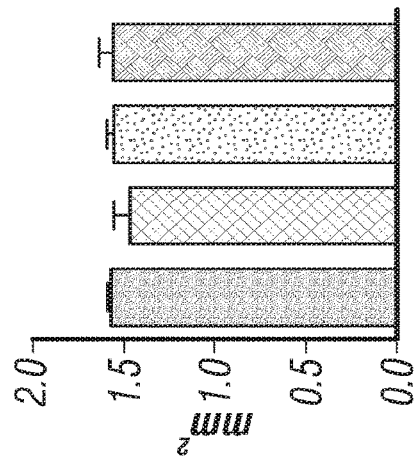
Figure 10C:
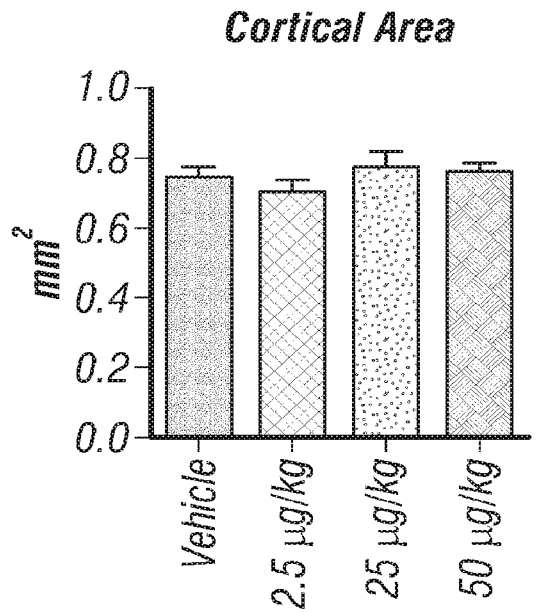
Figure 10D:
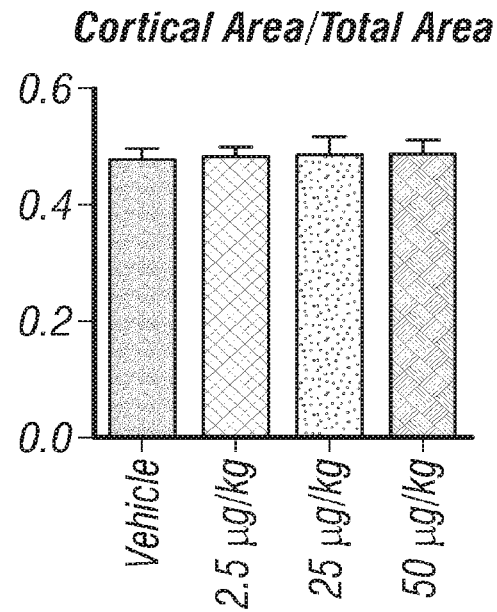
Figure 10E:
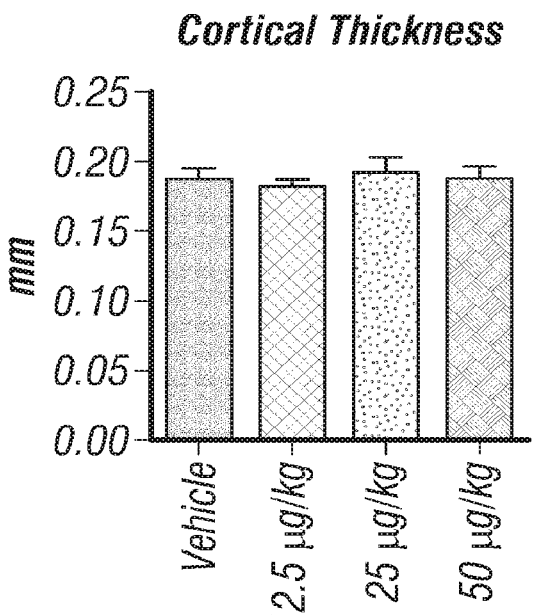
Figure 10F:
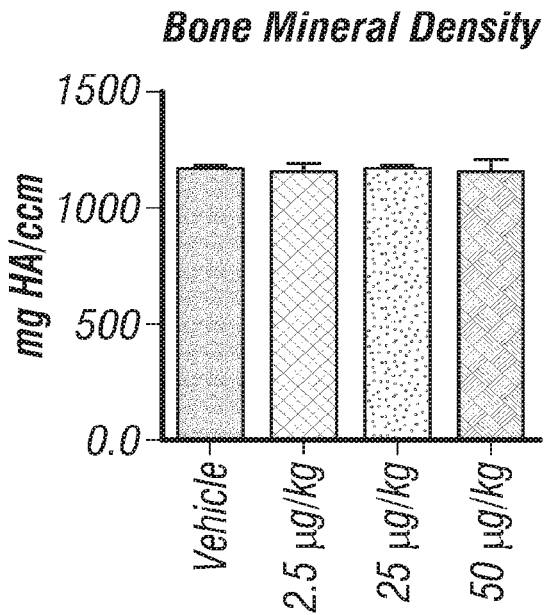

MicroCT analysis of cortical bone parameters in the femur diaphysis from sex-matched littermates did not show significant differences between Clec11a$^{-/-}$ and control mice at 2 or 10 months of age (FIGS. 9A and 9B). However, 16 month-old Clec11a$^{-/-}$ mice exhibited significantly reduced cortical bone area, cortical area/total area ratio, and cortical thickness as compared to controls (FIGS. 9C-9H). When the inventors tested the mechanical strength of bones using a three point bending test, they found significantly reduced peak load and fracture energy in the femur diaphysis of 2, 10, and 16 month-old Clec11a$^{-/-}$ as compared to sex-matched littermate control mice (FIGS. 9I and 9J).

Figure 2A:
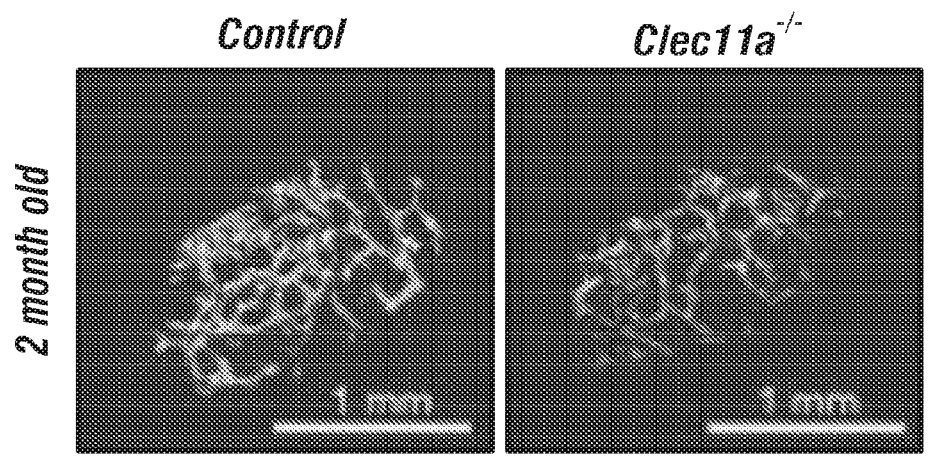
FIGS. 2A-V. Clec11a is necessary for osteogenesis in limb bones and vertebrae.
Figure 2B:
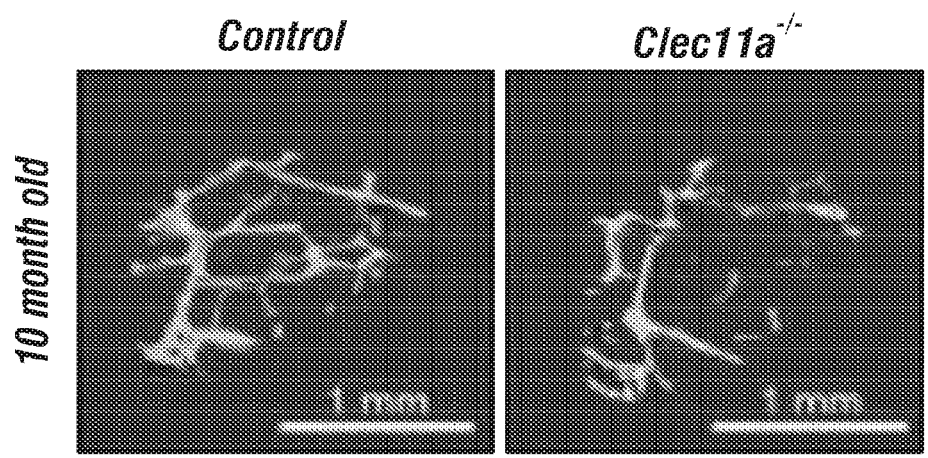
Figure 2C:
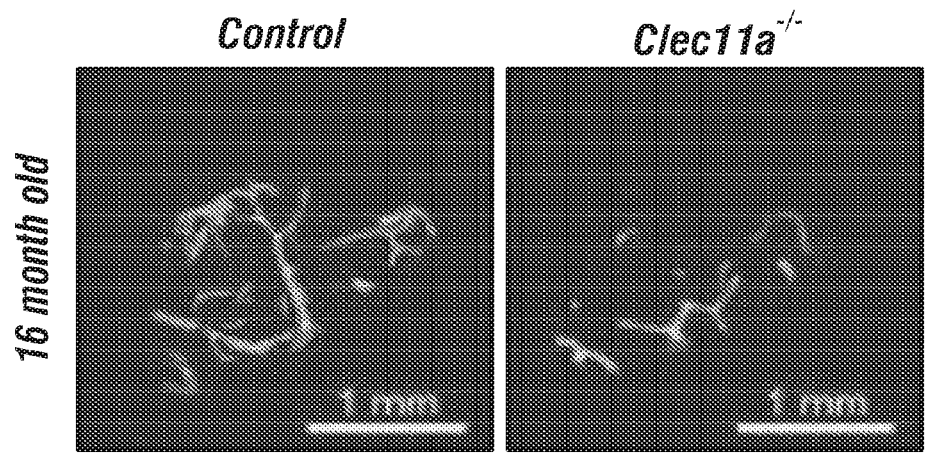
Figure 2J:
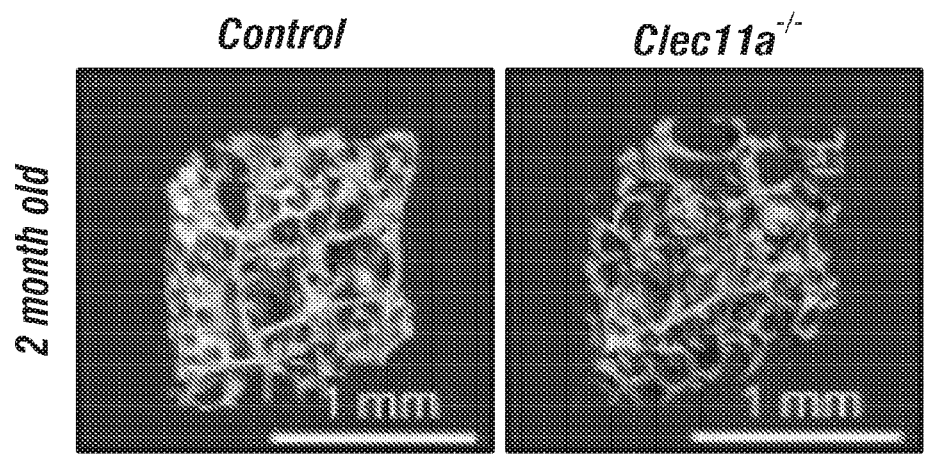
(FIGS. 2J-L) MicroCT images of trabecular bone from the ventral L3 lumbar vertebrae of 2 month-old (FIG. 2J), 10 month-old (FIG. 2K) and 16 month-old (FIG. 2L) Clec11a$^{-/-}$ mice and sex-matched littermate controls.
Figure 2K:
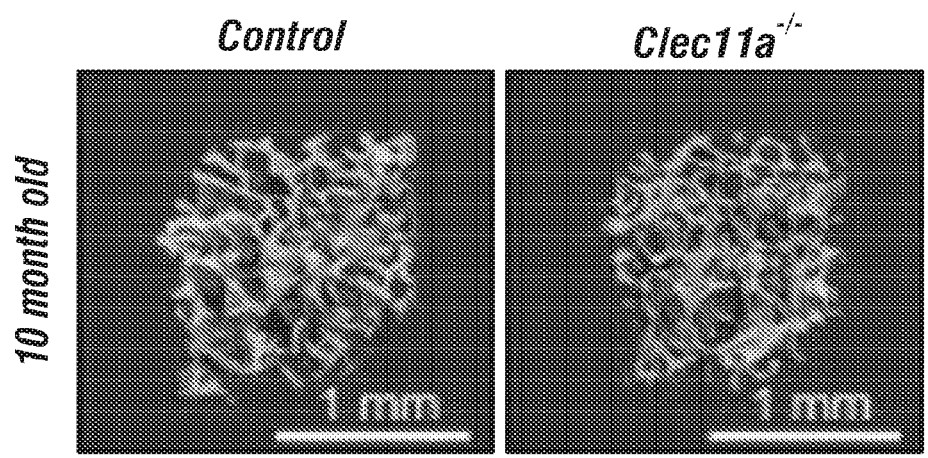
Figure 2L:
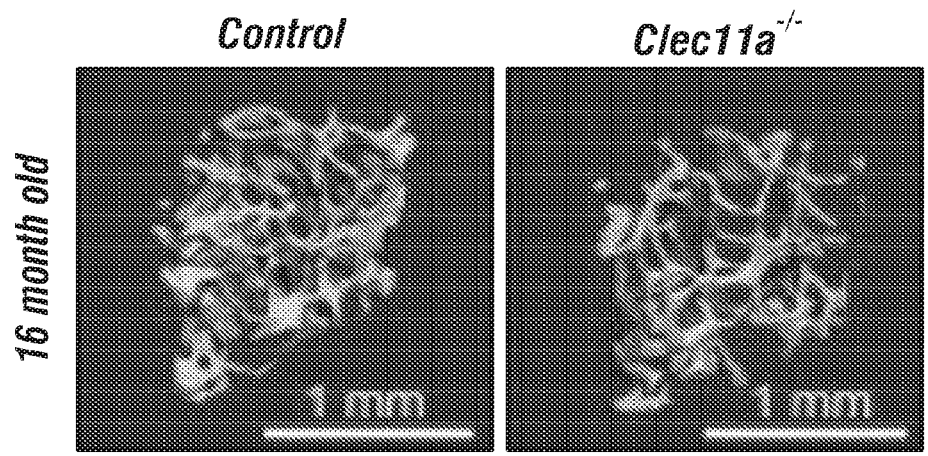
Figure 2M:
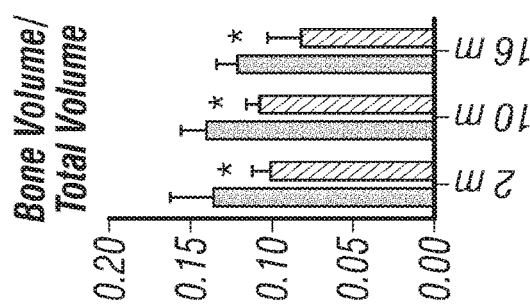
(FIGS. 2M-R) MicroCT analysis of trabecular bone parameters in the ventral L3 lumbar vertebrae of 2, 10 and 16 month-old Clec11a$^{-/-}$ mice and sex-matched littermate controls (n=4-9 mice per genotype, total, from at least four independent experiments).
Figure 2N:
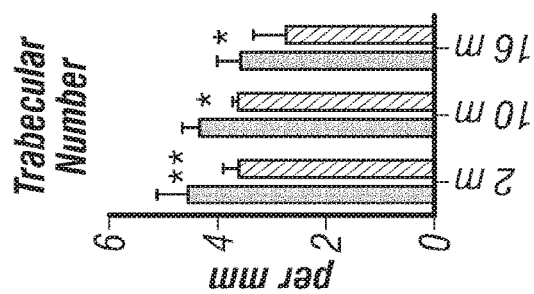
Figure 2O:
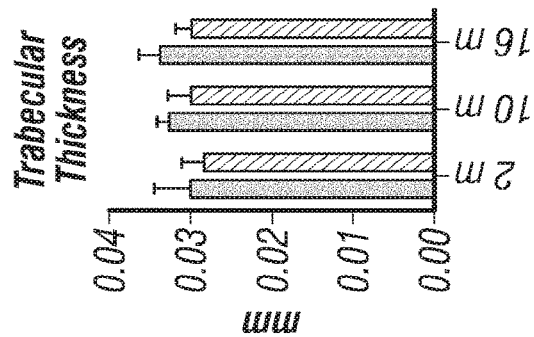
Figure 2P:
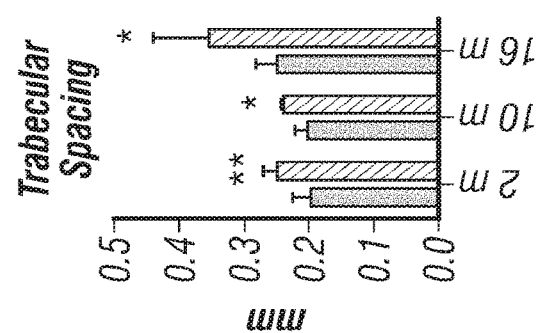
Figure 2Q:
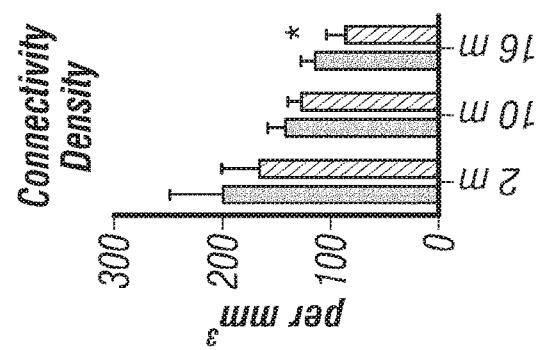
Figure 2R:
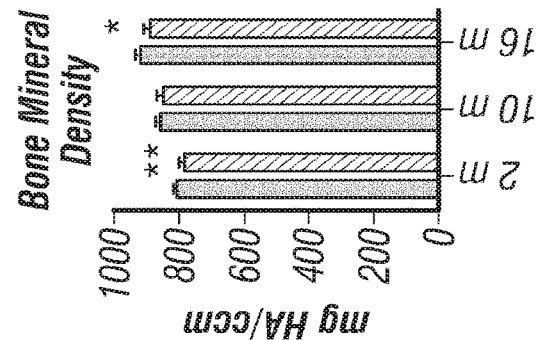

To test whether other bones also exhibit defects in the absence of Clec11a, the inventors examined L3 lumbar vertebrae from Clec11a$^{-/-}$ as compared to sex-matched littermate control mice. Micro-CT analysis of the vertebrae as a whole did not detect a difference between Clec11a$^{-/-}$ and sex-matched littermate control mice (data not shown). However, the inventors did observe a significant reduction in trabecular bone in the ventral portion of L3 vertebrae at 2, 10, and 16 months of age (FIGS. 2J-2L). The inventors observed significantly reduced trabecular bone volume and trabecular number, and significantly increased trabecular spacing in 2, 10 and 16 month-old Clec11a$^{-/-}$ as compared to sex-matched littermate control mice (FIGS. 2M-2P). Clec11a is therefore required to maintain bone in limb and vertebral bones.

Figure 2S:
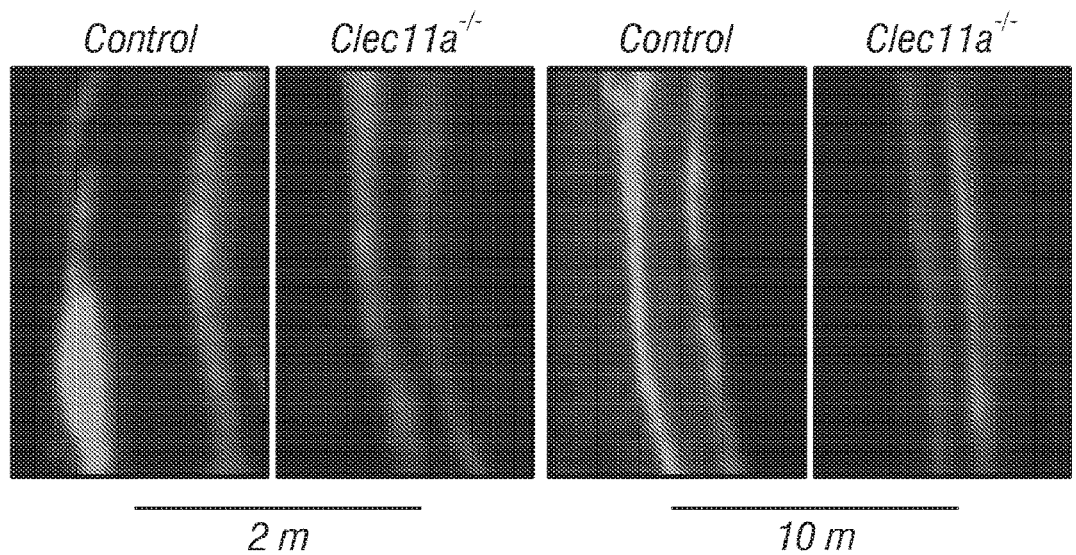
(FIGS. 2S-U) Representative calcein double labeling images (FIG. 2S) with quantification of the trabecular bone mineral apposition (FIG. 2T) and trabecular bone formation (FIG. 2U) rates in the femur metaphysis of 2 and 10 month-old mice (n=4 mice per genotype, total, from four independent experiments).
Figure 2T:
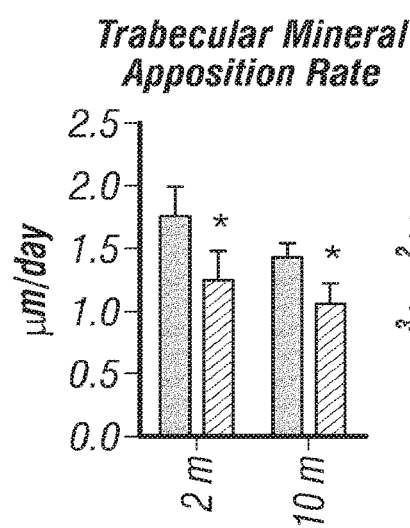
Figure 2U:
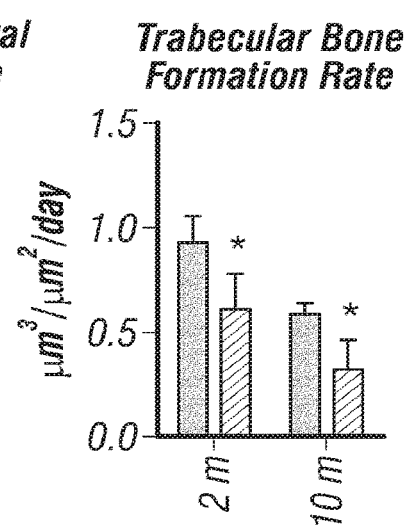
Figure 2V:
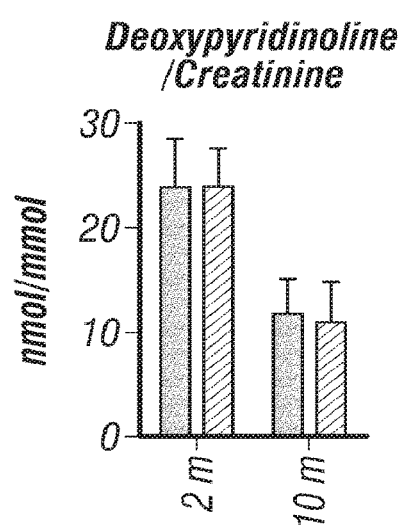

To determine whether Clec11a regulates bone formation, the inventors performed calcein double labeling to assess the rate of trabecular bone formation (FIG. 2S). The trabecular bone mineral apposition and trabecular bone formation rates were both significantly decreased in the femur metaphysis of 2 and 10 month-old Clec11a$^{-/-}$ as compared to sex-matched littermate control mice (FIG. 2T and FIG. 2U; 16 month-old mice were not assessed in these experiments). In contrast, the urinary bone resorption marker deoxypyridinoline did not significantly differ between Clec11a$^{-/-}$ and sex-matched littermate control mice (FIG. 2V). This suggested that the difference in trabecular bone volume between Clec11a$^{-/-}$ and littermate control mice reflected reduced bone formation in adult mice rather than a change in bone resorption.

Clec11a is Necessary for Normal Osteogenic Differentiation.

Figure 3B:
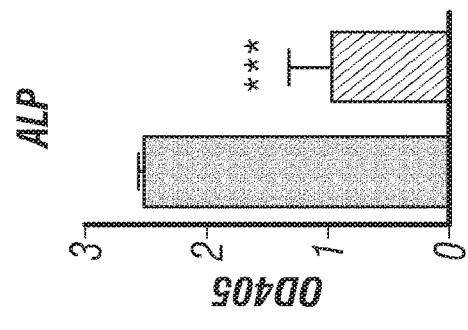
Figure 3D:
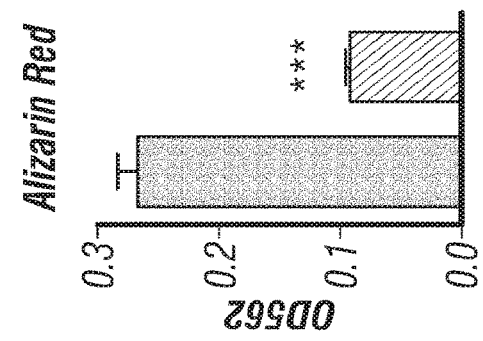
Figure 3A:
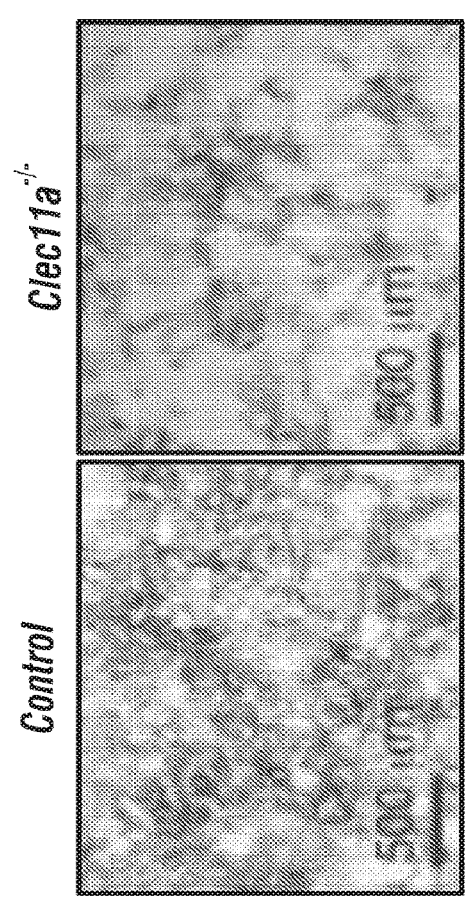
Figure 3C:
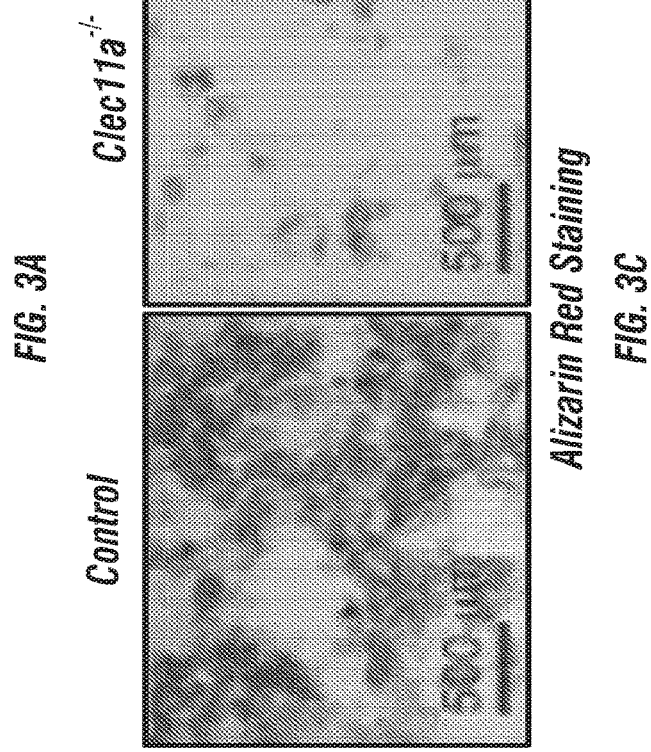
Figure 3F:
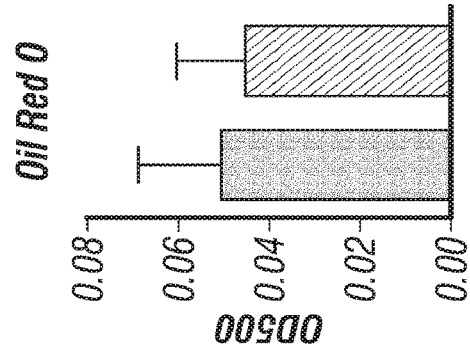
(FIG. 3E and FIG. 3F) Adipogenic differentiation in culture of bone marrow stromal cells from femur bone marrow of Clec11$^{-/-}$ mice and sex-matched littermate controls. Oil red O staining was performed after 4 days (n=3 independent experiments).
Figure 3H:
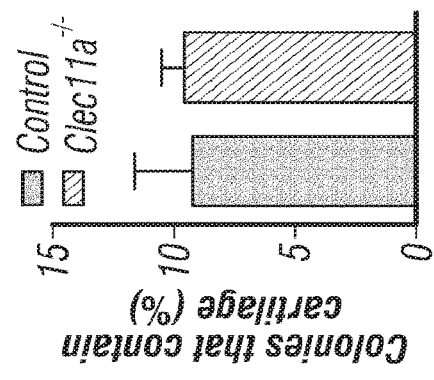
(FIG. 3G and FIG. 3H) Chondrogenic differentiation in culture of bone marrow stromal cells from femur bone marrow of Clec11$^{-/-}$ mice and sex-matched littermate controls. Toluidine blue staining was performed after 14 days (n=3 independent experiments).
Figure 3E:
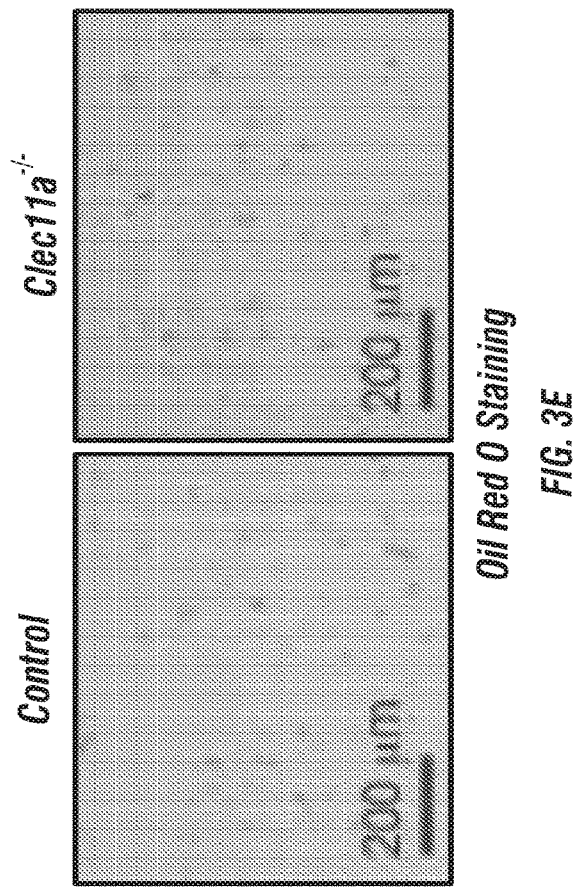
Figure 3G:
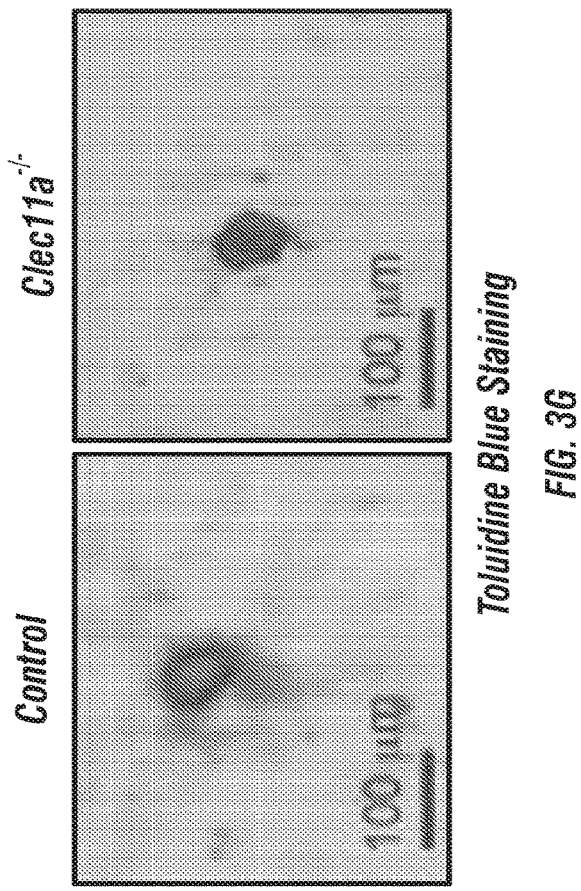

To test whether Clec11a regulates the differentiation of SSCs, the inventors cultured CFU-F from enzymatically dissociated Clec11a$^{-/-}$ and littermate control bone marrow cells, then replated equal numbers of Clec11a$^{-/-}$ or control cells under osteogenic, adipogenic, or chondrogenic culture conditions. Consistent with the decreased osteogenesis in vivo, fibroblasts from Clec11a$^{-/-}$ mice gave rise to significantly fewer cells with alkaline phosphatase staining or alizarin red staining as compared to control fibroblasts under osteogenic culture conditions (FIGS. 3A-3D). In contrast, under adipogenic (FIG. 3E and FIG. 3F) and chondrogenic (FIGS. 3G and 3H) culture conditions, the inventors did not detect any difference between Clec11a$^{-/-}$ and control cells in terms of the amount of oil red O or toluidine blue staining. Clec11a was thus required for normal osteogenic differentiation but not for adipogenic or chondrogenic differentiation by bone marrow stromal cells in culture. Consistent with this, the number of Perilipin$^+$ adipocytes (FIGS. 3I-3K) and Safranin chondrocytes (FIGS. 3L-3N) in femur sections from 2 month-old mice did not differ between Clec11a$^{-/-}$ and sex matched littermate control mice.

Clec11a is Necessary for Normal Fracture Healing.

Figure 4E:
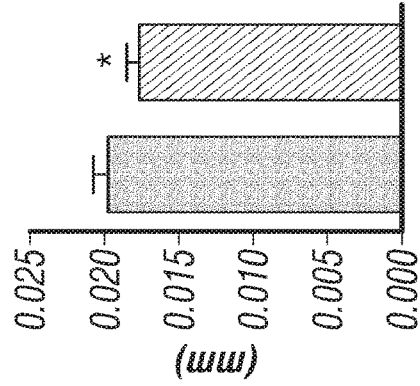
Figure 4F:
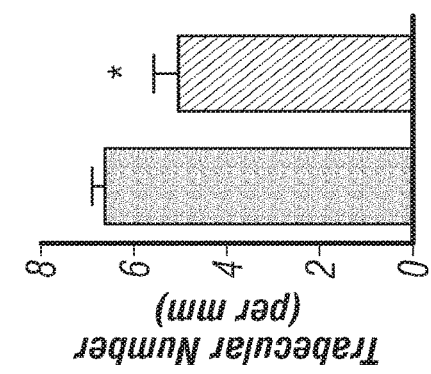
Figure 4G:
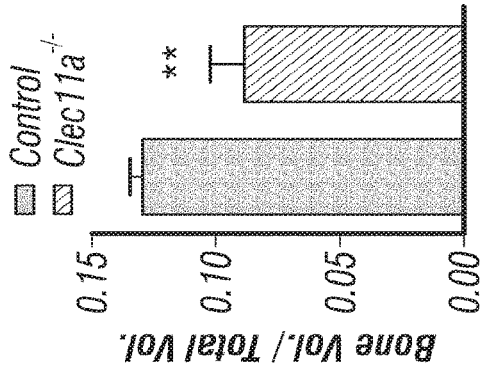
Figure 4H:
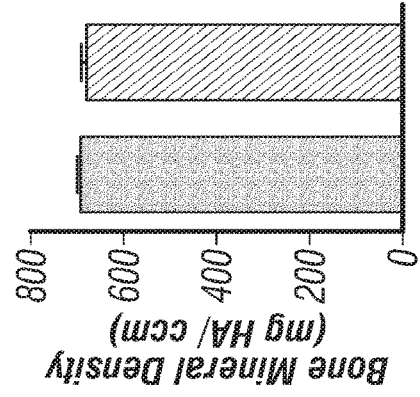
Figure 4I:
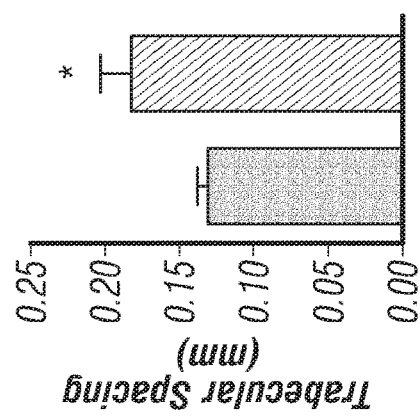

To test whether Clec11a regulates fracture healing, the inventors performed mid-diaphyseal femur fractures in 2 month-old Clec11a$^{-/-}$ and sex-matched littermate control mice. Two weeks after the fracture, Clec11a$^{-/-}$ mice had significantly less callus bone around the fracture site (FIG. 4A) and significantly more callus cartilage (FIG. 4B) as compared to controls, suggesting delayed endochondral ossification. MicroCT analysis of the callus at the fracture site two weeks after the fracture revealed significantly reduced trabecular bone volume, trabecular number, trabecular thickness, and trabecular connectivity density (FIGS. 4C-H) and significantly increased trabecular spacing (FIG.

Figure 4J:
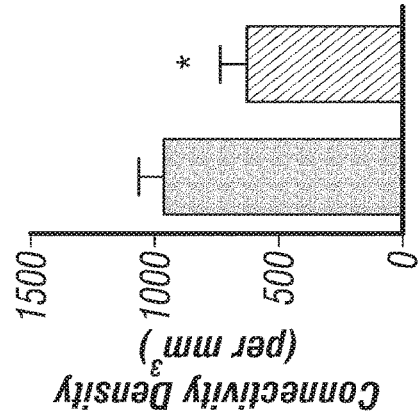

4I) in Clec11a⁻/⁻ mice. The bone mineral density in the callus did not significantly differ between Clec11a⁻/⁻ and control mice (FIG. 4J). Therefore, fracture healing is compromised in Clec11a⁻/⁻ mice.

Recombinant Clec11a Promotes Osteogenesis In Vitro and In Vivo.

To test whether Clec11a is sufficient to promote osteogenesis, the inventors constructed a HEK293 cell line that stably expressed mouse Clec11a with a C-terminal Flag tag. They affinity purified recombinant Clec11a (rClec11a) that had been secreted into the culture medium using anti-Flag M2 beads. Unfractionated bone marrow cells from wild-type mice were cultured to form CFU-F, which were then replated and grown under osteogenic culture conditions. Addition of rClec11a to these cultures significantly increased alizarin red staining, suggesting increased mineralization (FIG. 5A and FIG. 5B). The inventors also transiently expressed mouse Clec11a cDNA in the MC3T3-E1 mouse pre-osteoblast cell line (Wang et al., 1999). MC3T3-E1 cells expressing Clec11a exhibited increased osteogenic differentiation in culture (FIG. 5C and FIG. 5D).

Figure 5E:
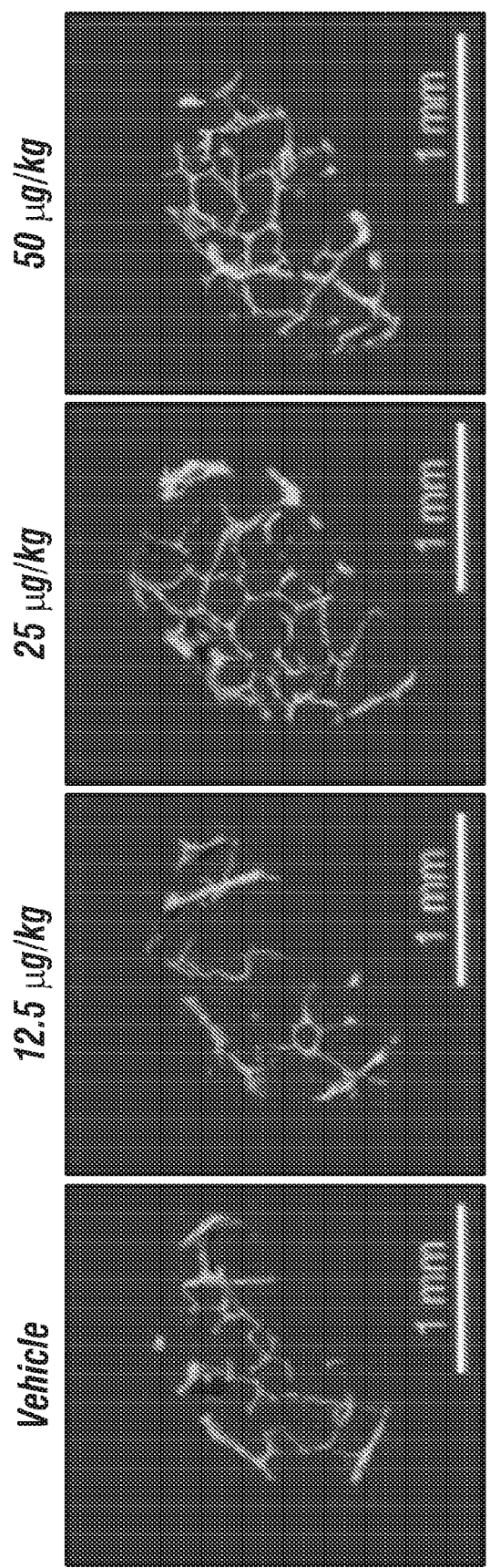

To test whether rClec11a promotes osteogenesis in vivo, the inventors administered daily subcutaneous injections of rClec11a to 2 month-old wild-type mice for 28 days. Consistent with the in vitro data, rClec11a dose-dependently increased trabecular bone volume in the distal femur metaphysis (FIG. 5E and FIG. 5F). The higher doses of rClec11a also significantly increased trabecular number and significantly reduced trabecular spacing (FIGS. 5G-5I). The increased osteogenesis in mice administered Clec11a was mainly due to increased bone formation (FIG. 5J). They inventors did not detect any effect of Clec11a on bone resorption (FIG. 5K). MicroCT analysis showed that cortical bone parameters in the femur diaphysis were not affected by rClec11a injection in these experiments (FIGS. 10A-10F). rClec11a thus promotes osteogenesis in wild-type mice in vivo.

rClec11a Administration Prevents Osteoporosis.

Figure 11A:
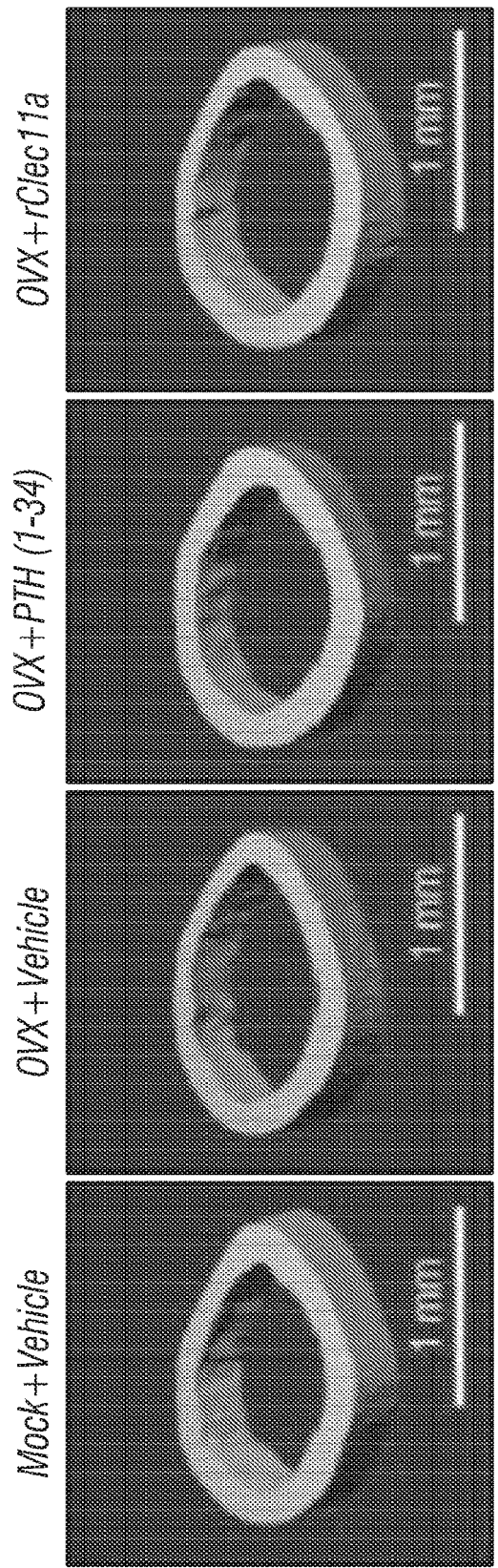
FIGS. 11A-F. Cortical bone analysis in ovariectomized mice, related to FIGS. 6A-I.
Figure 11B:
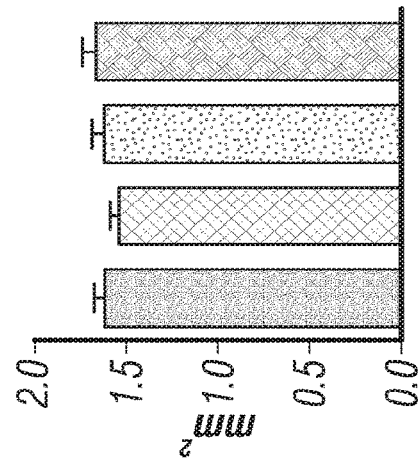
Figure 11C:
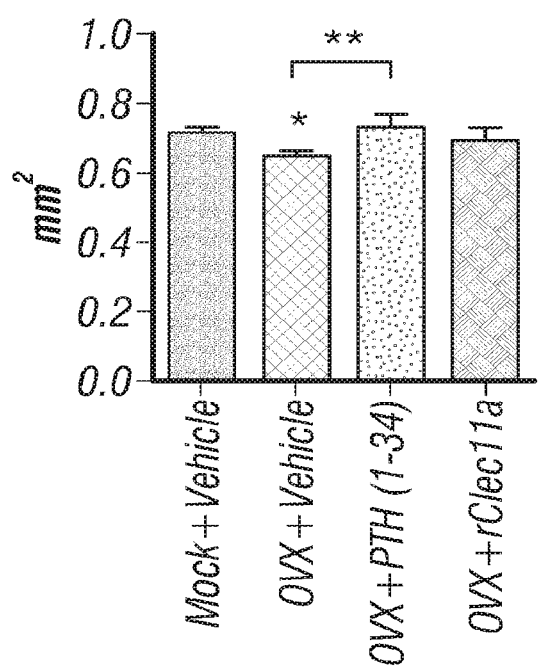
Figure 11D:
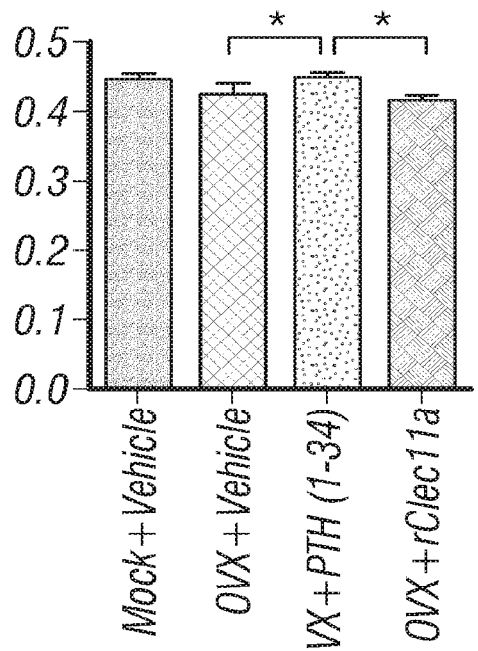
Figure 11E:
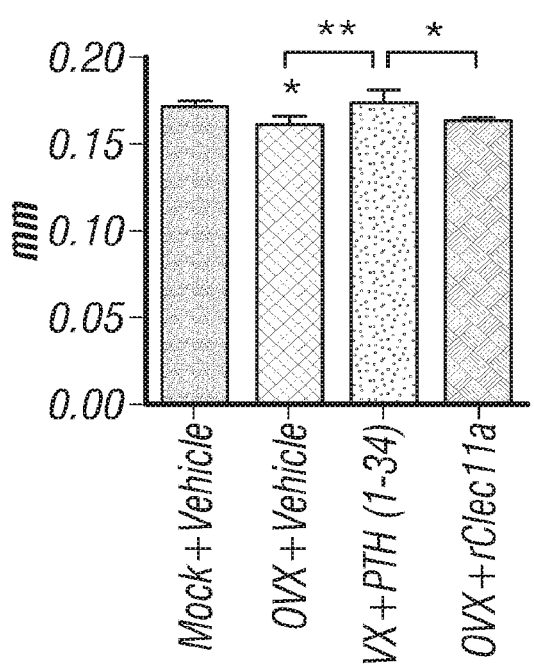
Figure 11F:
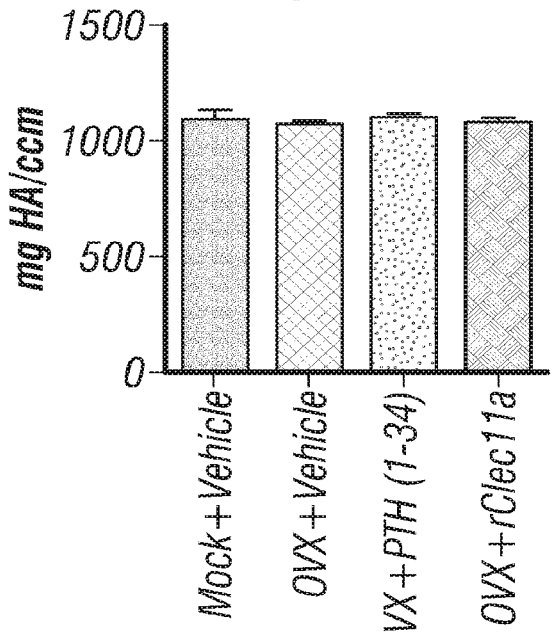
Figure 12A:
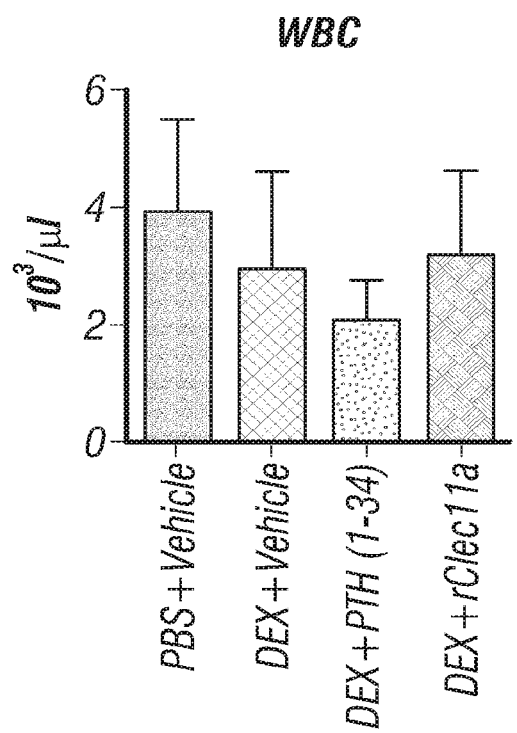
FIGS. 12A-J. Hematopoietic and cortical bone analysis in ovariectomized mice, related to FIGS. 7A-I.
Figure 12B:
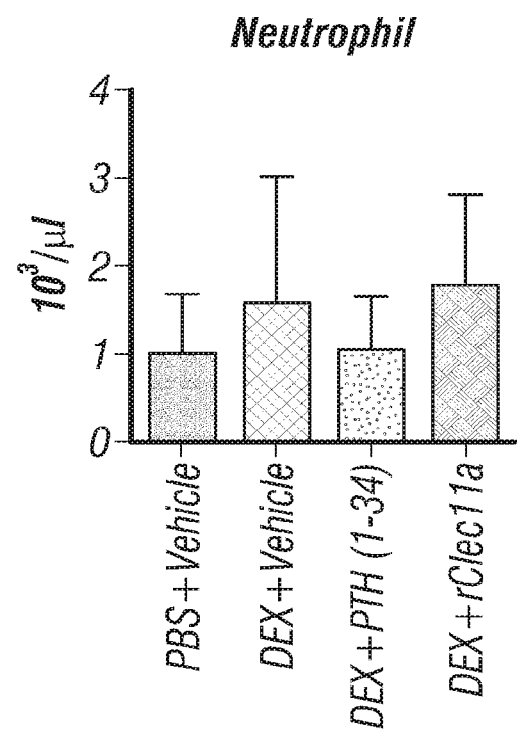
Figure 12C:
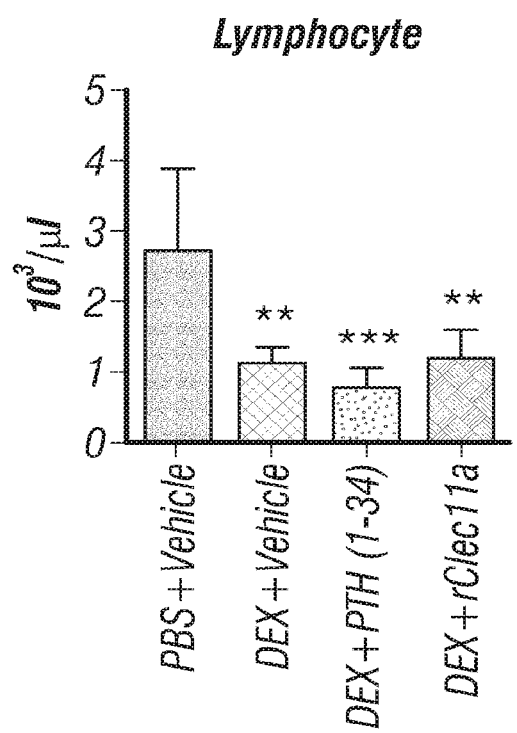
Figure 12D:
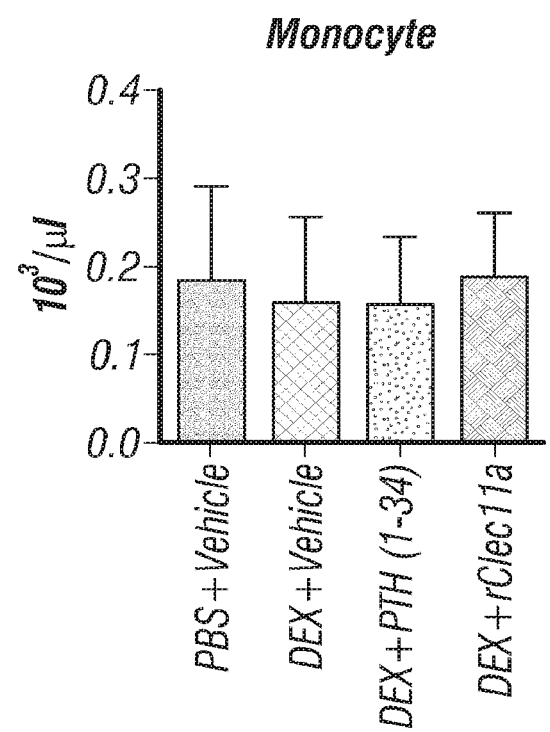
Figure 12E:
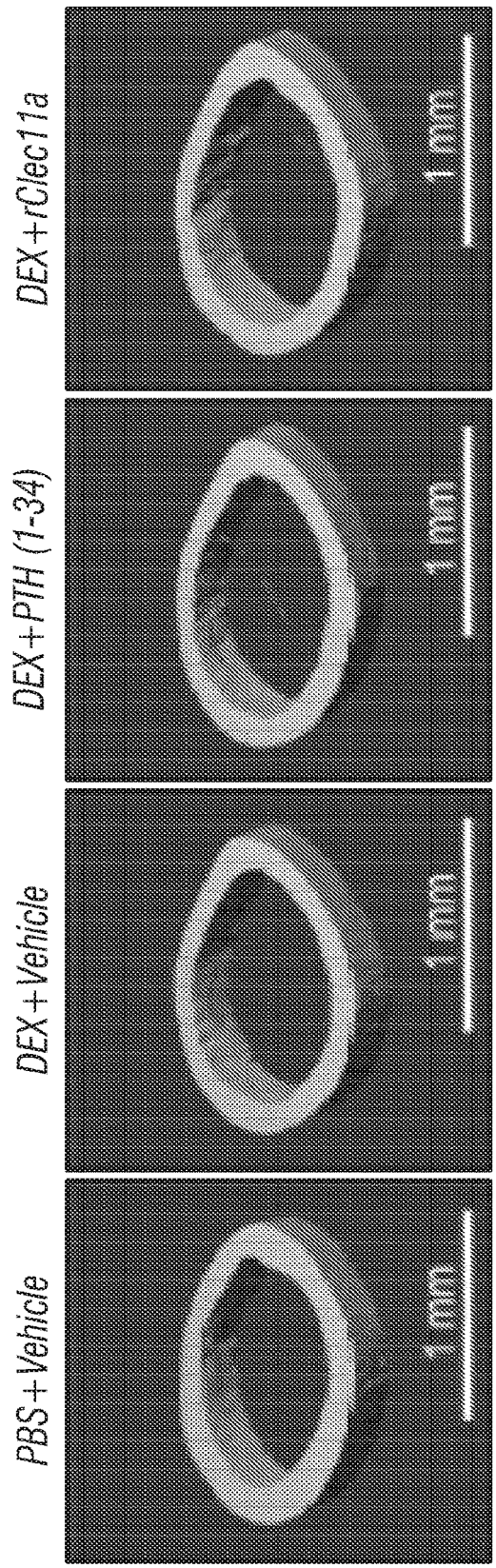
Figure 12F:
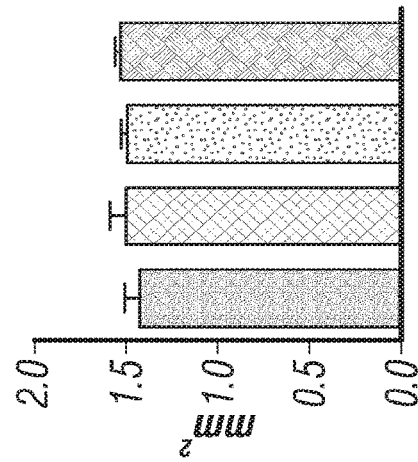
Figure 12G:
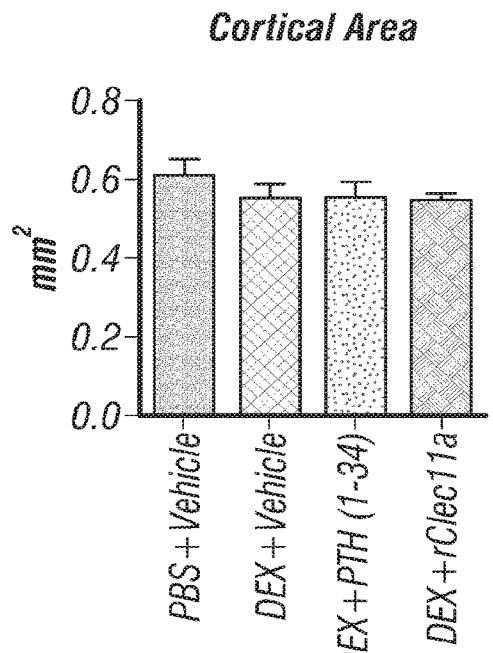
Figure 12H:
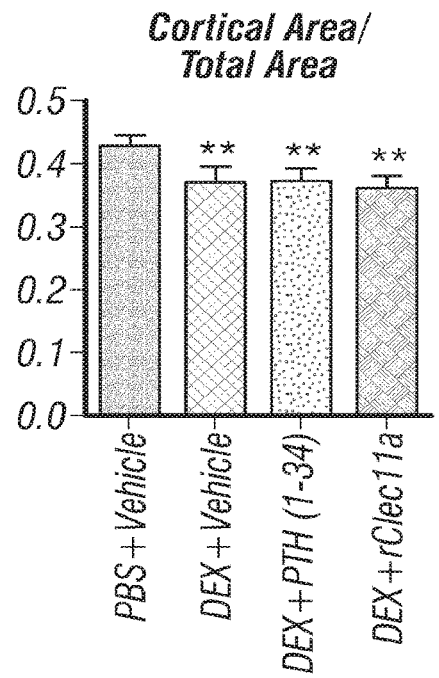
Figure 12I:
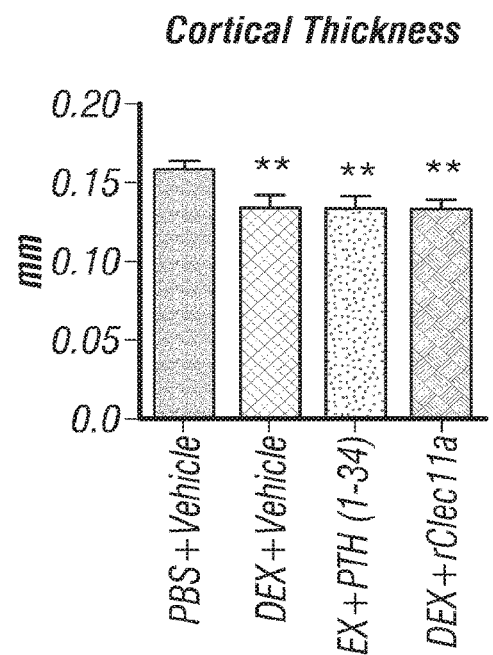
Figure 12J:
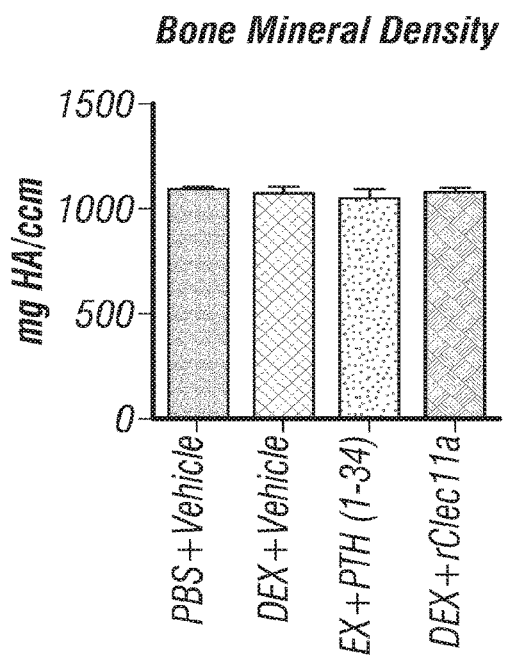
Figure 13A:
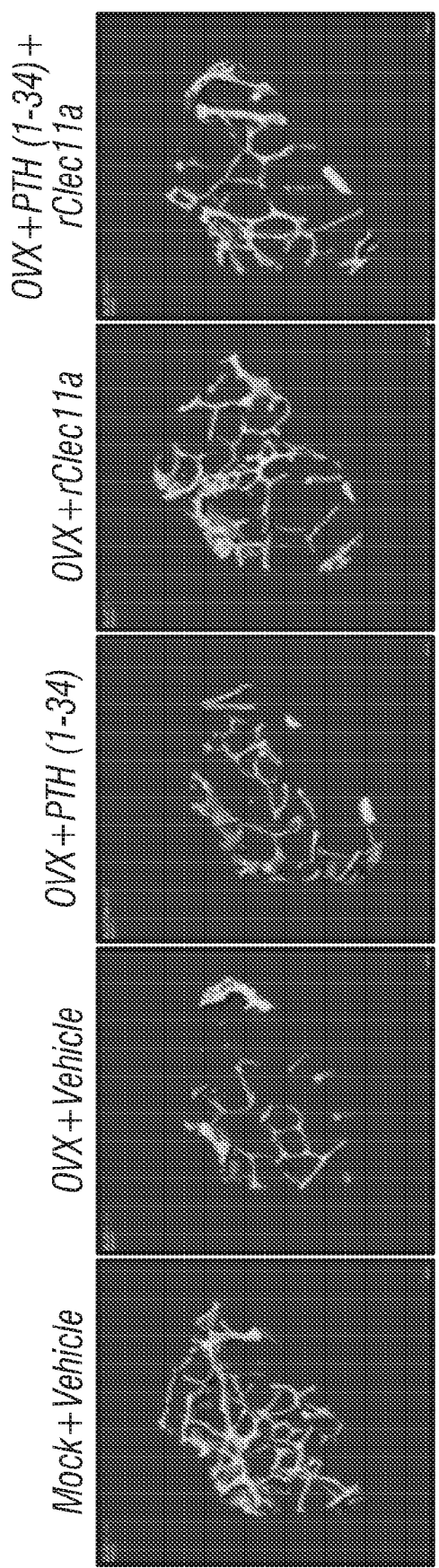

Ovariectomy in adult mice is a widely used primary osteoporosis model marked by increased bone resorption and bone loss (Rodan and Martin, 2000). The inventors ovariectomized mice at 2 months of age then administered daily subcutaneous injections of recombinant human parathyroid hormone (PTH) fragment 1-34, rClec11a, or vehicle for 28 days before analysis by microCT. MicroCT analysis showed that the trabecular and cortical bone volumes were significantly reduced in ovariectomized mice (FIG. 6A, FIG. 6B, and FIG. 11C) along with significantly reduced trabecular number (FIG. 6C) and significantly increased trabecular spacing (FIG. 6E). Daily administration of PTH to ovariectomized mice significantly increased trabecular bone volume (FIG. 6B) and trabecular number (FIG. 6C), while reducing trabecular spacing (FIG. 6E). PTH also significantly increased cortical area (FIG. 11C) and cortical thickness (FIG. S4E) in ovariectomized mice. Daily administration of rClec11a to ovariectomized mice also significantly increased trabecular bone volume (FIG. 6B) and trabecular number (FIG. 6C), while reducing trabecular spacing (FIG. 6E). However, rClec11a did not significantly affect cortical area (FIG. 11C) or cortical thickness (FIG. 11E) in ovariectomized mice. rClec11a can therefore prevent the loss of trabecular bone in ovariectomized mice, though it is not clear whether it can prevent the loss of cortical bone.

Figure 6F:
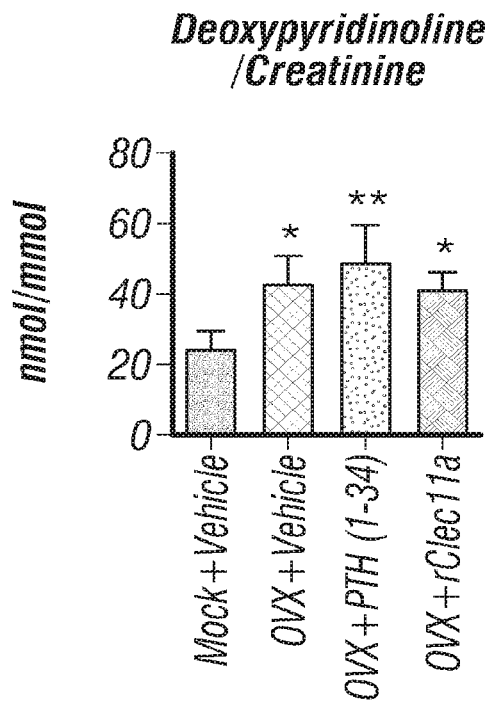
Figure 6G:
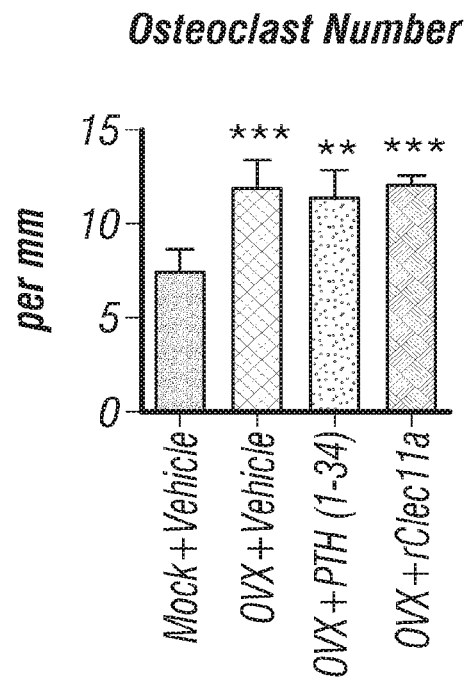
Figure 6H:
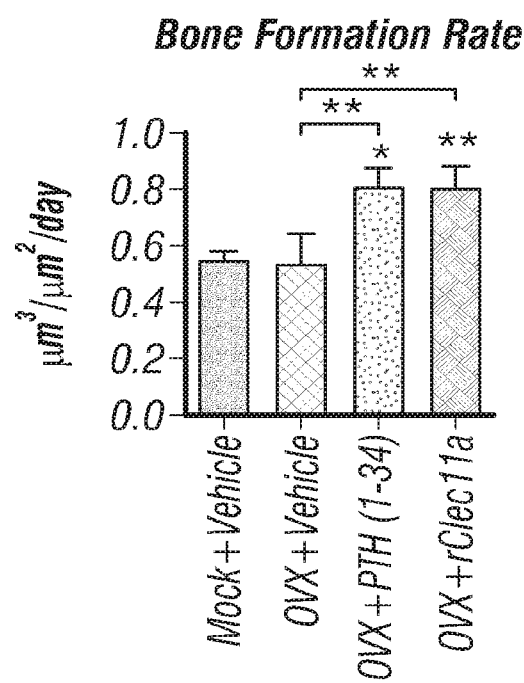
Figure 6I:
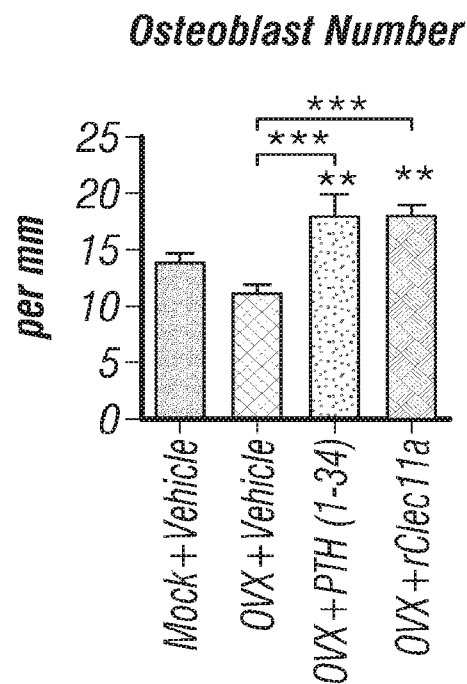

Consistent with the fact that ovariectomy increases bone resorption (Harada and Rodan, 2003), the urinary bone resorption marker deoxypyridinoline was significantly increased in ovariectomized mice as compared to sham operated controls (FIG. 6F). Administration of rClec11a or PTH did not significantly affect deoxypyridinoline levels (FIG. 6F) or numbers of osteoclasts (FIG. 6G) in ovariectomized mice. However, based on calcein double labeling and histomorphometry analysis in the femur metaphysis, the trabecular bone formation rate (FIG. 6H) and the number of osteoblasts associated with trabecular bones (FIG. 6I) were significantly increased by rClec11a or PTH administration. rClec11a thus prevented the loss of trabecular bone in ovariectomized mice by increasing the rate of bone formation.

The inventors also assessed the effect of rClec11a on a model of secondary osteoporosis in which bone loss was induced in mice by dexamethasone injection, mimicking glucocorticoid-induced osteoporosis in humans (McLaughlin et al., 2002; Weinstein et al., 1998). Daily intraperitoneal administration of 20 mg/kg dexamethasone for 4 weeks in mice significantly reduced lymphocyte numbers in the blood without significantly affecting neutrophil or monocyte counts (FIGS. 12A-12D). MicroCT analysis of the distal femur metaphysis showed significantly reduced trabecular bone volume and thickness in the dexamethasone-treated as compared to vehicle-treated mice (FIGS. 7A-7E). Treatment of dexamethasone-treated mice with PTH significantly increased trabecular bone volume, trabecular number, and trabecular thickness while significantly reducing trabecular spacing (FIGS. 7A-7E). Treatment of dexamethasone-treated mice with rClec11a also significantly increased trabecular bone volume and trabecular number while significantly reducing trabecular spacing (FIGS. 7A-7E). Dexamethasone treatment also significantly reduced cortical thickness but neither PTH nor rClec11a rescued this effect (FIGS. 12E-12J).

Figure 7A:
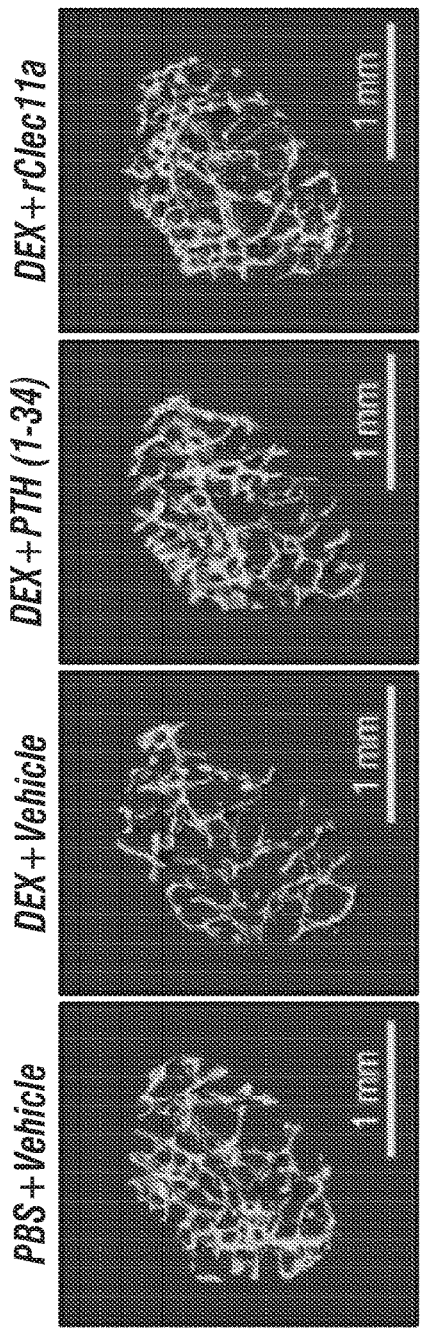
Figure 7B:
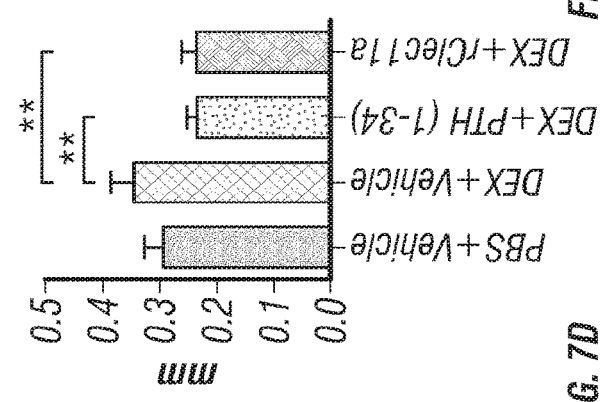
Figure 7C:
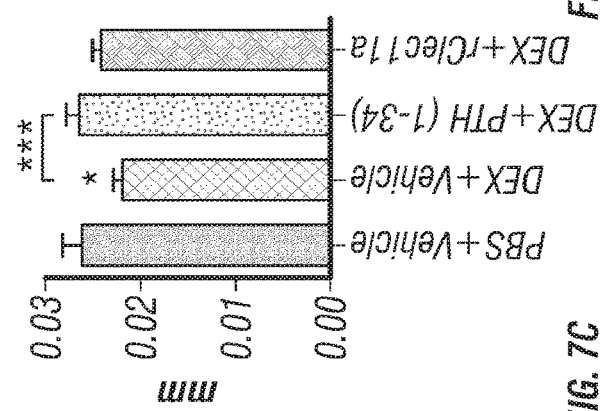
Figure 7D:
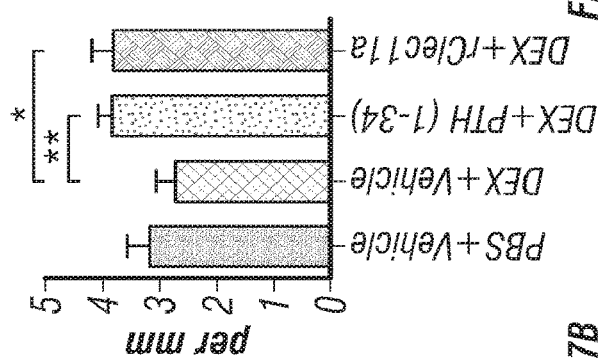
Figure 7E:
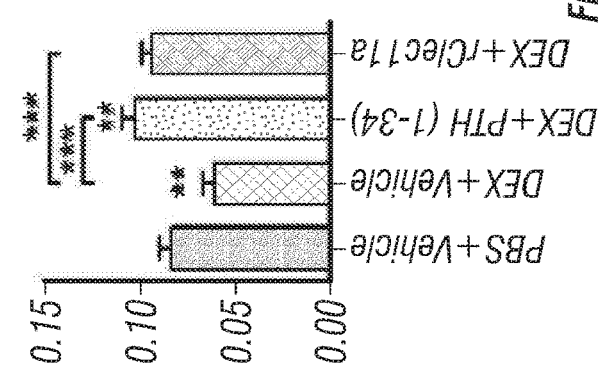
Figure 7F:
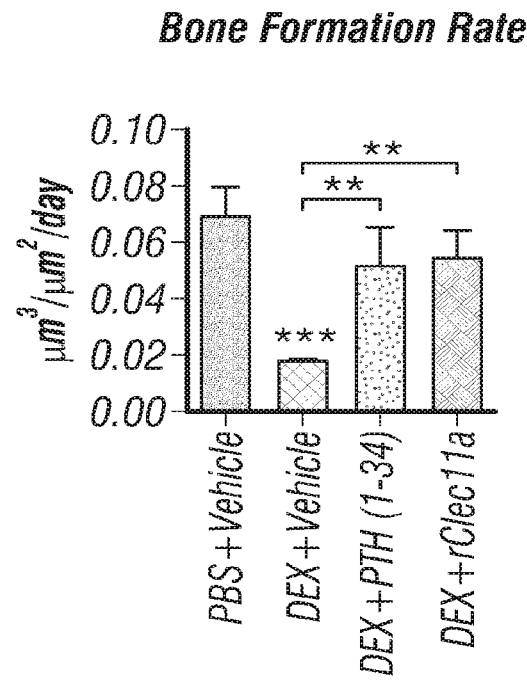
Figure 7G:
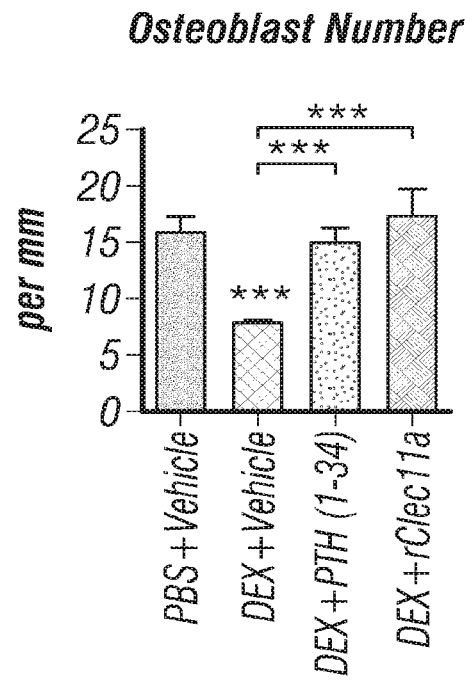
Figure 7H:
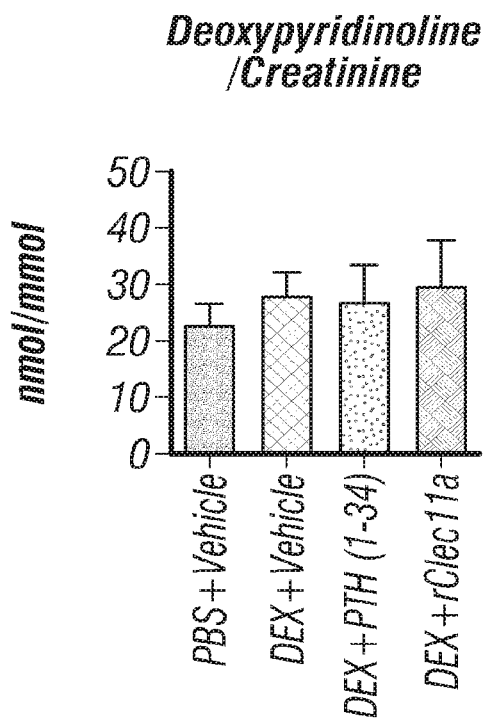
Figure 7I:
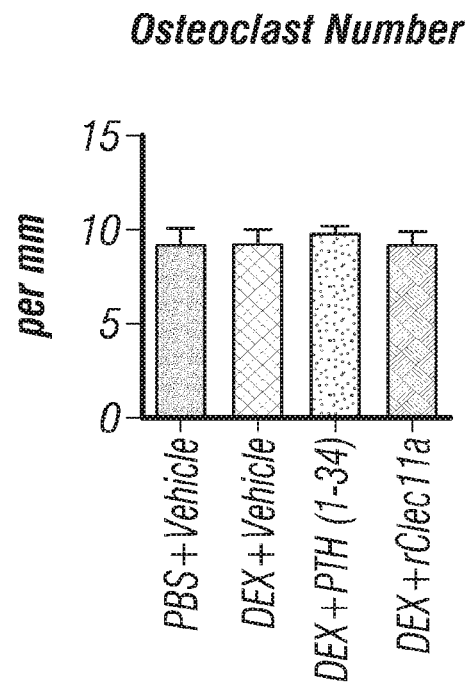

Consistent with the fact that dexamethasone treatment reduces bone formation (Harada and Rodan, 2003), the rate of trabecular bone formation based on calcein double labeling (FIG. 7F) and the numbers of osteoblasts associated with trabecular bones (FIG. 7G) were significantly reduced in dexamethasone-treated as compared to vehicle-treated mice. Administration of PTH or rClec11a significantly increased the trabecular bone formation rate (FIG. 7F) and the number of osteoblasts (FIG. 7G) in dexamethasone-treated mice. As expected, dexamethasone treatment, or administration of PTH or rClec11a, did not significantly affect deoxypyridinoline levels (FIG. 7G) or osteoclast numbers (FIG. 7I). rClec11a thus prevented the loss of trabecular bone in dexamethasone-treated mice by increasing the rate of bone formation.

To test whether administration of rClec11a can reverse the osteoporosis that has already established, the inventors performed ovariectomy in 2 month-old mice and waited for 4 weeks before they subcutaneously injected PTH (1-34), rClec11a, or PTH (1-34) together with rClec11a daily for another 4 weeks. Injection of rClec11a in ovariectomized mice significantly increased the trabecular bone volume and trabecular number while significantly reducing the trabecular spacing in the distal femur metaphysis as compared to ovariectomized mice injected with vehicle (FIGS. 13A-13F). Co-injection of PTH (1-34) and rClec11a showed significantly increased trabecular bone number as compared to PTH (1-34) injection alone (FIG. 13C), suggesting that PTH (1-34) and rClec11a might have additive effects on osteogenesis.

Figure 14A:
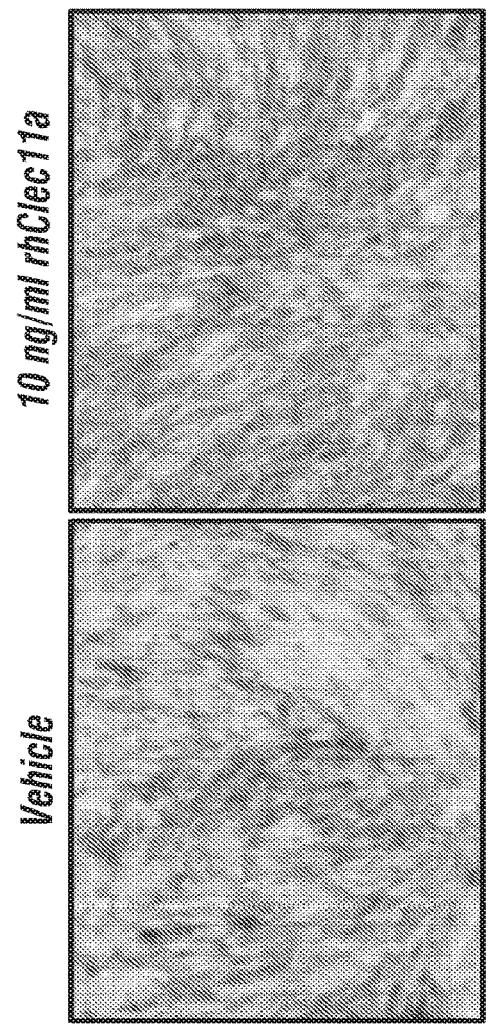
Figure 14B:
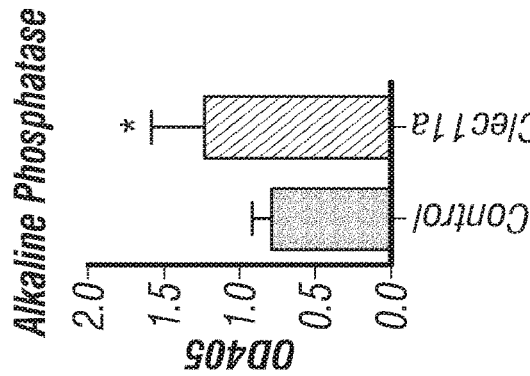
Figure 14C:
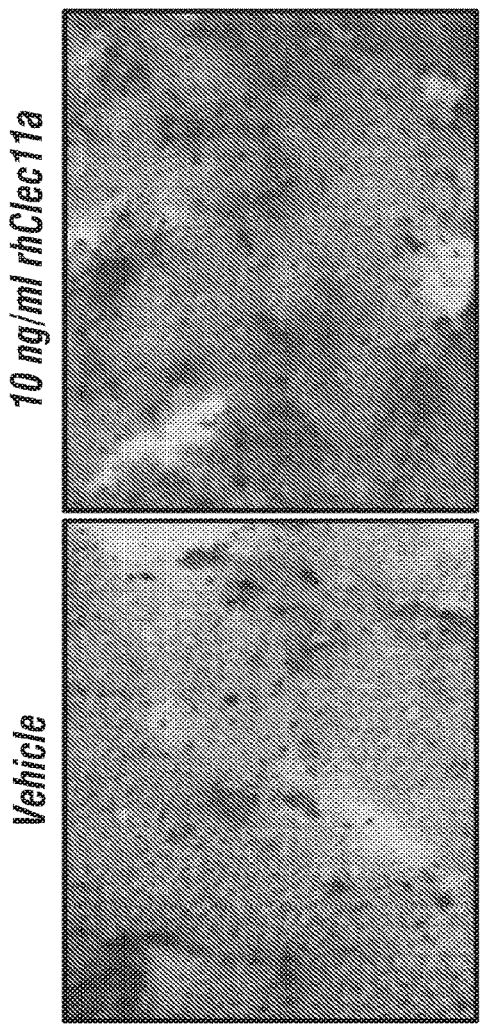
Figure 14D:
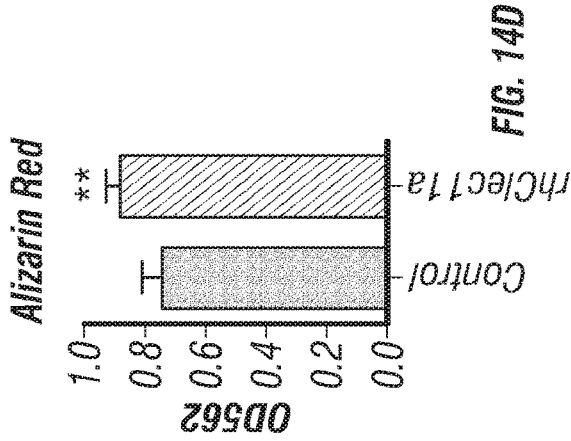

To test whether human Clec11a has similar osteogenic effects as mouse Clec11a, the inventors first added recombinant human Clec11a (rhClec11a) to human mesenchymal stem cell (hMSC) cultures and found that it significantly promoted osteoblast differentiation (FIGS. 14A and 14B) and mineralization (FIGS. 14C and 14D). Next, the inventors transplanted hMSCs into immunocompromised NSG mice in hydroxyapatite (HA)/tricalcium phosphate (TCP) particles. Treatment of the mice with rhClec11 by daily subcutaneous injection for 4 weeks significantly increased bone formation in vivo by the hMSCs (FIGS. 15A and 15B). Human Clec11a thus promotes osteogenesis by human cells in culture and in vivo.

Example 3—Discussion

Our studies have identified a new osteogenic factor, Clec11a, which acts on osteolineage cells to promote the maintenance of adult bone mass. Our data indicate that Clec11a is necessary and sufficient to promote osteogenesis in culture and in vivo. Clec11a deficiency significantly reduced bone volume in both limb bones and vertebrae of adult mice (FIGS. 2A-V). The observation that Clec11a is required for the maintenance of the adult skeleton is consistent with Clec11a expression by LepR$^+$ bone marrow stromal cells, which include the SSCs that generate most of the osteoblasts produced within adult bones but which do not contribute to the skeleton during development (Zhou et al., 2014). Nonetheless, Clec11a is also expressed by osteoblasts and it will remain unclear precisely which osteolineage cells are regulated by Clec11a until the Clec11a receptor is identified. Beyond LepR$^+$ cells and osteoblasts, it is also possible that Clec11a acts on Osterix-CreER-expressing bone marrow cells (Mizoguchi et al., 2014; Park et al., 2012), Osterix-CreER expressing periosteal cells (Maes et al., 2010) and/or Gremlin-CreER-expressing bone marrow cells (Worthley et al., 2015).

Clec11a protein was detected primarily around trabecular bone and in the matrix of cortical bone (FIGS. 1D-F). It appeared to be more highly concentrated in some regions of bone than in others. The antibody staining appeared to be quite specific because it was not observed in Clec11a$^{-/-}$ mice (FIGS. 1D-F). These data raise the possibility that Clec11a preferentially acts on osteogenic progenitors within certain regions of bone. Indeed, Clec11a deficiency and rClec11a administration had more acute effects on trabecular bone as compared to cortical bone. Nonetheless, Clec11a protein was strongly detected in cortical bone (FIG. 1F) and although Clec11a deficiency did not significantly reduce cortical bone in 2 or 10 month-old mice it did significantly reduce cortical bone in 16 month-old mice (FIG. 9A). Moreover, Clec11a deficiency significantly reduced the mechanical strength of femurs at 2, 10, and 16 months of age (FIG. 9I and FIG. 9J), raising the possibility that Clec11a regulates the biomechanical properties of bone independent of effects on bone volume. Administration of rClec11a for 28 days did not significantly affect cortical bone thickness (FIGS. 10A-F, FIGS. 11A-F, and FIGS. 12A-J), but it is possible that longer-term administration of Clec11a would. It is also important to bear in mind that Clec11a expression may be much more widespread than detected by anti-Clec11a antibody staining. Secreted factors are notoriously difficult to detect by antibody staining, so low levels of Clec11a protein in the cells that produce it may not be detected. Antibody staining may only be evident in areas of bone matrix where Clec11a protein is concentrated.

Previous studies showed that osteocalcin, an osteoblast-derived bone matrix protein, can act as a systemic hormone to regulate insulin levels in the pancreas after being released into the blood during bone resorption (Lee et al., 2007). Since Clec11a can be detected in both the bone and plasma (Ito et al., 2003), it is possible that Clec11a also acts as a feedback signal to promote osteogenesis after it is released from bone.

Phylogenic analysis showed that Clec11a is most closely related to Tetranectin (also known as Clec3b). Tetranectin expression increases during mineralization by osteogenic progenitors in culture and overexpression of Tetranectin in PC12 cells increases the bone content of tumors formed by these cells in immunocompromised mice (Wewer et al., 1994). Tetranectin deficient mice exhibit kyphosis as a result of asymmetric growth plate development in vertebrae (Iba et al., 2001); however, it is unknown whether Tetranectin is required for osteogenesis in vivo. Although Tetranectin is found in both cartilaginous fish and bony fish, Clec11a is only found in bony fish and higher vertebrate species. This suggests that Clec11a evolved in bony species to promote osteogenic differentiation and mineralization. Among mammals, Clec11a is highly conserved: the human and mouse Clec11a proteins exhibit 85% identity and 90% similarity.

Although human Clec11a has been shown to promote colony formation by human hematopoietic progenitors in culture, the inventors did not observe any hematopoietic defects in Clec11a$^{-/-}$ mice. Nonetheless, it is possible that Clec11a regulates some aspect of hematopoiesis under non-steady state conditions, such as in response to a hematopoietic stress. Future studies will be required to assess this.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

D378,314
D381,080
D473,944
U.S. Pat. No. 4,722,948
U.S. Pat. No. 4,843,112
U.S. Pat. No. 4,863,732
U.S. Pat. No. 4,975,526
U.S. Pat. No. 5,085,861
U.S. Pat. No. 5,162,114
U.S. Pat. No. 5,312,256
U.S. Pat. No. 5,364,268
U.S. Pat. No. 5,383,935
U.S. Pat. No. 5,397,358
U.S. Pat. No. 5,399,363
U.S. Pat. No. 5,405,388
U.S. Pat. No. 5,441,538
U.S. Pat. No. 5,456,723
U.S. Pat. No. 5,466,468

U.S. Pat. No. 5,531,791
U.S. Pat. No. 5,543,158
U.S. Pat. No. 5,571,185
U.S. Pat. No. 5,607,430
U.S. Pat. No. 5,624,462
U.S. Pat. No. 5,629,001
U.S. Pat. No. 5,639,402
U.S. Pat. No. 5,641,515
U.S. Pat. No. 5,658,338
U.S. Pat. No. 5,674,725
U.S. Pat. No. 5,709,547
U.S. Pat. No. 5,709,683
U.S. Pat. No. 5,720,750
U.S. Pat. No. 5,741,796
U.S. Pat. No. 5,759,035
U.S. Pat. No. 5,810,589
U.S. Pat. No. 5,819,748
U.S. Pat. No. 5,840,290
U.S. Pat. No. 5,885,287
U.S. Pat. No. 5,890,902
U.S. Pat. No. 5,895,425
U.S. Pat. No. 5,899,939
U.S. Pat. No. 5,906,488
U.S. Pat. No. 5,976,147
U.S. Pat. No. 6,018,094
U.S. Pat. No. 6,058,590
U.S. Pat. No. 6,074,674
U.S. Pat. No. 6,083,264
U.S. Pat. No. 6,126,662
U.S. Pat. No. 6,149,686
U.S. Pat. No. 6,149,688
U.S. Pat. No. 6,149,689
U.S. Pat. No. 6,203,545
U.S. Pat. No. 6,206,923
U.S. Pat. No. 6,213,775
U.S. Pat. No. 6,214,050
U.S. Pat. No. 6,217,617
U.S. Pat. No. 6,248,109
U.S. Pat. No. 6,270,346
U.S. Pat. No. 6,270,750
U.S. Pat. No. 6,281,195
U.S. Pat. No. 6,287,343
U.S. Pat. No. 6,288,043
U.S. Pat. No. 6,350,126
U.S. Pat. No. 6,350,283
U.S. Pat. No. 6,364,880
U.S. Pat. No. 6,370,418
U.S. Pat. No. 6,371,986
U.S. Pat. No. 6,436,146
U.S. Pat. No. 6,447,545
U.S. Pat. No. 6,458,136
U.S. Pat. No. 6,478,825
U.S. Pat. No. 6,485,754
U.S. Pat. No. 6,506,051
U.S. Pat. No. 6,537,277
U.S. Pat. No. 6,537,514
U.S. Pat. No. 6,540,770
U.S. Pat. No. 6,562,073
U.S. Pat. No. 6,562,074
U.S. Pat. No. 6,599,322
U.S. Pat. No. 6,607,557
U.S. Pat. No. 6,613,308
U.S. Pat. No. 6,648,917
U.S. Pat. No. 6,652,592
U.S. Pat. No. 6,662,805
U.S. Pat. No. 6,666,890
U.S. Pat. No. 6,689,136
U.S. Pat. No. 6,689,167
U.S. Pat. No. 6,730,129
U.S. Pat. No. 6,755,832
U.S. Pat. No. 6,761,738
U.S. Pat. No. 6,767,367
U.S. Pat. No. 6,786,908
U.S. Pat. No. 6,802,845
U.S. Pat. No. 6,852,129
U.S. Pat. No. 6,860,884
U.S. Pat. No. 6,899,734
U.S. Pat. No. 6,913,621
U.S. Pat. No. 6,918,766
U.S. Pat. No. 6,921,264
U.S. Pat. No. 6,923,830
U.S. Pat. No. 6,929,662
U.S. Pat. No. 6,936,270
U.S. Pat. No. 6,981,872
U.S. Pat. No. 6,981,975
U.S. Pat. No. 6,988,015
U.S. Pat. No. 6,989,031
U.S. Pat. No. 6,994,726
U.S. Pat. No. 7,001,551
U.S. Pat. No. 7,008,433
U.S. Pat. No. 7,022,137
U.S. Pat. No. 7,044,972
Akashi et al., Nature 404, 193-197, 2000.
Angel et al., *Cell,* 49:729, 1987b.
Angel et al., *Mol. Cell. Biol.,* 7:2256, 1987a.
Baichwal & Sugden, In: *Gene Transfer,* Kucherlapati (Ed), NY, Plenum Press, 117-148, 1986.
Banerji et al., *Cell,* 27(2 Pt 1):299-308, 1981.
Banerji et al., *Cell,* 33(3):729-740, 1983.
Bannwarth et al., Genomics 57, 316-317, 1999.
Bannwarth et al., J Biol Chem 273, 1911-1916, 1998.
Benvenisty and Neshif, *Proc. Natl. Acad. Sci. USA,* 83:9551-9555, 1986.
Berkhout et al., *Cell,* 59:273-282, 1989.
Bianco and Robey, Development 142, 1023-1027, 2015.
Black et al., Lancet 348, 1535-1541, 1996.
Blanar et al., *EMBO J.,* 8:1139, 1989.
Boshart et al., *Cell,* 41:521, 1985.
Bosze et al., *EMBO J.,* 5(7):1615-1623, 1986.
Braddock et al., *Cell,* 58:269, 1989.
Campbell et al., *J. Mol. Biol.,* 180:1-19, 1984.
Campo et al., *Nature,* 303:77, 1983.
Celander et al., *J. Virology,* 62:1314, 1988.
Chan et al., Cell 160, 285-298, 2015.
Chan et al, Nature 457, 490-494, 2009.
Chandler et al., Cell, 33:489, 1983.
Chang et al., *Mol. Cell. Biol.,* 9:2153, 1989.
Chatterjee et al., *Proc. Natl. Acad. Sci. USA,* 86:9114, 1989.
Chen and Okayama, *Mol. Cell Biol.,* 7:2745-2752, 1987.
Choi et al., *Cell,* 53:519, 1988.
Coffin, In: *Virology,* Fields et al. (Eds.), Raven Press, NY, 1437-1500, 1990.
Cohen et al., *J. Cell. Physiol.,* 5:75, 1987.
Costa et al., *Mol. Cell. Biol.,* 8:81, 1988.
Couch et al., *Am. Rev. Resp. Dis.,* 88:394-403, 1963.
Coupar et al., *Gene,* 68:1-10, 1988.
Cripe et al., *EMBO J.,* 6:3745, 1987.
Cui et al., Nature Medicine 17, 684-691, 2011.
Dandolo et al., *J. Virology,* 47:55-64, 1983.
De Villiers et al., *Nature,* 312(5991):242-246, 1984.
Deschamps et al., *Science,* 230:1174-1177, 1985.
Ding and Morrison, Nature 495, 231-235, 2013.
Ding et al., Nature 481, 457-462, 2012.

Dubensky et al., *Proc. Natl. Acad. Sci. USA,* 81:7529-7533, 1984.
Edbrooke et al., *Mol. Cell. Biol.,* 9:1908, 1989.
Edlund et al., *Science,* 230:912-916, 1985.
Egan et al., Histopathology 61, 1168-1173, 2012.
Fechheimer et al., *Proc Natl. Acad. Sci. USA,* 84:8463-8467, 1987.
Ferkol et al., *FASEB J.,* 7:1081-1091, 1993.
Fraley et al., *Proc Natl. Acad. Sci. USA,* 76:3348-3352, 1979
Friedenstein et al., Cell Tissue Kinet 3, 393-403, 1970.
Friedmann, *Science,* 244:1275-1281, 1989.
Fujita et al., *Cell,* 49:357, 1987.
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Ghosh-Choudhury et al., *EMBO J.,* 6:1733-1739, 1987.
Gilles et al., *Cell,* 33:717, 1983.
Gloss et al., *EMBO J.,* 6:3735, 1987.
Godbout et al., *Mol. Cell. Biol.,* 8:1169, 1988.
Gomez-Foix et al., *J. Biol. Chem.,* 267:25129-25134, 1992.
Goodbourn and Maniatis, *Proc. Natl. Acad. Sci. USA,* 85:1447, 1988.
Goodbourn et al., *Cell,* 45:601, 1986.
Gopal, *Mol. Cell Biol.,* 5:1188-1190, 1985.
Gopal-Srivastava et *Mol. Cell. Biol.,* 15(12):7081-90, 1995.
Graham and Prevec, In: *Methods in Molecular Biology: Gene Transfer and Expression Protocol,* Murray (Ed.), Humana Press, Clifton, NJ, 7:109-128, 1991.
Graham and van der Eb, *Virology,* 52:456-467, 1973.
Graham et al., *J. Gen. Virol.,* 36:59-72, 1977.
Greenbaum et al., Nature 495, 227-230, 2013.
Greene et al., *Immunology Today,* 10:272, 1989
Grunhaus and Horwitz, *Seminar in Virology,* 3:237-252, 1992.
Harada and Rodan, Nature 423, 349-355, 2003.
Harland and Weintraub, *J. Cell Biol.,* 101:1094-1099, 1985.
Hen et al., *Nature,* 321:249, 1986.
Hensel et al., *Lymphokine Res.,* 8:347, 1989.
Hermonat and Muzycska, *Proc. Nat'l Acad. Sci. USA,* 81:6466-6470, 1984.
Herr and Clarke, *Cell,* 45:461, 1986.
Hersdorffer et al., *DNA Cell Biol.,* 9:713-723, 1990.
Herz and Gerard, *Proc. Nat'l. Acad. Sci. USA* 90:2812-2816, 1993.
Hiraoka et al., *Hematology J.* 2, 307-315, 2001.
Hiraoka et al., Proceedings of the National Academy of Sciences USA 94, 7577-7582, 1997.
Hiraoka et al., The Hematology Journal 2, 307-315, 2001.
Hirochika et al., *J. Virol.,* 61:2599, 1987.
Holbrook et al., *Virology,* 157:211, 1987.
Horwich et al., *J. Virol.,* 64:642-650, 1990.
Huang et al., *Cell,* 27:245, 1981.
Hug et al., *Mol. Cell. Biol.,* 8:3065, 1988.
Hwang et al., *Mol. Cell. Biol.,* 10:585, 1990.
Iba et al., *Molecular Cellular Biology* 21, 7817-7825, 2001.
Imagawa et al., *Cell,* 51:251, 1987.
Imler et al., *Mol. Cell. Biol.,* 7:2558, 1987.
Ito et al., *Bone Marrow Transplantation* 32, 391-398, 2003.
Jakobovits et al., *Mol. Cell. Biol.,* 8:2555, 1988.
Jaynes et al., *Mol. Cell. Biol.,* 8:62, 1988.
Johnson et al., *Mol. Cell. Biol.,* 9:3393, 1989.
Jones and Shenk, *Cell,* 13:181-188, 1978.
Kaneda et al., *Science,* 243:375-378, 1989.
Karin et al., *Mol. Cell. Biol.,* 7:606, 1987.
Karlsson et al., *EMBO J.,* 5:2377-2385, 1986.
Katinka et al., *Cell,* 20:393, 1980.
Kato et al., *J Biol Chem.,* 266(6):3361-3364, 1991.
Kawamoto et al., *Mol. Cell. Biol.,* 8:267, 1988.
Keller et al., *Infection and Immunity* 77, 3864-3871, 2009.
Kiel et al., Blood 111, 4413-4414, 2008.
Kiel et al., Cell 121, 1109-1121, 2005.
Kiledjian et al., *Mol. Cell. Biol.,* 8:145, 1988.
Klamut et al., *Mol. Cell. Biol.,* 10:193, 1990.
Klein et al., *Nature,* 327:70-73, 1987.
Koch et al., *Mol. Cell. Biol.,* 9:303, 1989.
Kondo et al., Cell 91, 661-672, 1997.
Kraenzlin and Meier, Nature Reviews Endocrinology 7, 647-656, 2011.
Kriegler et al., *Cell,* 38:483, 1984.
Kriegler et al., *Cell,* 53:45, 1988.
Krishnan et al., J Clin Invest 116, 1202-1209, 2006.
Kuhl et al., *Cell,* 50:1057, 1987.
Kunisaki et al., Nature 502, 637-643, 2013.
Kunz et al., *Nucl. Acids Res.,* 17:1121, 1989.
Larsen et al., *Proc. Natl. Acad. Sci. USA.,* 83:8283, 1986.
Laspia et al., *Cell,* 59:283, 1989.
Latimer et al., *Mol. Cell. Biol.,* 10:760, 1990.
Le Gal La Salle et al., *Science,* 259:988-990, 1993.
Lee et al., Cell 130, 456-469, 2007.
Lee et al., *Nature,* 294:228, 1981.
Lee et al., *Nucleic Acids Res.,* 12:4191-206, 1984.
Leucht et al., Development 135, 2845-2854, 2008.
Levinson et al., *Nature,* 295:79, 1982.
Levrero et al., *Gene,* 101:195-202, 1991.
Li et al., J Biol Chem 280, 19883-19887, 2005.
Liberman et al., N Engl J Med 333, 1437-1443, 1995.
Lin et al., *Mol. Cell. Biol.,* 10:850, 1990.
Liu et al., PLoS One 8, e71318, 2013.
Luria et al., *EMBO. J.,* 6:3307, 1987.
Lusky et al., *Mol. Cell. Biol.,* 3:1108, 1983.
Mabuchi et al., Ann Transl Med 3, S17, 2015.
Mabuchi et al., Stem Cell Reports 1, 152-165, 2013.
Macejak and Sarnow, *Nature,* 353:90-94, 1991.
Maes et al., Developmental Cell 19, 329-344, 2010.
Mann et al., *Cell,* 33:153-159, 1983.
Markowitz et al., *J. Virol.,* 62:1120-1124, 1988.
McClung et al., N Engl J Med 370, 412-420, 2014.
McLaughlin et al., Bone 30, 924-930, 2002.
McNeall et al., *Gene,* 76:81, 1989.
Mendez-Ferrer et al., Nature 466, 829-834, 2010.
Michaelsson et al., BMJ 316, 1858-1863, 1998.
Miksicek et al., *Cell,* 46:203, 1986.
Mio et al., *Biochemical and Biophysical Research Communications* 249, 124-130, 1998.
Mizoguchi et al., Developmental Cell 29, 340-349, 2014.
Moreau et al., *Nucl. Acids Res.,* 9:6047, 1981.
Morikawa et al., J Exp Med 206, 2483-2496, 2009.
Morrison et al., Cell 101, 499-510, 2000.
Muesing et al., *Cell,* 48:691, 1987.
Nakamura et al., J Clin Invest 117, 3075-3086, 2007.
Neer et al., N Engl J Med 344, 1434-1441, 2001.
Ng et al., *Nuc. Acids Res.,* 17:601, 1989.
Nicolas and Rubinstein, In: *Vectors: A survey of molecular cloning vectors and their uses,* Rodriguez and Denhardt (Eds.), Stoneham: Butterworth, 494-513, 1988.
Nicolau and Sene, *Biochim. Biophys. Acta,* 721:185-190, 1982.
Nicolau et al., *Methods Enzymol.,* 149:157-176, 1987.
Oguro et al., Cell Stem Cell 13, 102-116, 2013.
Omatsu et al., Immunity 33, 387-399, 2010.
Omatsu et al., Nature 508, 536-540, 2014.
Ondek et al., *EMBO J.,* 6:1017, 1987.
Ono et al., Developmental Cell 29, 330-339, 2014.
Ornitz et al., *Mol. Cell. Biol.,* 7:3466, 1987.

Ouma et al., *Infection and Immunity* 78, 453-460, 2010.
Palmiter et al., *Cell,* 29:701, 1982.
Palmiter et al., *Nature,* 300:611, 1982.
Park et al., Cell Stem Cell 10, 259-272, 2012.
Paskind et al., *Virology,* 67:242-248, 1975.
Pech et al., *Mol. Cell. Biol.,* 9:396, 1989.
Pelletier and Sonenberg, *Nature,* 334:320-325, 1988.
Perales et al., *Proc. Natl. Acad. Sci. USA,* 91(9):4086-4090, 1994.
Perez-Stable and Constantin, *Mol. Cell. Biol.,* 10:1116, 1990.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.
Quinn et al., *Mol. Cell. Biol.,* 9:4713, 1989.
Racher et al., *Biotech. Techniques,* 9:169-174, 1995.
Ragot et al., *Nature,* 361:647-650, 1993.
Rahman et al., Bone Research 3, 15005, 2015.
Redondo et al., *Science,* 247:1225, 1990.
Reisman and Rotter, *Mol. Cell. Biol.,* 9:3571, 1989.
Remington's Pharmaceutical Sciences, 15th ed., 1035-1038 and 1570-1580, Mack Publishing Company, P A, 1980.
Renan, *Radiother. Oncol.,* 19:197-218, 1990.
Resendez Jr. et al., *Mol. Cell. Biol.,* 8:4579, 1988.
Rich et al., *Hum. Gene Ther.,* 4:461-476, 1993.
Ridgeway, In: *Vectors: A survey of molecular cloning vectors and their uses,* Stoneham: Butterworth, 467-492, 1988.
Ripe et al., *Mol. Cell. Biol.,* 9:2224, 1989.
Rippe et al., *Mol. Cell Biol.,* 10:689-695, 1990.
Riffling et al., *Nuc. Acids Res.,* 17:1619, 1989.
Rodan and Martin, Science 289, 1508-1514, 2000.
Rosen et al., *Cell,* 41:813, 1988.
Rosenfeld et al., *Cell,* 68:143-155, 1992.
Rosenfeld et al., *Science,* 252:431-434, 1991.
Roux et al., *Proc. Natl. Acad. Sci. USA,* 86:9079-9083, 1989.
Sacchetti et al., Cell 131, 324-336, 2007.
Sakai et al., *Genes and Dev.,* 2:1144, 1988.
Satake et al., *J. Virology,* 62:970, 1988.
Schaffner et al. *J Mol. Biol.,* 201:81, 1988.
Searle et al., *Mol. Cell. Biol.,* 5:1480, 1985.
Sherman et al., *Mol. Cell. Biol.,* 9:50, 1989.
Spalholz et al., *Cell,* 42:183, 1985.
Stephens and Hentschel, *Biochem. J,* 248:1, 1987.
Stratford-Perricaudet and Perricaudet, In: *Human Gene Transfer,* Cohen-Haguenauer and Boiron (Eds.), John Libbey Eurotext, France, 51-61, 1991.
Stratford-Perricaudet et al., *Hum. Gene. Ther.,* 1:241-256, 1990.
Stuart et al., *Nature,* 317:828, 1985.
Sugiyama et al., Immunity 25, 977-988, 2006.
Suire et al., Blood 119, e86-95, 2012.
Takashima et al., Cell 129, 1377-1388, 2007.
Takebe et al., *Mol. Cell. Biol.,* 8:466, 1988.
Tavernier et al., *Nature,* 301:634, 1983.
Taylor et al., *J. Biol. Chem.,* 264:15160, 1989.
Temin, In: *Gene Transfer,* Kucherlapati (Ed.), NY, Plenum Press, 149-188, 1986.
Thiesen et al., *J. Virology,* 62:614, 1988.
Top et al., *J. Infect. Dis.,* 124:155-160, 1971.
Tronche et al., *Mol. Biol. Med.,* 7:173, 1990.
Tur-Kaspa et al., *Mol. Cell Biol.,* 6:716-718, 1986.
Tyndell et al., *Nuc. Acids. Res.,* 9:6231, 1981.
Varmus et al., *Cell,* 25:23-36, 1981.
Vasseur et al., *Proc Natl. Acad. Sci. U.S.A.,* 77:1068, 1980.
Wagner et al., *Proc. Natl. Acad. Sci. USA,* 87(9):3410-3414, 1990.
Wang, et al., J Bone Miner Res 14, 893-903, 1999.
Weber et al., *Cell,* 36:983, 1984.
Weinberger et al. *Mol. Cell. Biol.,* 8:988, 1984.
Weinstein et al., J Clin Invest 102, 274-282, 1998.
Wewer et al., J Cell Biol 127, 1767-1775, 1994.
Wong et al., *Gene,* 10:87-94, 1980.
Worthley et al., Cell 160, 269-284, 2015.
Wu and Wu, *Adv. Drug Delivery Rev.,* 12:159-167, 1993.
Wu and Wu, *Biochemistry,* 27:887-892, 1988.
Wu and Wu, *J. Biol. Chem.,* 262:4429-4432, 1987.
Yakar and Rosen, Exp Biol Med 228, 245-252, 2003.
Yang et al., *Nat Med,* 13(4): p. 486-91, 2007.
Yang et al., *Proc. Natl. Acad. Sci. USA,* 87:9568-9572, 1990.
Yutzey et al. *Mol. Cell. Biol.,* 9:1397, 1989.
Zelenin et al., *FEBS Lett.,* 280:94-96, 1991.
Zhou et al., Cell Stem Cell 15, 154-168, 2014.

What is claimed is:

1. A method of treating a bone trauma, disease or disorder treatable by enhancing bone formation, strength, volume, or density in a human subject, the method comprising:
   administering a human C-type Lectin Domain Containing 11A (CLEC11a) to the subject, wherein the human CLEC11a comprises the sequence of SEQ ID NO: 10;
   wherein the human CLEC11a is administered systemically or locally;
   wherein if the human CLEC11a is administered locally, it is administered to a site of the bone in need of treatment; and
   wherein the human subject suffers from a bone fracture, osteopenia, osteoporosis, periodontal disease, or is in need of a spinal fusion or a dental implant.

2. The method according to claim 1, wherein the subject suffers from osteopenia or osteoporosis, and the human CLEC11a is administered systemically.

3. The method according to claim 1, wherein the subject suffers from a bone fracture, periodontal disease, or is in need of a spinal fusion or a dental implant, and the human CLEC11a is administered locally.

4. The method according to claim 1, wherein the human CLEC11a is administered in the form of a local injection.

5. The method according to claim 1, wherein the human CLEC11a is embedded in a slow release delivery vehicle.

6. The method according to claim 1, wherein the subject suffers from periodontal disease, and the human CLEC11a is administered as a topical sustained release composition during a periodontal procedure.

7. The method according to claim 1, wherein the administering of the human CLEC11a comprises administering to the subject a composition comprising: the human CLEC11a and mesenchymal stem/progenitor cells (MSC).

8. The method according to claim 1, wherein the administering of the human CLEC11a comprises administering to the subject a composition comprising: the human CLEC11a and an anabolic agent selected from the group consisting of parathyroid hormone (PTH), teriparatide, a parathyroid hormone-related analog, and a sclerostin inhibitor.

9. The method according to claim 1, wherein the administering of the human CLEC11a comprises administering to the subject a composition comprising: the human CLEC11a and an anti-resportive agent selected from the group consisting of bisphosphonates, calcitonin, denosumab, estrogen, and an estrogen agonist or antagonist.

10. The method according to claim 1, wherein the administering of the human CLEC11a comprises administering to the subject a composition comprising: the human CLEC11a and one or more pharmaceutical agents selected from the group consisting of a bisphosphonate, a selective estrogen receptor modulator (SERM), a sclerostin inhibitor, parathyroid hormone (PTH), and a parathyroid hormone-related analog.

* * * * *

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial sequence
<220> FEATURE:
<223> OTHER INFORMATION: Synthetic primer

<400> SEQUENCE: 1
aggtcctggg agggagtg                                                 18

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
```
gggcctcctg gagattctt                                                19

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3 gctctttcc agccttcctt                                                20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cttctgcatc ctgtcagcaa                                               20

<210> SEQ ID NO 5
<211> LENGTH: 19
<212> TYPE: DNA
<213> ORGANISM: Artificial sequence
<220> FEATURE:
<223> OTHER INFORMATION: Synthetic primer

<400> SEQUENCE: 5
tttgggtgct gggaagccc                                                19

<210> SEQ ID NO 6
<211> LENGTH: 19
<212> TYPE: DNA
<213> ORGANISM: Artificial sequence
<220> FEATURE:
<223> OTHER INFORMATION: Synthetic primer

<400> SEQUENCE: 6
ttgcactgag tcgcgggtg                                                19

<210> SEQ ID NO 7
<211> LENGTH: 23
<212> TYPE: DNA
<213> ORGANISM: Artificial sequence
<220> FEATURE:
<223> OTHER INFORMATION: Synthetic primer

<400> SEQUENCE: 7
gaggaagagg aaatcaccac agc                                           23

<210> SEQ ID NO 8
<211> LENGTH: 19
<212> TYPE: DNA
<213> ORGANISM: Artificial sequence
<220> FEATURE:
<223> OTHER INFORMATION: Synthetic primer

<400> SEQUENCE: 8
ttgcactgag tcgcgggtg                                                19

<210> SEQ ID NO 9
<211> LENGTH: 1423
<212> TYPE: DNA
<213> ORGANISM: Homo sapiens

<400> SEQUENCE: 9

```
gaccaacgga ccggacagag acgaggagag gaacaggaag agagaagctg ggagaatcgg      60
gaacctgggg gctagtgacc tgcacacagg gcaggggcac tcggcagttc ccagaggcca     120
cccctcccac cccagacatc cagacatctg aactttgggt gccaagagt ccagcttaat      180
gcaggcagcc tggcttttgg gggctttggt ggtcccccag ctcttgggct ttggccatgg     240
ggctcgggga gcagagaggg agtgggaggg aggctgggga ggtgcccagg aggaggagcg     300
ggagagggag gccctgatgc tgaagcatct gcaggaagcc ctaggactgc ctgctgggag     360
gggggatgag aatcctgccg gaactgttga gggaaaagag gactgggaga tggaggagga     420
ccaggggggag gaagaggagg aggaagcaac gccaacccca tcctccggcc ccagcccctc    480
tcccacccct gaggacatcg tcacttacat cctgggccgc ctggccggcc tggacgcagg     540
cctgcaccag ctgcacgtcc gtctgcacgc gttggacacc cgcgtggtcg agctgaccca     600
ggggctgcgg cagctgcgga acgcggcagg cgacacccgc gatgccgtgc aagccctgca     660
ggaggcgcag ggtcgcgccg agcgcgagca cggccgcttg gagggctgcc tgaaggggct     720
gcgcctgggc cacaagtgct tcctgctctc gcgcgacttc gaagctcagg cggcggcgca     780
ggcgcggtgc acggcgcggg gcgggagcct ggcgcagccg gcagaccgcc agcagatgga     840
ggcgctcact cggtacctgc gcgcggcgct cgctccctac aactggcccg tgtggctggg     900
cgtgcacgat cggcgcgccg agggcctcta cctcttcgaa aacggccagc gcgtgtcctt     960
cttcgcctgg catcgctcac cccgcccccga gctcggcgcc cagcccagcg cctcgccgca    1020
tccgctcagc ccggaccagc ccaacggtgg cacgctcgag aactgcgtgg cgcaggcctc    1080
tgacgacggc tcctggtggg accacgactg ccagcggcgt ctctactacg tctgcgagtt    1140
ccccttctag cggggccggt accccgcctc cctgcccatc ccaccacccg gccttttccct    1200
gcgccgtgcc caccctcctc cggaatctcc cttcccttcc tggccacgaa tggcagcgtc    1260
ctccccgacc cccagtctgg gcgcttctgg gagggctctt gcggtgccgg cactcctcct    1320
tgttagtgtc tttccttgaa ggggcgggca ccaggctagg tccggtgcca ataaatcctt    1380
gtggaatctg acttgagggg cagtgaaaaa aaaaaaaaaa aaa                      1423
```

<210> SEQ ID NO 10
<211> LENGTH: 323
<212> TYPE: PRT
<213> ORGANISM: Homo sapiens

<400> SEQUENCE: 10

```
Met Gln Ala Ala Trp Leu Leu Gly Ala Leu Val Val Pro Gln Leu Leu
1               5                   10                  15

Gly Phe Gly His Gly Ala Arg Gly Ala Glu Arg Glu Trp Glu Gly Gly
                20                  25                  30

Trp Gly Gly Ala Gln Glu Glu Glu Arg Glu Arg Glu Ala Leu Met Leu
        35                  40                  45

Lys His Leu Gln Glu Ala Leu Gly Leu Pro Ala Gly Arg Gly Asp Glu
    50                  55                  60

Asn Pro Ala Gly Thr Val Glu Gly Lys Glu Asp Trp Glu Met Glu Glu
65                  70                  75                  80

Asp Gln Gly Glu Glu Glu Glu Glu Ala Thr Pro Thr Pro Ser Ser
                85                  90                  95

Gly Pro Ser Pro Ser Pro Thr Pro Glu Asp Ile Val Thr Tyr Ile Leu
                100                 105                 110
```

```
Gly Arg Leu Ala Gly Leu Asp Ala Gly Leu His Gln Leu His Val Arg
        115                 120                 125

Leu His Ala Leu Asp Thr Arg Val Val Glu Leu Thr Gln Gly Leu Arg
    130                 135                 140

Gln Leu Arg Asn Ala Ala Gly Asp Thr Arg Asp Ala Val Gln Ala Leu
145                 150                 155                 160

Gln Glu Ala Gln Gly Arg Ala Glu Arg Glu His Gly Arg Leu Glu Gly
                165                 170                 175

Cys Leu Lys Gly Leu Arg Leu Gly His Lys Cys Phe Leu Leu Ser Arg
                180                 185                 190

Asp Phe Glu Ala Gln Ala Ala Ala Gln Ala Arg Cys Thr Ala Arg Gly
            195                 200                 205

Gly Ser Leu Ala Gln Pro Ala Asp Arg Gln Gln Met Glu Ala Leu Thr
        210                 215                 220

Arg Tyr Leu Arg Ala Ala Leu Ala Pro Tyr Asn Trp Pro Val Trp Leu
225                 230                 235                 240

Gly Val His Asp Arg Arg Ala Glu Gly Leu Tyr Leu Phe Glu Asn Gly
                245                 250                 255

Gln Arg Val Ser Phe Phe Ala Trp His Arg Ser Pro Arg Pro Glu Leu
            260                 265                 270

Gly Ala Gln Pro Ser Ala Ser Pro His Pro Leu Ser Pro Asp Gln Pro
        275                 280                 285

Asn Gly Gly Thr Leu Glu Asn Cys Val Ala Gln Ala Ser Asp Asp Gly
    290                 295                 300

Ser Trp Trp Asp His Asp Cys Gln Arg Arg Leu Tyr Tyr Val Cys Glu
305                 310                 315                 320

Phe Pro Phe
```